United States Patent
Mishra et al.

(10) Patent No.: US 11,939,291 B2
(45) Date of Patent: Mar. 26, 2024

(54) GRP94 SELECTIVE INHIBITORS AND USES THEREOF

(71) Applicants: University of Kansas, Lawrence, KS (US); University of South Florida, Tampa, FL (US)

(72) Inventors: Sanket Jaiprakash Mishra, Mishawaka, IN (US); Brian S. J. Blagg, Niles, MI (US); Chad Anthony Dickey, Tampa, FL (US)

(73) Assignees: University of Kansas, Lawrence, KS (US); University of South Florida, Tampa, FL (US)

( * ) Notice: Subject to any disclaimer, the term of this patent is extended or adjusted under 35 U.S.C. 154(b) by 352 days.

(21) Appl. No.: 17/226,359

(22) Filed: Apr. 9, 2021

(65) Prior Publication Data

US 2022/0024869 A1 Jan. 27, 2022

Related U.S. Application Data

(63) Continuation of application No. 16/346,039, filed as application No. PCT/US2017/059362 on Oct. 31, 2017, now Pat. No. 10,975,030.

(60) Provisional application No. 62/415,078, filed on Oct. 31, 2016.

(51) Int. Cl.
| | |
|---|---|
| *C07D 207/325* | (2006.01) |
| *A61P 27/06* | (2006.01) |
| *A61P 35/00* | (2006.01) |
| *C07C 13/18* | (2006.01) |
| *C07D 213/62* | (2006.01) |
| *C07D 401/06* | (2006.01) |

(52) U.S. Cl.
CPC .......... *C07D 207/325* (2013.01); *A61P 27/06* (2018.01); *A61P 35/00* (2018.01); *C07C 13/18* (2013.01); *C07D 213/62* (2013.01); *C07D 401/06* (2013.01)

(58) Field of Classification Search
CPC .............................. C07C 13/18; C07D 213/62
See application file for complete search history.

(56) References Cited

U.S. PATENT DOCUMENTS

| | | | |
|---|---|---|---|
| 6,258,843 B1 * | 7/2001 | Manley ................ | C07D 213/57 514/532 |
| 9,045,434 B1 | 6/2015 | Dickey et al. | |
| 2008/0269193 A1 | 10/2008 | Huang et al. | |
| 2010/0022635 A1 | 1/2010 | Rajewski | |
| 2014/0329812 A1 | 11/2014 | Giannini et al. | |
| 2016/0264560 A1 * | 9/2016 | Vogt ....................... | A61K 31/44 |

FOREIGN PATENT DOCUMENTS

| | | |
|---|---|---|
| WO | WO-94/05153 | 3/1994 |
| WO | WO-2011/035416 | 3/2011 |

OTHER PUBLICATIONS

Golub et al., Science, vol. 286, No. 531, 1999, p. 531-537 (Year: 1999).
International Preliminary Report on Patentability dated May 9, 2019 for PCT Application No. PCT/US2017/059362; 8 pages.
Mishra, Sanket; Structure-Based Design of Grp94-Selective Inhibitors', 78 pages (2014) https://kuscholarworks.ku.edu.
Non-Final Office Action in U.S. Appl. No. 16/346,039 dated Jul. 27, 2020.
Notice of Allowance in U.S. Appl. No. 16/346,039 dated Dec. 4, 2020.
Notice of Allowance in U.S. Appl. No. 16/346,039 dated Jan. 28, 2021.

(Continued)

Primary Examiner — Samantha L Shterengarts
Assistant Examiner — Karen Cheng
(74) Attorney, Agent, or Firm — Foley & Lardner LLP

(57) ABSTRACT

The present technology provides compounds according to Formula I or Formula III as well as compositions including such compounds useful for the treatment of metastatic cancer and/or glaucoma.

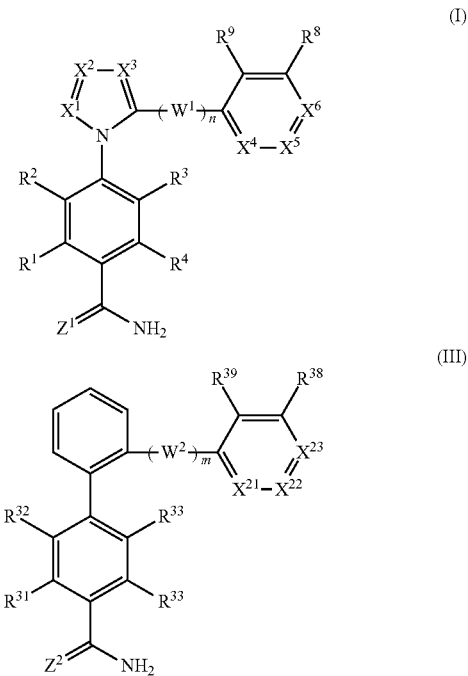

20 Claims, 6 Drawing Sheets

(56) References Cited

OTHER PUBLICATIONS

Targeted Cancer Therapies Fact Sheet from National Cancer Institute, see http://www.cancer.gov/about-cancer/treatment/types/targeted-therapies/targeted-therapies-fact-sheet, accessed Dec. 8, 2015, p. 1-6. (Year: 2015).

* cited by examiner

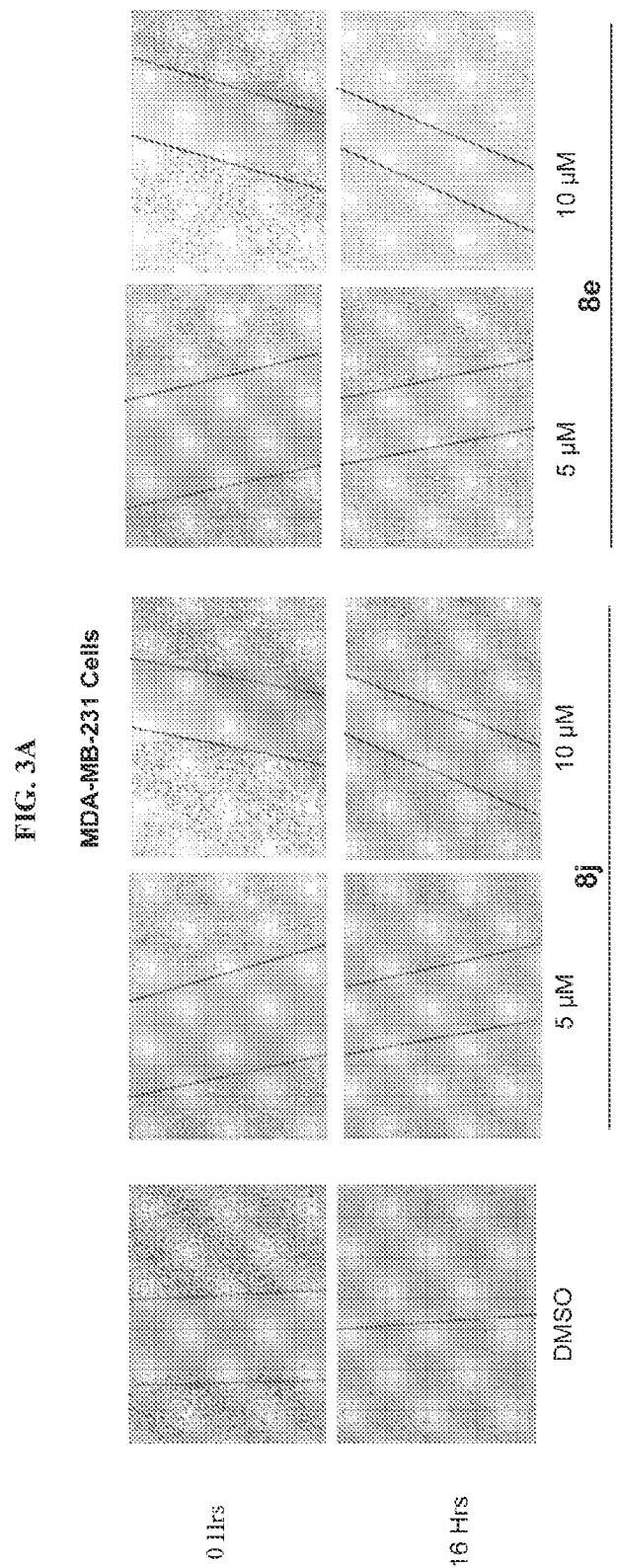

GRP94 SELECTIVE INHIBITORS AND USES THEREOF

CROSS-REFERENCE TO RELATED APPLICATIONS

This application is a continuation of U.S. patent application Ser. No. 16/346,039, filed Apr. 29, 2019, which is a U.S. National Phase Application under 35 U.S.C. § 371 of International Application No. PCT/US2017/059362, filed on Oct. 31, 2017, which claims the benefit of and priority to U.S. Provisional Patent Application No. 62/415,078, filed on Oct. 31, 2016, the entire disclosures of which are hereby incorporated by reference in their entireties for any and all purposes.

U.S. GOVERNMENT LICENSE RIGHTS

This invention was made with government support under grant numbers CA109265 and EY024232 awarded by the National Institutes of Health. The government has certain rights in the invention.

FIELD

The present technology generally relates to Grp94-selective compounds useful in treating metastatic cancer and glaucoma.

SUMMARY

In an aspect, a compound represented by Formula I is provided

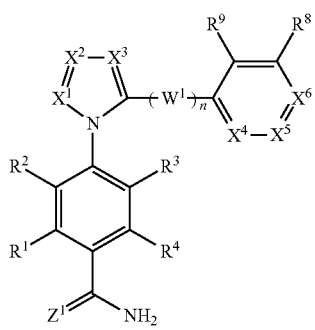

(I)

or a pharmaceutically acceptable salt and/or solvate thereof, where $X^1$, $X^2$, and $X^3$ are each independently CH or N; $X^4$ is N or C—$R^5$; $X^5$ is N or C—$R^6$; $X^6$ is N or C—$R^7$; $W^1$ is C($R^{10}$)($R^{11}$), O, or S; $R^1$ is alkyl, cycloalkyl, aryl, heterocyclyl, or $X^7$—$R^{12}$; $R^2$, $R^3$, $R^4$, $R^5$, $R^6$, $R^7$, $R^8$, $R^9$, $R^{10}$, and $R^{11}$ are each independently H, OH, alkyl, alkoxy, aryloxy, heteroaryloxy, amino, halo, trifluoromethyl, or cyano; $X^7$ is O, S, or NH; $R^{12}$ is alkyl, cycloalkyl, aryl, or heterocyclyl; $Z^1$ is O, S, or NH; and n is 0 or 1. It may be that $X^4$ is C—$R^5$, $X^5$ is N, and $X^6$ is C—$R^7$.

In an aspect, a compound represented by Formula III is provided

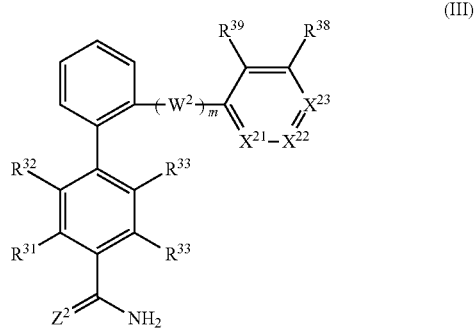

(III)

or a pharmaceutically acceptable salt and/or solvate thereof, wherein $X^{21}$ is N or C—$R^{35}$; $X^{22}$ is N or C—$R^{36}$; $X^{23}$ is N or C—$R^{37}$; $W^2$ is C($R^{40}$)($R^{41}$), O, or S; $R^{31}$ is alkyl, cycloalkyl, aryl, heterocyclyl, or $X^{24}$—$R^{42}$; $R^{32}$, $R^{33}$, $R^{34}$, $R^{35}$, $R^{36}$, $R^{37}$, $R^{38}$, $R^{39}$, $R^{40}$, and $R^{41}$ are each independently H, OH, alkyl, alkoxy, aryloxy, heteroaryloxy, amino, halo, trifluoromethyl, or cyano; $X^{24}$ is O, S, or NH; $R^{42}$ is alkyl, cycloalkyl, aryl, or heterocyclyl; $Z^2$ is O, S, or NH; and m is 0 or 1.

In an aspect, a composition is provided that includes any embodiment described herein of a compound of Formula I or III and a pharmaceutically acceptable carrier.

In an aspect, a pharmaceutical composition for treating cancer and/or glaucoma is provided where the composition includes an effective amount of a compound of Formula I or III and a pharmaceutically acceptable excipient.

In an aspect, a method for inhibiting cell motility of a cancer cell is provided. The method includes contacting the cell with a compound of Formula I or III.

In an aspect, a method of inhibiting death of a cell exhibiting mutant myocilin is provided, the method comprising contacting the cell with a compound of Formula I or III.

In an aspect, a method of treating a patient or animal from cancer or glaucoma, the method including administration of an effective amount of a compound of Formula I or III to the patient or animal. In the method, administration of the effective amount of a compound of Formula I or III to the patient or animal treats the patient or animal.

DESCRIPTION OF THE DRAWINGS

FIG. 2A provides the Western blot analysis of PC3-MM2 treated with DMSO (a control) and certain compounds of the present technology and divided into microsomal (MIC), mitochondrial (Mito), and cytoplasmic (Cyto) fractions. Representative western blots show the levels of integrin α2, integrin αL, Syne2, VAMP2, Rab10, and actin. FIG. 2B illustrates the results of PC3-MM2 cells treated with DMSO and certain compounds of the present technology, where the cells were subsequently fixed and stained with integrin α2 (red), phalloidin (gray), and DAPI (blue). Fluorescent images are representative of three independent biological replicates.

FIGS. 3A-B provides the results of a Wound-Healing scratch assay performed with certain compounds of the present technology. FIG. 3A illustrates the results when using MDA-MB-231 cells and FIG. 3B illustrates the results using PC-3 MM-2 cells. Camera mounted microscope was used to record migration at 0 h, 16 h, and 24 h. Representative live cell images at the corresponding time points of three independent biological replicates of cell migration assay are shown.

DETAILED DESCRIPTION

Figure 1:
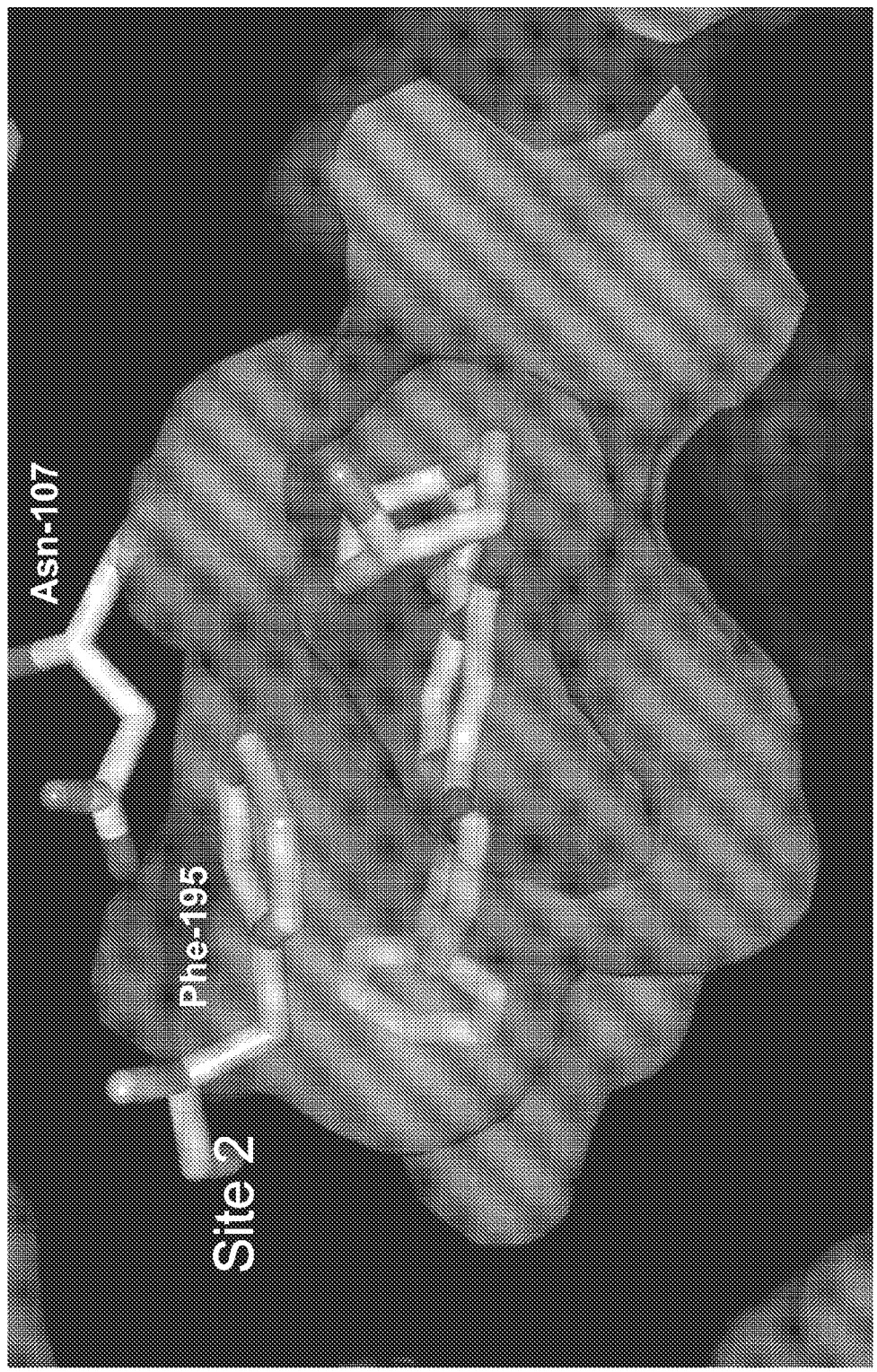
FIG. 1 provides molecular modeling results illustrating the modeled docked pose of a compound of the present technology in the binding site of Grp94 in the closed conformation where the phenyl appendage at the 2-position of the pyrrole occupies Site 2, according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Cycloalkyl groups may be substituted or unsubstituted. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Cycloalkylalkyl groups may be substituted or unsubstituted. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Alkenyl groups may be substituted or unsubstituted. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Alkynyl groups may be substituted or unsubstituted. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Aryl groups may be substituted or unsubstituted. The phrase "aryl groups" includes groups containing fused rings, such as fused aromatic-aliphatic ring systems (e.g., indanyl, tetrahydronaphthyl, and the like). Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl.

Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be substituted or unsubstituted. Thus, the phrase "heteroaryl groups" includes fused ring compounds as well as includes heteroaryl groups that have other groups bonded to one of the ring members, such as alkyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene. Such groups may further be substituted or unsubstituted.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "alkanoyl" and "alkanoyloxy" as used herein can refer, respectively, to —C(O)-alkyl and —O—C(O)-alkyl groups, where in some embodiments the alkanoyl or alkanoyloxy groups each contain 2-5 carbon atoms. Similarly, the terms "aryloyl" and "aryloyloxy" respectively refer to —C(O)-aryl and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylic acid" as used herein refers to a compound with a —C(O)OH group. The term "carboxylate" as used herein refers to a —C(O)O⁻ group. A "protected carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "ester" as used herein refers to —COOR$^{70}$ groups. R$^{70}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{80}$ groups, sulfoxides include —S(O)R$^{81}$ groups, sulfones include —SO$_2$R$^{82}$ groups, and sulfonyls include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{95}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "inline" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "trifluoromethyldiazirido" refers to

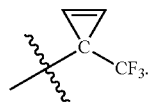 [SMILES: *C1(C(F)(F)F)C=C1]

The term "isocyano" refers to —NC.
The term "isothiocyano" refers to —NCS.
The term "pentafluorosulfanyl" refers to —SF$_5$.

The phrase "selective" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum when referring to a compound of the present technology refers to the compounds acting with a selectivity ratio for Grp94 over Hsp90α of at least >4:1, preferably >10:1, more preferably >50:1, and even more preferably >100:1. Such selectivity results in fewer off-target effects.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

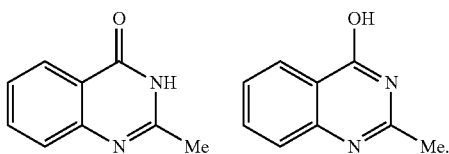

As another example, guanidines may exhibit the following isomeric forms in protic organic solution, also referred to as tautomers of each other:

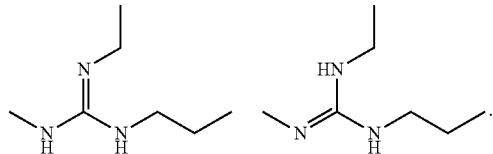

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

The Present Technology

The Heat Shock Protein 90 KDa (Hsp90) family of proteins is responsible for the conformational maturation of nascent polypeptides into their biologically active three-dimensional structures.[1] Hsp90 has generated great interest as a chemotherapeutic target due to its role in the modulation of cancer, neurodegenerative disorders, and infectious diseases. There are >200 protein substrates that require Hsp90 for their folding, maturation and/or activation, termed as Hsp90 clients.[2] During cellular stress, including elevated temperature, Hsp90 is induced to refold proteins that have undergone denaturation.[3,4] Similarly, Hsp90 is also upregulated in cancer cells, wherein it is required for the maturation of clients that drive the proliferation and growth of tumors.[4-7] Structurally, Hsp90 exists as a homodimer and each monomer contains a C-terminus, N-terminus, and a highly charged middle domain. The N-terminus contains an ATP-binding site, which is responsible for ATP hydrolysis and provides the energy necessary for the folding of client protein substrates.[8,9]

Hsp90 exists as four isoforms; Hsp90α and Hsp90β reside in cytoplasm, whereas Grp94 localizes in the endoplasmic reticulum, and Trap1 is found in the mitochondria. The natural products, geldanamycin and radicicol, were among the first Hsp90 inhibitors identified and have served as useful tools to study Hsp90 biology, validating Hsp90 as a druggable target for the development of new anti-cancer agents.[10-12] Consequently, 17 Hsp90 inhibitors have entered clinical trials for the treatment of cancer, however, all of these compounds exhibit pan inhibition of all four Hsp90 isoforms.[13,14] Unfortunately, some Hsp90 inhibitors have manifested undesired activity during these investigations, which is likely to hinder subsequent evaluation. It has also been hypothesized that many of these side effects result from pan-inhibition of all four Hsp90 isoforms.[15] Therefore, the development of isoform-selective Hsp90 inhibitors can provide an opportunity to fine-tune the drug discovery process while simultaneously identifying isoform-dependent clients.

Glucose regulated protein 94KDa (Grp94), also known as gp96 or endoplasmin, is the endoplasmic reticulum (ER) localized Hsp90 isoform. Grp94 is the most abundant protein in the ER lumen, where it is responsible for the maturation of secreted proteins that modulate immunity, cellular communication, and/or cell adhesion.[16] Grp94 is also a regulator of the unfolded protein response (UPR), a proteostatic mechanism triggered by the accumulation of misfolded proteins in the ER.[17,18] Client proteins that require Grp94 for their maturation include integrins, which are important for cell adhesion and metastasis, supporting Grp94 as a potential target for the development of anti-metastatic agents.[19] Grp94 knockdown experiments in the highly metastatic breast cancer cell line, MDA-MB-231, and the reactive oxygen species (ROS) resistant MCF-7 cell line resulted in the inhibition of cell migration and metastasis.[20] In addition, myocilin represents another Grp94-dependent protein, which upon its aggregation leads to increased ocular pressure that results in primary open angle glaucoma (POAG), supporting Grp94 inhibition as a viable approach for the treatment of glaucoma.[21] Recently, maturation of the GARP and Wnt co-receptor, LRP6, was shown to be Grp94-dependent.[24] Since LRP6 is overexpressed in multiple myeloma, Grp94 inhibition may be a useful for the treatment of such cancers.[22-24] As a consequence of these prior studies, the development of Grp94-selective inhibitors was sought for the treatment of various diseases, including cancer and glaucoma, while avoiding the potential side effects that result from inhibition of all four Hsp90 isoforms.

The N-terminal ATP-binding pocket of Grp94 is ~85% identical to other Hsp90 isoforms, which presents a significant challenge for the design of isoform-selective inhibitors.[25] However, a five amino acid (QEDGQ) insertion into the Grp94 primary sequence results in a conformational change within the ATP-binding pocket that produces a small hydrophobic cleft that can be utilized to develop selective inhibitors.[26] Although, 5'-N-ethylcarboxamidoadenosine (NEC A, Scheme 1 below) was the first inhibitor of Grp94 identified, it manifests non-specific agonistic activity against adenosine receptors.[27]

Scheme 1.

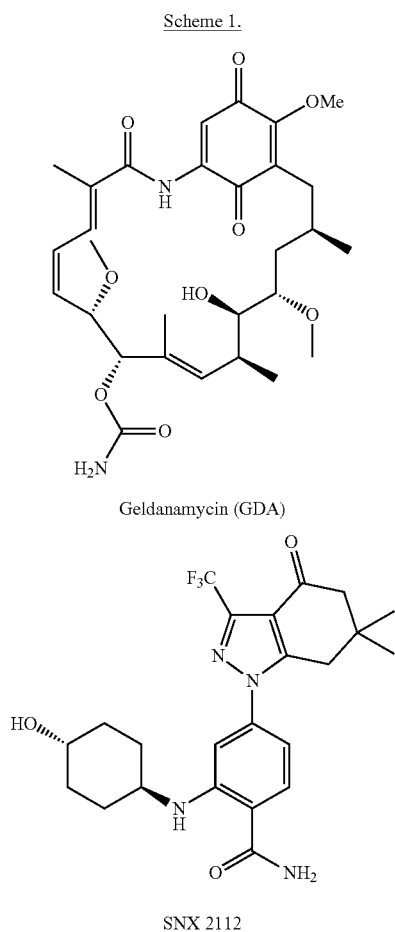

Geldanamycin (GDA)

SNX 2112

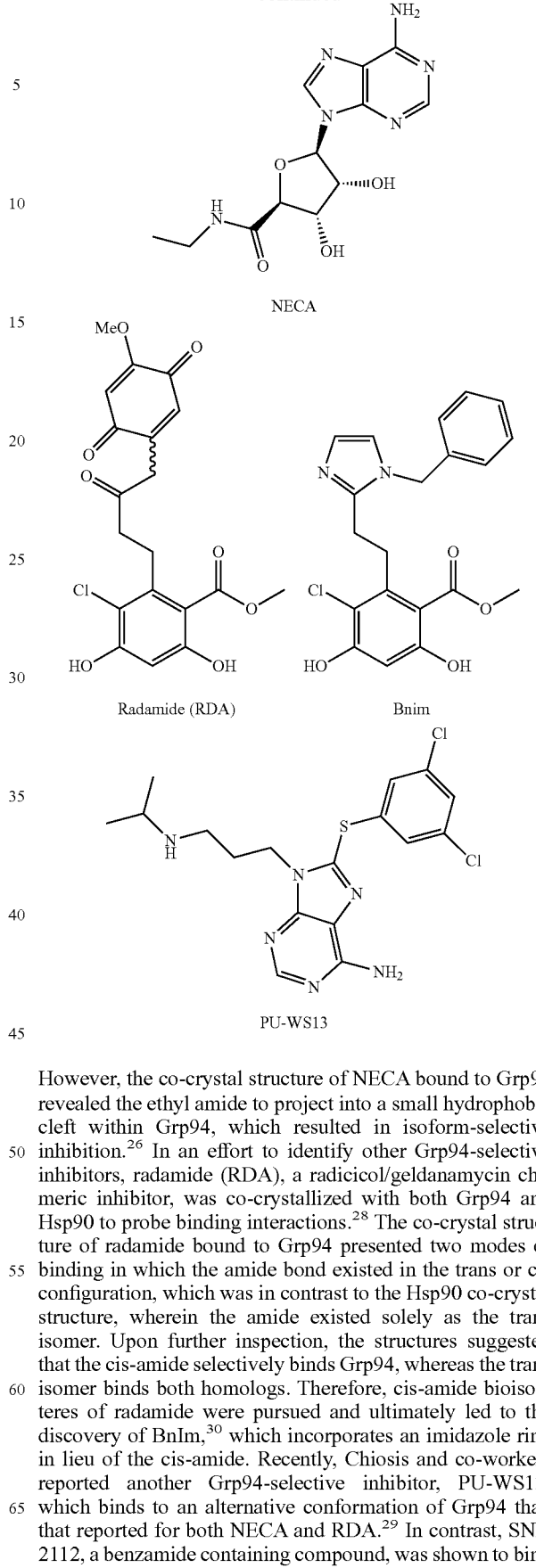

NECA

Radamide (RDA)

BnIm

PU-WS13

However, the co-crystal structure of NECA bound to Grp94 revealed the ethyl amide to project into a small hydrophobic cleft within Grp94, which resulted in isoform-selective inhibition.[26] In an effort to identify other Grp94-selective inhibitors, radamide (RDA), a radicicol/geldanamycin chimeric inhibitor, was co-crystallized with both Grp94 and Hsp90 to probe binding interactions.[28] The co-crystal structure of radamide bound to Grp94 presented two modes of binding in which the amide bond existed in the trans or cis configuration, which was in contrast to the Hsp90 co-crystal structure, wherein the amide existed solely as the trans isomer. Upon further inspection, the structures suggested that the cis-amide selectively binds Grp94, whereas the trans isomer binds both homologs. Therefore, cis-amide bioisosteres of radamide were pursued and ultimately led to the discovery of BnIm,[30] which incorporates an imidazole ring in lieu of the cis-amide. Recently, Chiosis and co-workers reported another Grp94-selective inhibitor, PU-WS13, which binds to an alternative conformation of Grp94 than that reported for both NECA and RDA.[29] In contrast, SNX 2112, a benzamide containing compound, was shown to bind both cytosolic Hsp90 isoforms (Hsp90α/β $K_i$: 4/6 nM) with high affinity, but manifested lower affinity (Grp94 $K_i$: 484 nM) against Grp94 and Trap 1.[32]

The present technology provides compounds unlike any previously described inhibitors of Grp94. The compounds of the present technology are Grp94-selective, binding Grp94 in a conformation that is disfavored for binding other Hsp90 isoforms. As discussed in the working examples, compounds according to the present technology inhibit Grp94 in cells and ultimately provided inhibition of cancer cell migration and induced the degradation of mutant myocilin. Thus, the compounds and compositions of the present technology provide new Grp94-selective inhibitors that are useful for the treatment of metastatic cancer and/or glaucoma.

Accordingly, in an aspect, a compound represented by Formula I is provided

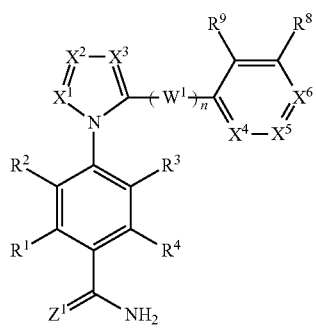
(I)

or a pharmaceutically acceptable salt and/or solvate thereof, where $X^1$, $X^2$, and $X^3$ are each independently CH or N; $X^4$ is N or C—$R^5$; $X^5$ is N or C—$R^6$; $X^6$ is N or C—$R^7$; $W^1$ is $C(R^{10})(R^a)$, O, or S; $R^1$ is alkyl, cycloalkyl, aryl, heterocyclyl, or $X^7$—$R^{12}$; $R^2$, $R^3$, $R^4$, $R^5$, $R^6$, $R^7$, $R^8$, $R^9$, $R^{10}$, and $R^{11}$ are each independently H, OH, alkyl, alkoxy, aryloxy, heteroaryloxy, amino, halo, trifluoromethyl, or cyano; $X^7$ is O, S, or NH; $R^{12}$ is alkyl, cycloalkyl, aryl, or heterocyclyl; $Z^1$ is O, S, or NH; and n is 0 or 1. In any embodiment herein, the compound of Formula I may be a compound represented by Formula Ia

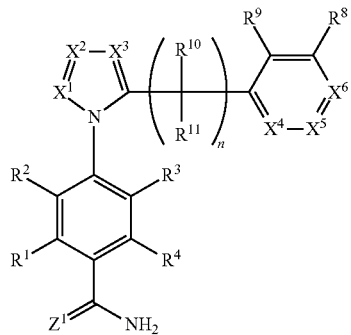
(Ia)

or a pharmaceutically acceptable salt and/or solvate thereof. It may be that, in any embodiment herein, $X^4$ is C—$R^5$, $X^5$ is N, and $X^6$ is C—$R^7$.

In any embodiment herein, it may be that $R^1$ is $C_1$-$C_6$ alkyl, $C_3$-$C_6$ cycloalkyl, substituted or unsubstituted phenyl, $C_2$-$C_5$ heterocyclyl, or $X^7$—$R^{12}$. For example, $R^1$ may be isopropyl, tert-butyl, cyclopropyl, cyclobutyl, cyclopentyl, cyclohexyl,

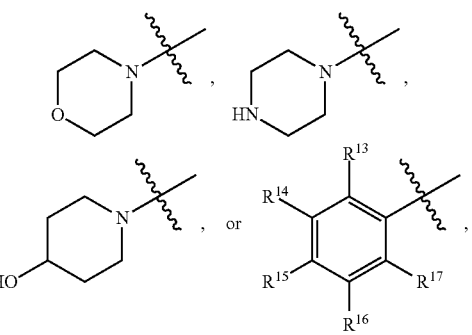

where $R^{13}$, $R^{14}$, $R^{15}$, $R^{16}$ and $R^{17}$ are each independently H, alkyl, alkoxy, amino, halo, trifluoromethyl, or cyano.

In any embodiment herein, it may be that $R^{12}$ is $C_1$-$C_6$ alkyl, $C_3$-$C_6$ cycloalkyl, substituted or unsubstituted phenyl, or $C_2$-$C_5$ heterocyclyl. It may be that $R^{12}$ is $C_1$-$C_6$ alkyl, $C_3$-$C_6$ cycloalkyl, substituted or unsubstituted phenyl, or non-aromatic $C_2$-$C_5$ heterocyclyl. As an example, $R^{12}$ may be isopropyl, tert-butyl, cyclopropyl, cyclobutyl, cyclopentyl, cyclohexyl,

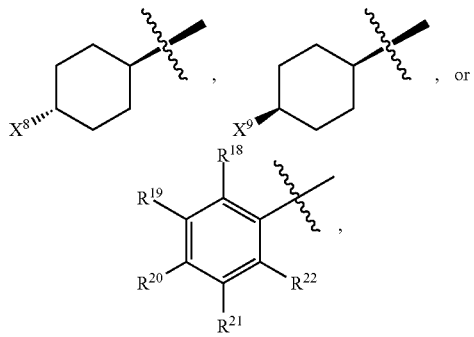

where $X^8$ and $X^9$ are each independently OH, amino, SH, sulfide, sulfoxide, or sulfone; and $R^{18}$, $R^{19}$, $R^{20}$, $R^{21}$ and $R^{22}$ are each independently H, alkyl, alkoxy, amino, halo, trifluoromethyl, or cyano.

In compounds according to Formula I, $R^5$, $R^6$, and $R^7$ may each independently be H, OH, alkyl, alkoxy, aryloxy, heteroaryloxy, amino, halo, trifluoromethyl, or cyano; and $R^8$ and $R^9$ may each be H. It may be that one of $R^5$, $R^6$, and $R^7$ is OH, alkyl, alkoxy, aryloxy, heteroaryloxy, amino, halo, trifluoromethyl, or cyano, and the remaining $R^5$, $R^6$, and $R^7$ are each H; and $R^8$ and $R^9$ are each H. It may be that one of $R^5$, $R^6$, and $R^7$ is OH, $C_1$-$C_6$ alkyl, $C_1$-$C_6$ alkoxy, amino, halo, trifluoromethyl, or cyano, and the remaining $R^5$, $R^6$, and $R^7$ are each H; and $R^8$ and $R^9$ are each H. In any embodiment herein, one of $R^5$, $R^6$, and $R^7$ may be OH, methyl, ethyl, n-propyl, isopropyl, methoxy, ethoxy, n-propyloxy, isopropyloxy, $NH_2$, NH—$CH_3$, $N(CH_3)_2$, halo, trifluoromethyl, or cyano, and the remaining $R^5$, $R^6$, and $R^7$ are each H; and $R^8$ and $R^9$ are each H.

In any of the above embodiments it may be that $X^4$ is C—$R^5$, $X^5$ is C—$R^6$, and $X^6$ is C—$R^7$, as illustrated by Formula II

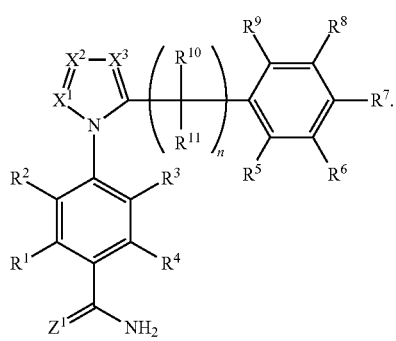
(II)
In any embodiment herein, it may be that $X^1$, $X^2$, and $X^3$ are each CH.
Examples of compounds according to Formula I include, but are not limited to,
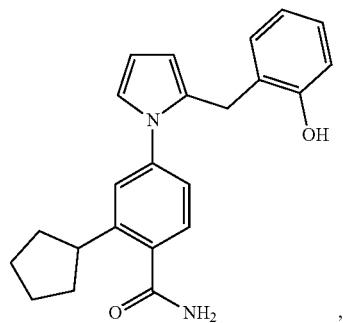
,
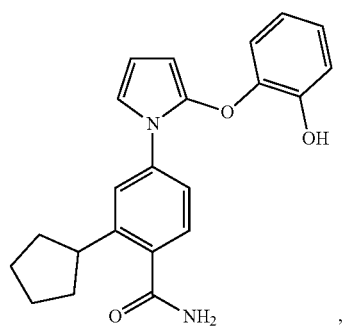
,
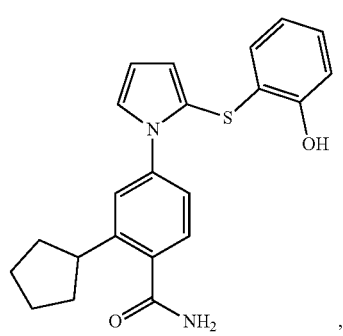
,
-continued
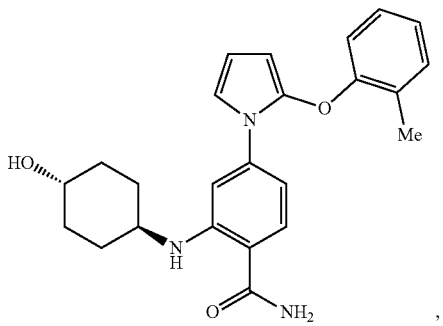
,
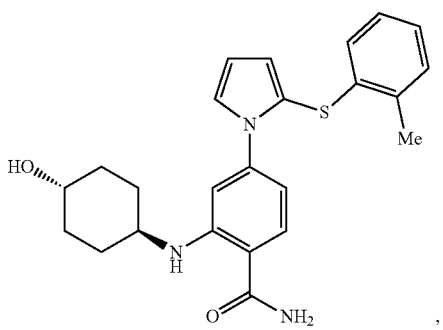
,
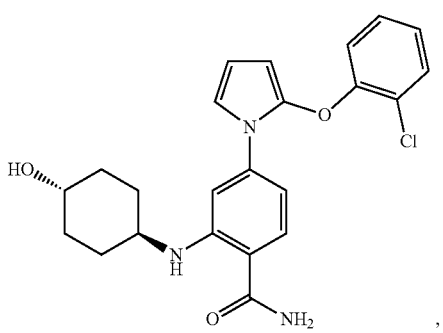
,
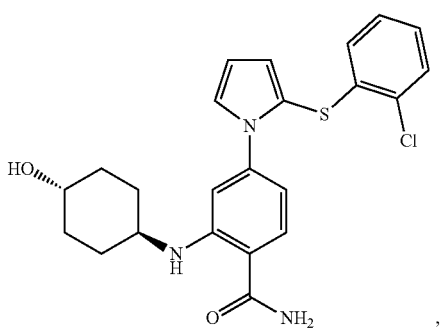
,
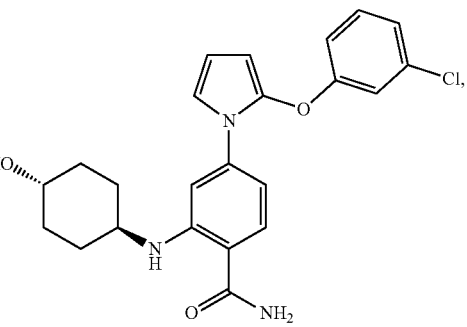
,

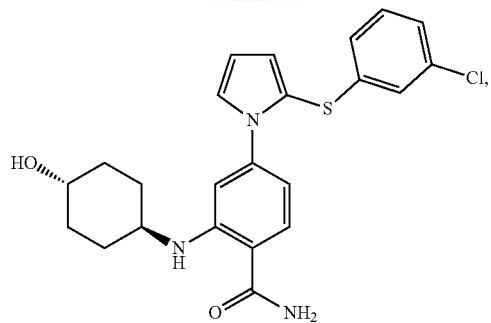
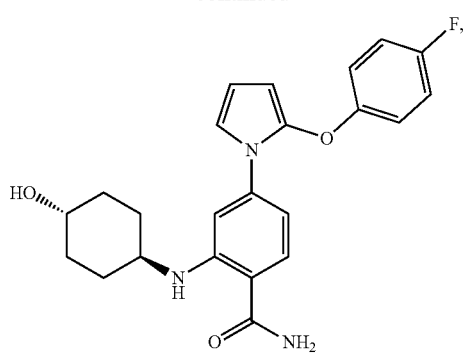
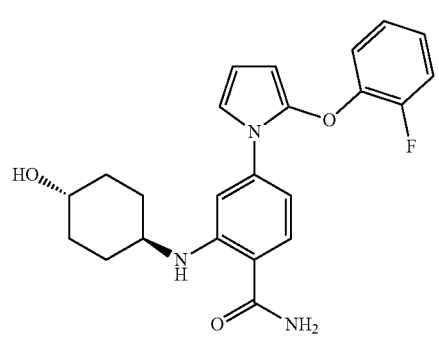
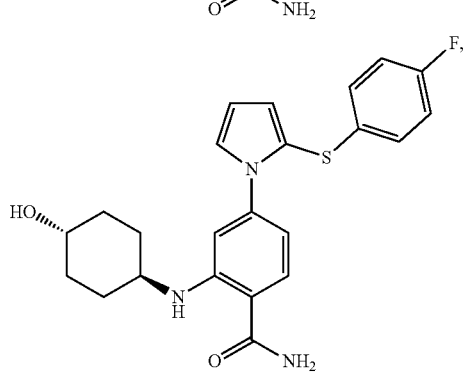
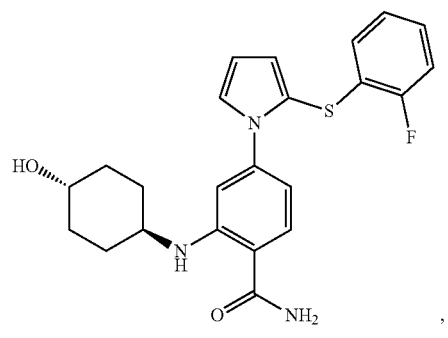
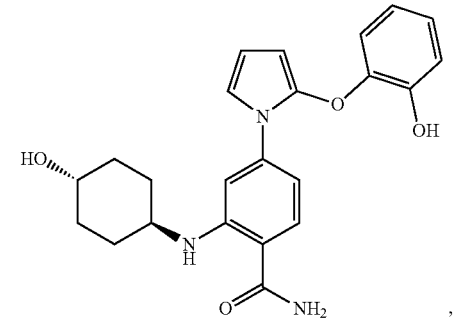
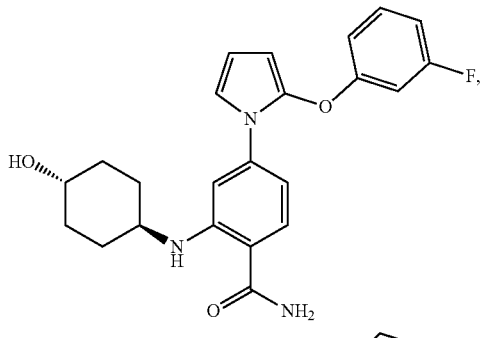
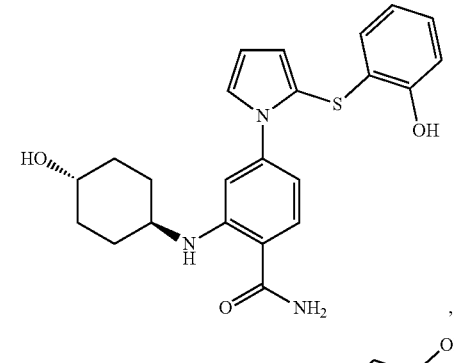
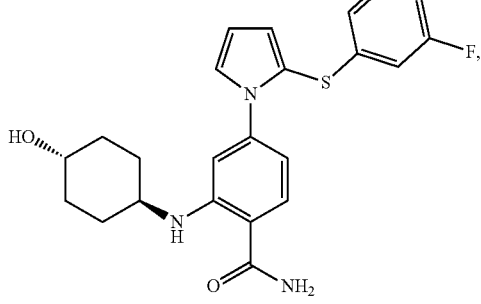
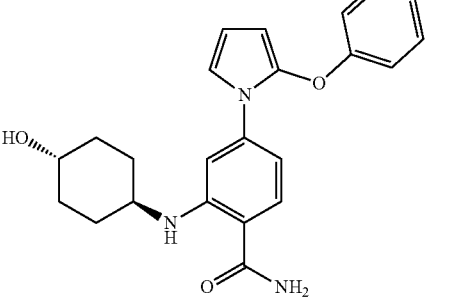

-continued
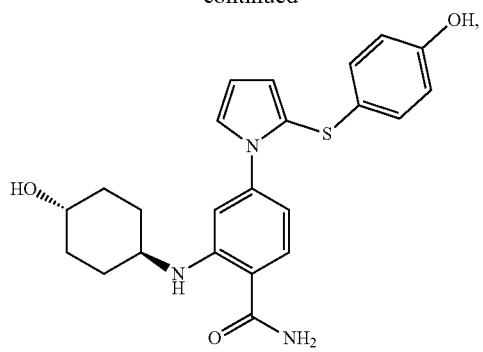
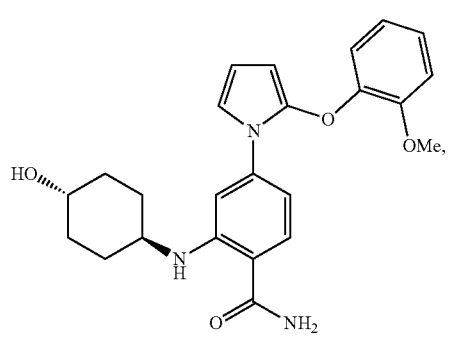
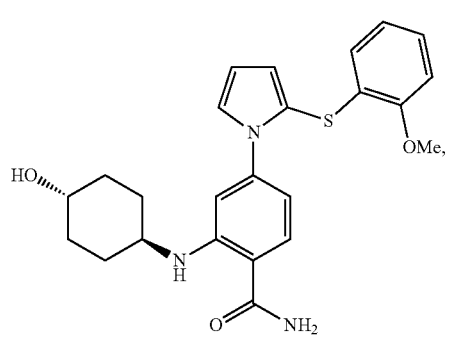
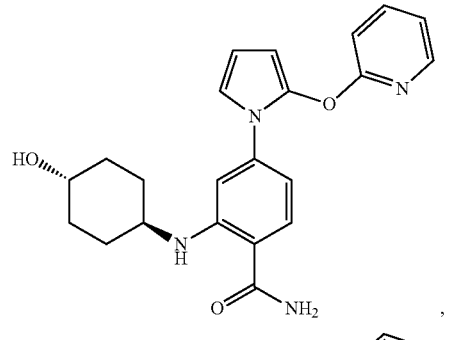
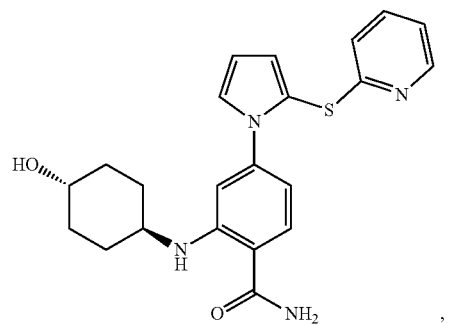
-continued
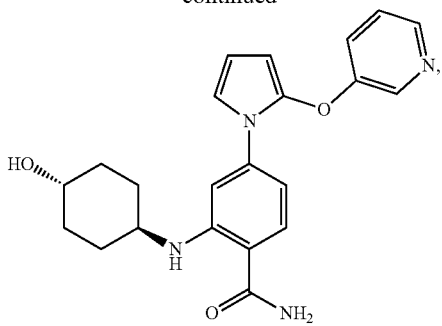
, and
Further examples are provided in the EXAMPLES section.
In an aspect, a compound represented by Formula III is provided

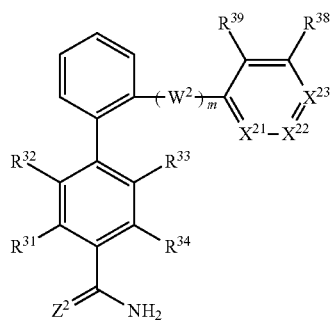

(III)

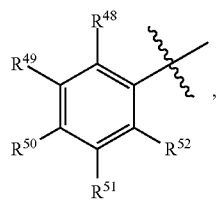

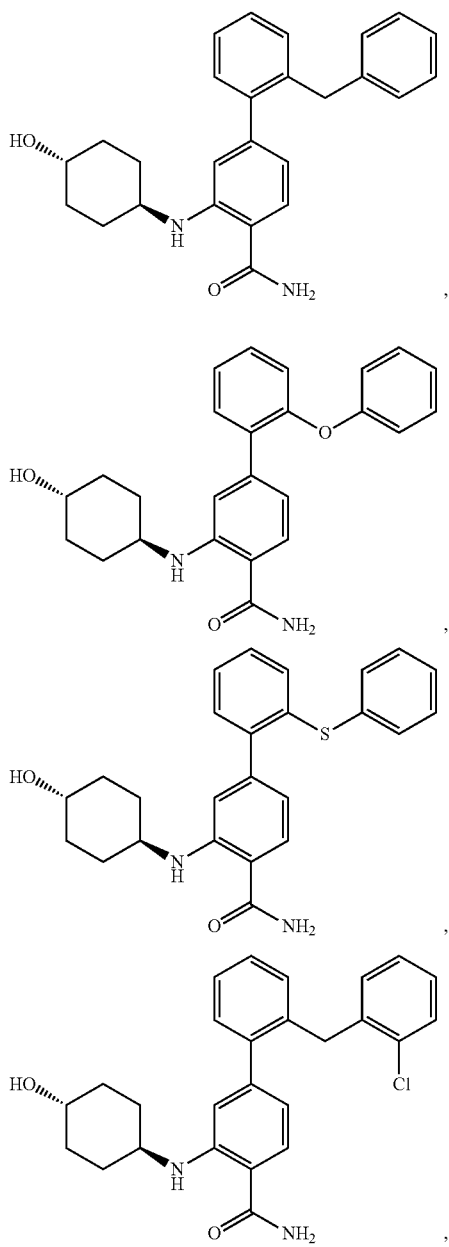

where $X^{25}$ and $X^{26}$ are each independently OH, amino, SH, sulfide, sulfoxide, or sulfone; and $R^{48}$, $R^{49}$, $R^{50}$, $R^{51}$ and $R^{52}$ are each independently H, alkyl, alkoxy, amino, halo, trifluoromethyl, or cyano.

Examples of compounds according to Formula III include, but are not limited to, or a pharmaceutically acceptable salt and/or solvate thereof, wherein $X^{21}$ is N or C—$R^{35}$; $X^{22}$ is N or C—$R^{36}$; $X^{23}$ is N or C—$R^{37}$; $W^2$ is C($R^{40}$)($R^{41}$), O, or S; $R^{31}$ is alkyl, cycloalkyl, aryl, heterocyclyl, or $X^{24}$—$R^{42}$; $R^{32}$, $R^{33}$, $R^{34}$, $R^{35}$, $R^{36}$, $R^{37}$, $R^{38}$, $R^{39}$, $R^{40}$, and $R^{41}$ are each independently H, OH, alkyl, alkoxy, aryloxy, heteroaryloxy, amino, halo, trifluoromethyl, or cyano; $X^{24}$ is O, S, or NH; $R^{42}$ is alkyl, cycloalkyl, aryl, or heterocyclyl; $Z^2$ is O, S, or NH; and m is 0 or 1.

In any embodiment herein, it may be that $R^{31}$ is $C_1$-$C_6$ alkyl, $C_3$-$C_6$ cycloalkyl, a substituted or unsubstituted phenyl, $C_2$-$C_5$ heterocyclyl, or $X^{24}$—$R^{42}$. In any embodiment herein, it may be that $R^{42}$ is $C_1$-$C_6$ alkyl, $C_3$-$C_6$ cycloalkyl, a substituted or unsubstituted phenyl, or $C_2$-$C_5$ heterocyclyl. In any embodiment herein, it may be that $R^{42}$ is $C_1$-$C_6$ alkyl, $C_3$-$C_6$ cycloalkyl, substituted or unsubstituted phenyl, or non-aromatic $C_2$-$C_5$ heterocyclyl.

In any embodiment herein, $R^{31}$ may be isopropyl, tert-butyl, cyclopropyl, cyclobutyl, cyclopentyl, cyclohexyl,

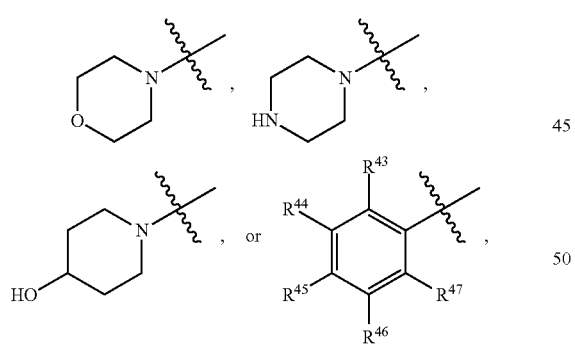

where $R^{43}$, $R^{44}$, $R^{45}$, $R^{46}$ and $R^{47}$ are each independently H, alkyl, alkoxy, amino, halo, trifluoromethyl, or cyano. $R^{42}$ in any embodiment herein may be isopropyl, tert-butyl, cyclopropyl, cyclobutyl, cyclopentyl, cyclohexyl,

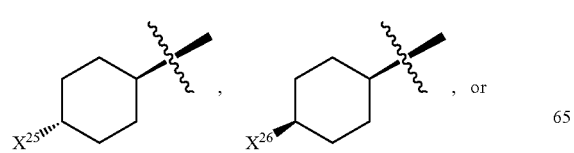

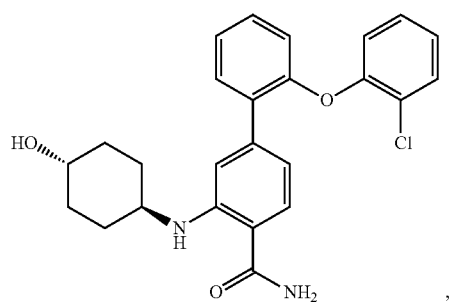
,
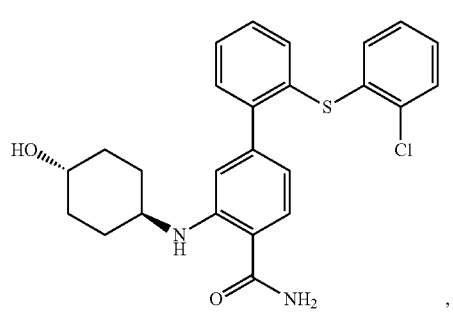
,
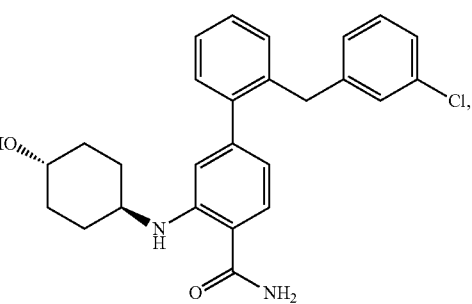
,
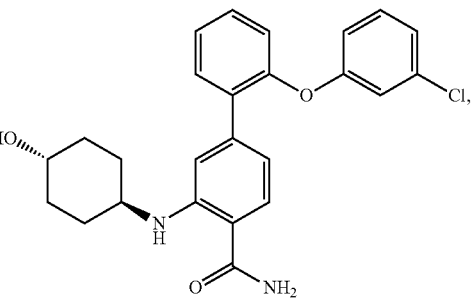
,
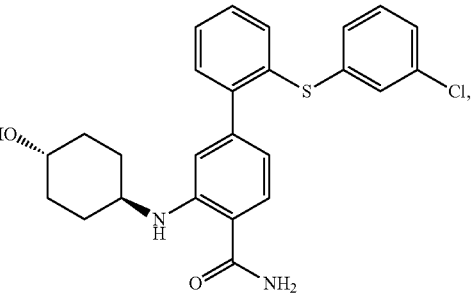
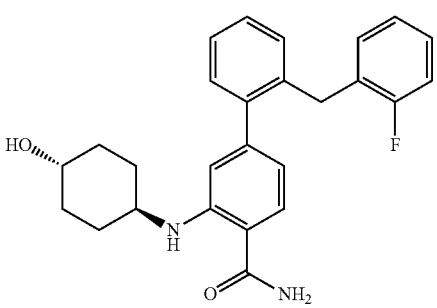
,
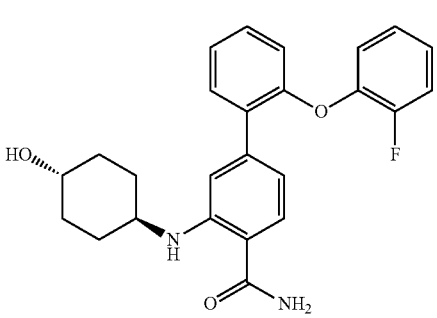
,
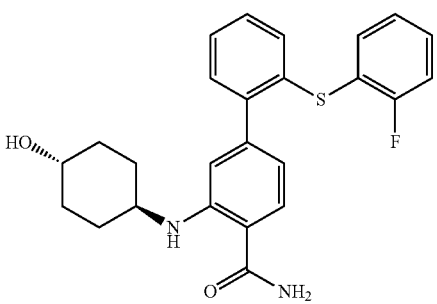
,
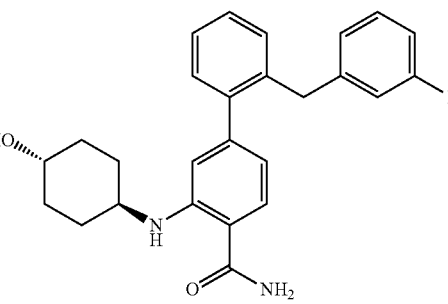
,
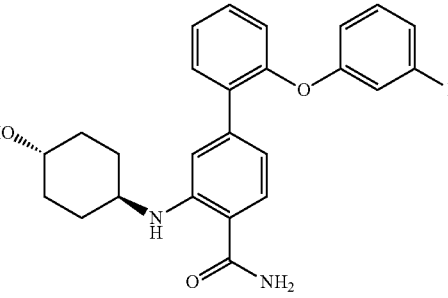

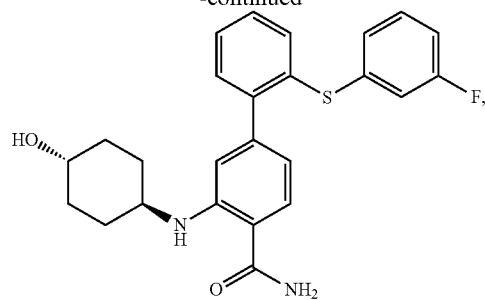
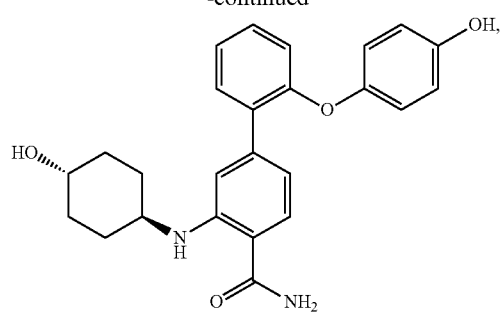
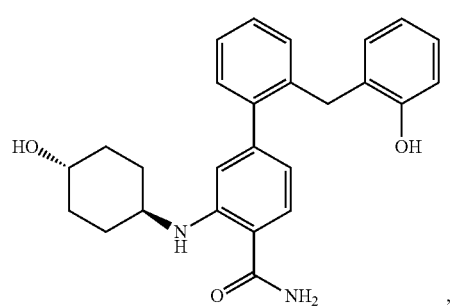
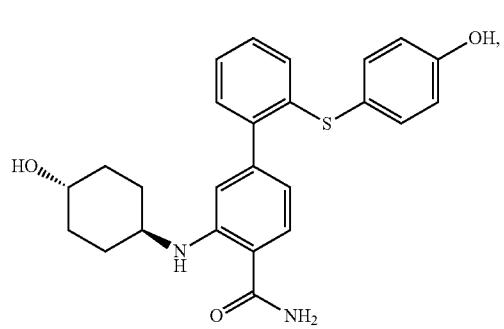
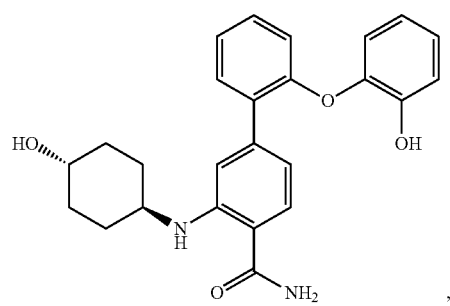
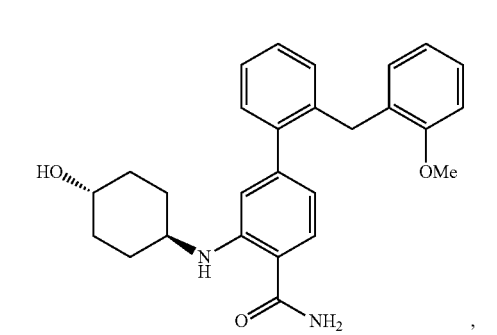
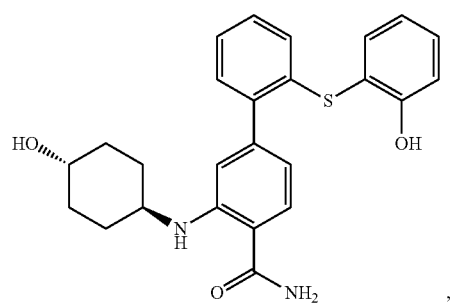
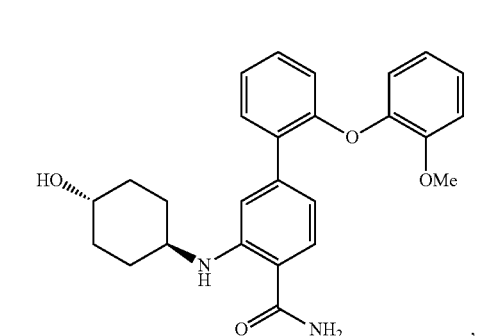
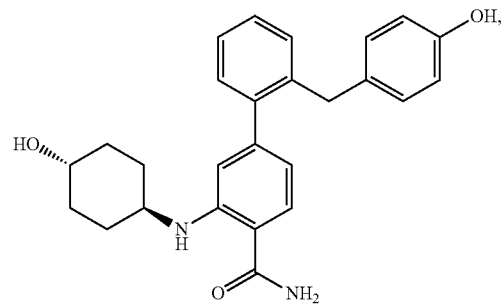
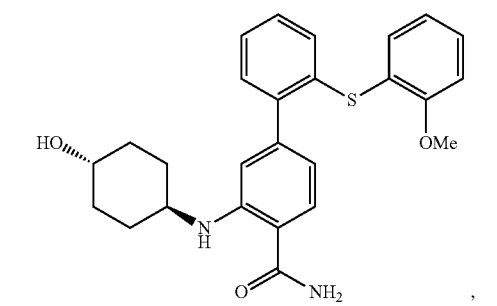

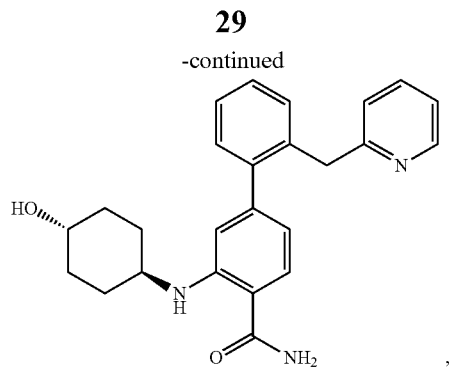
,
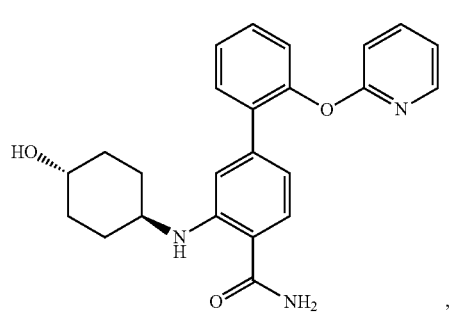
,
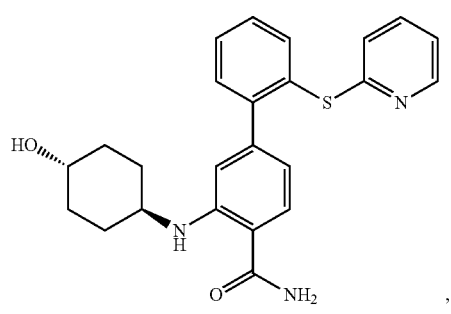
,
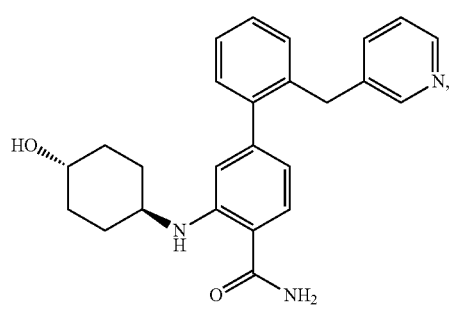
,
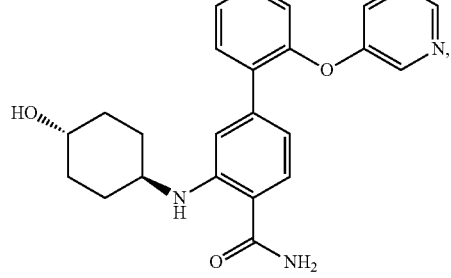
,
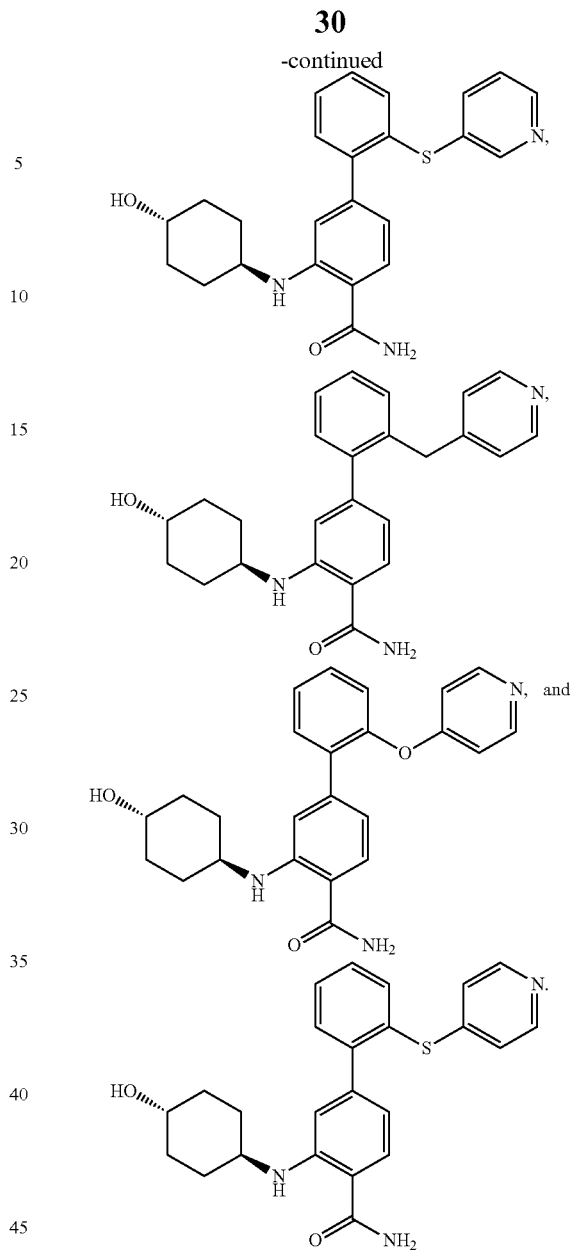

The present technology provides compositions (e.g., pharmaceutical compositions) and medicaments comprising any of one of the embodiments of the compounds of Formulas I-III (or a pharmaceutically acceptable salt thereof) disclosed herein and a pharmaceutically acceptable carrier or one or more excipients or fillers. The compositions may be used in the methods and treatments described herein. The pharmaceutical composition may include an effective amount of any of one of the embodiments of the compounds of the present technology disclosed herein. In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of cancer (such as multiple myeloma, breast cancer, or prostate cancer) and glaucoma (such as myocilin glaucoma).

Another example of an effective amount includes amounts or dosages that yield acceptable toxicity and bioavailability levels for therapeutic (pharmaceutical) use including, but not limited to, cancer (such as multiple myeloma, breast cancer, or prostate cancer) and glaucoma (such as myocilin glaucoma). Another example of an effective amount includes amounts or dosages that are capable of reducing symptoms associated with multiple myeloma, such as, for example, reduction in proliferation and/or metastasis of multiple myeloma. Another example of an effective amount includes amounts or dosages that are capable of reducing symptoms associated with glaucoma, such as, for example, a decrease in intraocular pressure ("IOP") The effective amount may be from about 0.01 µg to about 1 mg of the compound per gram of the composition, and preferably from about 0.1 µg to about 500 µg of the compound per gram of the composition. As used herein, a "subject" or "patient" is a mammal, such as a cat, dog, rodent or primate. Typically the subject is a human, and, preferably, a human suffering from or suspected of suffering from cancer (such as multiple myeloma, breast cancer, or prostate cancer) or glaucoma (such as myocilin glaucoma). The term "subject" and "patient" can be used interchangeably.

In any of the embodiments of the present technology described herein, the pharmaceutical composition may be packaged in unit dosage form. The unit dosage form is effective in treating cancer (such as multiple myeloma, breast cancer, or prostate cancer) or glaucoma (such as myocilin glaucoma). Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-4}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

The pharmaceutical compositions may be prepared by mixing one or more compounds of Formulas I-III, pharmaceutically acceptable salts thereof, stereoisomers thereof, tautomers thereof, or solvates thereof, with pharmaceutically acceptable carriers, excipients, binders, diluents or the like to prevent and treat disorders associated with cancer (such as multiple myeloma, breast cancer, or prostate cancer) and glaucoma (such as myocilin glaucoma). The compounds and compositions described herein may be used to prepare formulations and medicaments that treat cancer (such as multiple myeloma, breast cancer, or prostate cancer) and glaucoma (such as myocilin glaucoma). Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also include, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In an aspect, a method for inhibiting cell motility of a cancer cell is provided. The method includes contacting the cancer cell with a compound of any one of the above embodiments of compounds of Formulas I-III (or a pharmaceutically acceptable salt thereof), thereby inhibiting the cell motility of the cancer cell. The method may include contacting the cell with an effective amount of any one of the above embodiments of compounds of Formulas I-III (or a pharmaceutically acceptable salt thereof). In the method, the effective amount may include an amount effective in reducing cell motility of the cancer cell, e.g., as compared to cell motility of the cancer cell in the absence of the compound of the present technology and/or other motility-reducing compounds. For instance, the effective amount may include an amount effective in reducing cell motility of the cancer cell by at least about 50%, at least about 60%, at least about 70%, at least about 80%, at least about 90%, or at least about 95% as compared to cell motility of the cancer cell in the absence of the compound of the present technology and/or other motility-reducing compounds. The method may include inhibiting metastasis of the cancer cell. In any embodiment herein, the cancer cell may include a multiple myeloma cancer cell, a breast cancer cell, or prostate cancer cell. The contacting may or may not be within a patient and/or on a patient. For example, the contacting may occur in vitro. In any of the embodiments of the method, the contacting step may include administration of a pharmaceutical composition, where the pharmaceutical composition includes an effective amount of any one of the embodiments of the compounds of Formulas I-III (or a pharmaceutically acceptable salt thereof) and a pharmaceutically acceptable carrier. The effective amount may be from about 0.01 µg to about 1 mg of the compound per gram of the composition, and preferably from about 0.1 µg to about 500 µg of the compound per gram of the composition.

In an aspect, a method of inhibiting death of a cell exhibiting mutant myocilin is provided, the method including contacting the cell with any one of the above embodiments of the compounds of Formulas I-III (or a pharmaceutically acceptable salt thereof), thereby inhibiting the death of the cell. It may be the method includes contacting the cell with an effective amount of any one of the above embodiments of the compounds of Formulas I-III (or a pharmaceutically acceptable salt thereof). In the method, the effective amount may include an amount effective in inhibiting death of the cell, e.g., as compared to the cell in the absence of the compound of the present technology and/or other cell death-inhibiting compounds. For instance, the effective amount may include an amount effective in inhibiting death of a population of cells exhibiting mutant myocilin by at least about 50%, at least about 60%, at least about 70%, at least about 80%, at least about 90%, or at least about 95% as compared to a population of cells exhibiting mutant myocilin in the absence of the compound of the present technology and/or other cell death-inhibiting compounds. The contacting may or may not be within a patient and/or on a patient. For example, the contacting may occur in vitro. In any of the embodiments of the method, the contacting step may include administration of a pharmaceutical composition, where the pharmaceutical composition includes an effective amount of any one of the embodiments of the compounds of Formulas I-III (or a pharmaceutically acceptable salt thereof) and a pharmaceutically acceptable carrier. The effective amount may be from about 0.01 µg to about 1 mg of the compound per gram of the composition, and preferably from about 0.1 μg to about 500 μg of the compound per gram of the composition.

In an aspect, a method of treating a patient or animal suffering from cancer or glaucoma is provided, the method including administration of a compound of any one of the above embodiments of the present technology to the patient or animal. The method may include administration of an effective amount of any one of the embodiments of the compounds of Formulas I-III (or a pharmaceutically acceptable salt thereof). In the method, administration of the compound (e.g., an effective amount) of any one of the above embodiments of the present technology to the patient or animal treats the patient or animal suffering from the cancer or the glaucoma. In any embodiment herein, the cancer cell may include a multiple myeloma cancer cell, a breast cancer cell, or prostate cancer cell. In any embodiment herein, the glaucoma may be myocilin glaucoma. In any embodiment of the method, it may be that administration of the compound of any one of the above embodiments of the present technology treats the patient or animal suffering from the cancer or the glaucoma.

In any of the embodiments of the method of treating a patient or animal suffering from the cancer or the glaucoma, the method may include administration of a pharmaceutical composition, where the pharmaceutical composition includes an effective amount of any one of the embodiments of the compounds of the present technology or a pharmaceutically acceptable salt thereof and a pharmaceutically acceptable carrier. The effective amount may be from about 0.01 μg to about 1 mg of the compound per gram of the composition, and preferably from about 0.1 μg to about 500 μg of the compound per gram of the composition. In any of the embodiments of the method, the compound or composition may be administered orally, parenterally, rectally, or transdermally.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Exemplary Synthetic Procedures and Characterization

General Experimental Methods. $^1$H NMR were recorded at 400 or 500 MHz (Bruker DRX-400) spectrometer and $^{13}$C NMR spectra were recorded at 125 MHz (Bruker DRX 500 with broadband, inverse triple resonance, and high resolution magic angle spinning, HR-MA probe spectrometer); chemical shifts are reported in δ (ppm) relative to the internal chloroform-d (CDCl$_3$, 7.27 ppm). FAB (HRMS) spectra were recorded with a LCT Premier (Waters Corp., Milford, MA). Concentration of solutions after reactions and extractions involved the use of a rotary evaporator operating at reduced pressure. The purity of all compounds was determined to be >95% purity as determined by $^1$H NMR and $^{13}$C NMR spectra, unless otherwise noted. TLC was performed on glass backed silica gel plates (Uniplate) with spots visualized by UV light. All solvents were reagent grade.

Preparation of tert-butyl 2-bromo-1H-pyrrole-1-carboxylate (2)

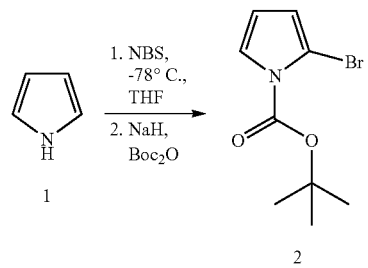

Pyrrole 1 (5 g, 74.6 mmol) was dissolved in 200 mL of tetrahydrofuran (THF) and cooled to −78° C. before N-bromosuccinimide (NBS) (13.2 g, 74.6 mmol) was added in portions. The resulting solution was stirred for 5 min before transferring to a freezer (−20° C.) for 2 h, during which time the solution turned light green. The solution was then filtered into a 500 mL flask previously cooled to −78° C. The flask was then flushed with argon, triethylamine (TEA) (9.5 g, 75 mmol) was added followed by of 4-dimethylaminopyridine (DMAP) (455 mg, 3.73 mmol) and di-tert-butyl dicarbonate (22.6 g, 104.2 mmol). This reaction mixture was warmed to rt and stirred for 8 h. Solvent was removed in vacuo and 150 mL of ethyl acetate was added to the residue. The ethyl acetate layer was washed with water (3×50 ml), dried over sodium sulfate, and was concentrated to give compound 2 as a colorless oil (14.9 g, 82%): $^1$H NMR (500 MHz, Chloroform-d) δ 7.33 (dd, J=3.6, 1.9 Hz, 1H), 6.32 (dd, J=3.5, 2.0 Hz, 1H), 6.18 (t, J=3.5 Hz, 1H), 1.64 (s, 9H). $^{13}$C NMR (126 MHz, CDCl3) δ 148.06, 123.00, 117.23, 111.58, 100.29, 84.83, 27.99 (3). HRMS (ESI) m/z [M+Na] for C$_9$H$_{12}$BrNO$_2$Na: 267.9943; found, 267.9949.

General Procedure for the Preparation of 3a-j:

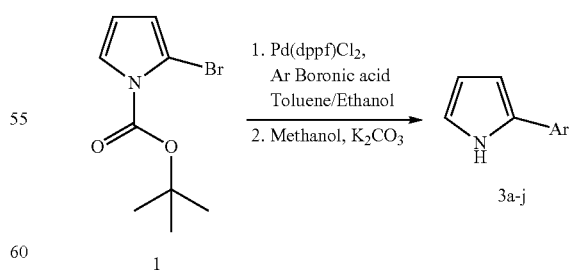

Compound 2 (200 mg, 0.81 mmol), aryl boronic acid (0.88 mmol), and potassium carbonate (331 mg, 2.4 mmol) were added to a 15 mL sealed tube, followed by addition of toluene (3 mL), ethanol (0.5 mL) and water (0.5 mL). Argon was purged through the solvent for 15 min and then Pd(dppf)

Cl₂ (30 mg, 0.04 mmol) was added. The reaction vessel was sealed and heated to 110° C. for 12 h. Upon cooling to rt, the solvents was removed under vacuum. Water (5 mL) and ethyl acetate (5 mL) were added to the residue and the organic fraction was filtered through a plug of silica and dried in vacuo. The resulting residue was dissolved in 3 mL of methanol and 1 mL of water mixture along with potassium carbonate (331 mg, 2.4 mmol). The reaction was refluxed for 12 h. The reaction vessel was cooled and the solvent evaporated under vacuum until ¼$^{th}$ of the volume remained. 2 mL of water was then added and extracted with ethyl acetate (3×10 mL). The organic layers were combined and dried over sodium sulfate and concentrated; the residue was then purified via column chromatography (SiO₂) with 20% ethyl acetate in hexanes to produce products as amorphous solids.

2-phenyl-1H-pyrrole (3a)

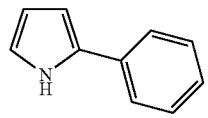

77% yield, light orange amorphous solid. ¹H NMR (400 MHz, Chloroform-d) δ 8.46 (s, 1H), 7.54-7.48 (m, 2H), 7.39 (dd, J=8.5, 7.0 Hz, 2H), 7.27-7.21 (m, 1H), 6.90 (m, J=2.7, 1.4 Hz, 1H), 6.56 (m, J=3.8, 2.7, 1.5 Hz, 1H), 6.33 (m, J=3.4, 2.5 Hz, 1H).). ¹³C NMR (126 MHz, CDCl₃) δ 132.76, 132.13, 128.91, 126.23, 123.86, 118.86, 110.13, 105.96. HRMS (ESI) m/z [M+H] for C₁₀H₁₀N: 144.0813, found 144.0818.

2-(o-tolyl)-1H-pyrrole (3b)

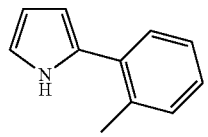

83% yield, white amorphous solid. ¹H NMR (500 MHz, CDCl₃) δ 8.20 (s, 1H), 7.28 (dd, J=7.5, 1.6 Hz, 1H), 7.20-7.17 (m, 2H), 7.16-7.10 (m, 2H), 6.81 (m, J=2.7, 1.5 Hz, 1H), 6.33-6.19 (m, 2H), 2.39 (s, 3H). ¹³C NMR (126 MHz, CDCl₃) δ 135.10, 132.85, 131.32, 131.04, 127.91, 126.79, 126.05, 117.92, 109.24, 108.78, 21.27. HRMS (ESI) m/z [M+H] for C₁₁H₁₂N: 158.0970, found 158.0965.

2-(m-tolyl)-1H-pyrrole (3c)

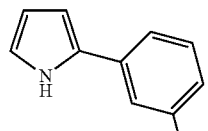

77% yield, white amorphous solid. ¹H NMR (500 MHz, CDCl₃) δ 8.35 (s, 1H), 7.23 (m, 1H), 7.21-7.17 (m, 2H), 6.96 (m, 1H), 6.79 (m, 1H), 6.44 (m, 1H), 6.22 (m, 1H), 2.31 (d, J=0.7 Hz, 3H). ¹³C NMR (126 MHz, CDCl₃) δ 138.46, 132.70, 132.25, 128.78, 127.03, 124.64, 120.98, 118.63, 110.05, 105.82, 21.55. HRMS (ESI) m/z [M+H] for C₁₁H₁₂N: 158.0970, found 158.0965.

2-(p-tolyl)-1H-pyrrole (3d)

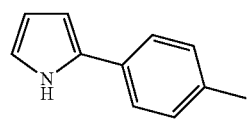

73% yield, white amorphous solid. ¹H NMR (500 MHz, CDCl₃) δ 8.32 (s, 1H), 7.30 (m, 2H), 7.13-7.09 (m, 2H), 6.78 (m, 1H), 6.41 (m, 1H), 6.22 (m, 1H), 2.28 (s, 3H). ¹³C NMR (126 MHz, CDCl₃) δ 135.93, 132.28, 130.04, 129.55 (2), 123.84 (2), 118.38, 109.99, 105.38, 21.13. HRMS (ESI) m/z [M+Na] for C₁₁H₁₁NNa: 180.0789, found 180.0788.

2-(2-chlorophenyl)-1H-pyrrole (3e)

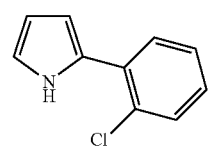

84% yield, white amorphous solid. ¹H NMR (500 MHz, CDCl₃) δ 9.03 (s, 1H), 7.50 (dd, J=7.8, 1.8 Hz, 1H), 7.33 (dd, J=8.0, 1.5 Hz, 1H), 7.23-7.19 (m, 1H), 7.14-7.04 (m, 1H), 6.90-6.85 (m, 1H), 6.54 (m, 1H), 6.25 (m, 1H). ¹³C NMR (126 MHz, CDCl₃) δ 131.02, 130.74, 129.78, 129.34, 129.17, 127.31, 127.18, 119.00, 109.39, 109.31. HRMS (ESI) m/z [M+H] for C₁₀H₉ClN: 178.0424, found 178.0429.

2-(3-chlorophenyl)-1H-pyrrole (3f)

80% yield, white amorphous solid. ¹H NMR (500 MHz, CDCl₃) δ 8.35 (s, 1H), 7.38 (t, J=1.9 Hz, 1H), 7.27 (m, 1H), 7.22 (t, J=7.8 Hz, 1H), 7.10 (m, 1H), 6.82 (m, 1H), 6.47 (m, 1H), 6.24 (m, 1H). ¹³C NMR (126 MHz, CDCl₃) δ 134.82, 134.48, 130.69, 130.14, 126.05, 123.82, 121.82, 119.50, 110.40, 106.92. HRMS (ESI) m/z [M+H] for C₁₀H₉ClN: 178.0424, found 178.0429.

2-(4-chlorophenyl)-1H-pyrrole (3 g)

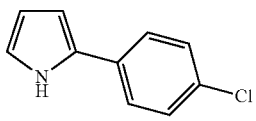

78% yield, white amorphous solid. $^1$H NMR (500 MHz, CDCl$_3$) δ 8.32 (s, 1H), 7.34-7.30 (m, 2H), 7.28-7.24 (m, 2H), 6.81 (m, 1H), 6.44 (m, 1H), 6.23 (m, 1H). $^{13}$C NMR (126 MHz, CDCl$_3$) δ 131.74, 131.26, 131.01, 129.04 (2), 125.00 (2), 119.22, 110.35, 106.42. HRMS (ESI) m/z [M+H] for C$_{10}$H$_9$ClN: 178.0424, found 178.0421.

2-(1H-pyrrol-2-yl)pyridine (3h)

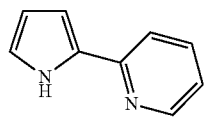

65% yield, White amorphous solid. $^1$H NMR (400 MHz, CDCl$_3$) δ 9.82 (s, 1H), 8.55-8.44 (m, 1H), 7.72-7.54 (m, 2H), 7.06 (m, 1H), 6.94 (m, 1H), 6.75 (m, 1H), 6.32 (m, 1H). $^{13}$C NMR (126 MHz, CDCl$_3$) δ 150.31, 148.46, 136.74, 131.18, 120.48, 120.12, 118.24, 110.32, 107.44. HRMS (ESI) m/z [M+H] for C$_9$H$_9$N$_2$: 145.0766, found 145.0762.

3-(1H-pyrrol-2-yl) pyridine (3i)

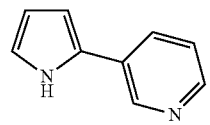

74% yield, white amorphous solid. $^1$H NMR (500 MHz, CDCl$_3$) δ 9.02-8.86 (m, 1H), 8.72 (dd, 7=2.4, 0.9 Hz, 1H), 8.35 (dd, J=4.8, 1.6 Hz, 1H), 7.71 (m, 1H), 7.22 (m, 1H), 6.87 (m, 1H), 6.53 (m, 1H), 6.31 (m, 1H). $^{13}$C NMR (126 MHz, CDCl$_3$) δ 146.90, 145.11, 136.28, 131.11, 128.88, 123.78, 120.12, 110.45, 107.27. HRMS (ESI) m/z [M+H] for C$_9$H$_9$N$_2$: 145.0766, found 145.0762.

4-(1H-pyrrol-2-yl) pyridine (3j)

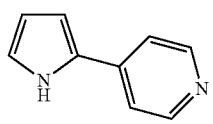

73% yield, white amorphous solid. $^1$H NMR (500 MHz, CDCl$_3$) δ 8.72 (s, 1H), 8.55-8.41 (m, 2H), 7.33-7.23 (m, 2H), 6.91 (m, 1H), 6.69 (m, 1H), 6.28 (m, 1H). $^{13}$C NMR (126 MHz, CDCl$_3$) δ 149.92, 139.61, 129.01, 121.24, 117.70, 111.00, 109.21. HRMS (ESI) m/z [M+H] for C$_9$H$_9$N$_2$: 145.0766, found 145.0768.

Preparation of 11a-c

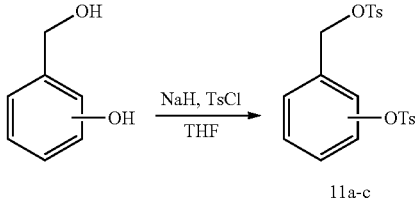

Sodium hydride (37 mmol) was added in portions to a solution of benzyl alcohol (16.1 mmol) in 50 mL THF at 0° C. The reaction was stirred at 0° C. for 20 minutes, and p-toluenesulfonyl chloride (35.42 mmol) was added as a solution in 20 ml THF. The reaction was stirred overnight at rt, then 50 ml water and 50 ml ethyl acetate were added. The organic layer was washed with brine and dried over sodium sulfate. A quick column chromatography was performed using 20% ethyl acetate in hexanes as eluent.

2-(tosyloxy)benzyl 4-methylbenzenesulfonate (11a)

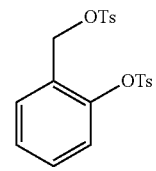

92% yield, pale yellow oil. $^1$H NMR (500 MHz, CDCl$_3$) δ 7.81-7.76 (m, 2H), 7.71-7.67 (m, 2H), 7.38-7.33 (m, 5H), 7.30 (dd, J=7.6, 1.9 Hz, 1H), 7.25 (td, J=7.5, 1.5 Hz, 1H), 7.06 (dd, J=8.0, 1.4 Hz, 1H), 4.91 (s, 2H), 2.48 (d, J=5.1 Hz, 6H). $^{13}$C NMR (126 MHz, CDCl$_3$) δ 147.17, 145.94, 144.95, 132.81, 132.08, 130.28, 130.13 (2), 130.00 (2), 129.89, 128.42, 127.99, 127.33 (2), 127.31 (2), 122.59, 66.04, 21.80, 21.70. HRMS (ESI) m/z [M+H] for C$_{21}$H$_{21}$O$_6$S$_2$: 433.0779, found 433.0770.

3-(tosyloxy)benzyl 4-methylbenzenesulfonate (11b)

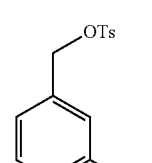

80% yield, pale yellow oil. $^1$H NMR (500 MHz, CDCl$_3$) δ 7.81-7.77 (m, 2H), 7.72-7.68 (m, 2H), 7.39-7.32 (m, 5H), 7.26 (d, J=8.0 Hz, 1H), 7.19-7.15 (m, 1H), 6.96 (m, 1H), 6.89 (t, J=2.0 Hz, 1H), 4.97 (s, 2H), 2.48 (d, J=2.4 Hz, 7H). $^{13}$C NMR (126 MHz, CDCl$_3$) δ 149.62, 145.69, 145.12, 135.35, 132.88, 132.08, 129.96 (2), 129.91 (2), 129.86, 128.48, 127.95 (2), 126.89 (2), 122.94, 122.32, 70.53, 21.77, 21.70. HRMS (ESI) m/z [M+H] for C$_{21}$H$_{21}$O$_6$S$_2$: 433.0779, found 433.0765.

4-(tosyloxy)benzyl 4-methylbenzenesulfonate (11c)

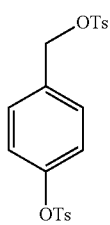

11c

94% yield, pale yellow oil. $^1$H NMR (500 MHz, CDCl$_3$) δ 7.72-7.69 (m, 2H), 7.63-7.59 (m, 2H), 7.29-7.22 (m, 4H), 7.13-7.09 (m, 2H), 6.88-6.85 (m, 2H), 4.93 (s, 2H), 2.38 (s, J=3.9, 1.1 Hz, 6H). $^{13}$C NMR (126 MHz, CDCl$_3$) δ 149.91, 145.57, 145.09, 132.98 (2), 132.34 (2), 132.17 (2), 129.92 (2), 129.85 (2) 129.78 (2), 128.49, 127.94, 122.68, 70.73, 21.76, 21.69. HRMS (ESI) m/z [M+H] for C$_{21}$H$_{21}$O$_6$S$_2$: 433.0779, found 433.0770.

Phenethyl 4-methylbenzenesulfonate (13)

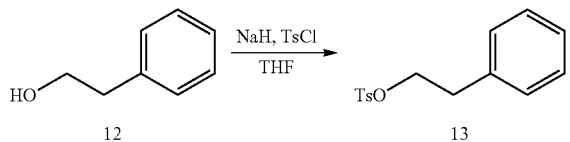

Phenyl ethyl alcohol (16.1 mmol) was dissolved in 50 mL THF, cooled to 0° C. and sodium hydride (16.1 mmol) was added slowly while stirring. The reaction was stirred at 0° C. for 20 minutes followed by addition of p-toluenesulfonyl chloride (17 mmol) as a solution in 20 ml THF. The reaction was stirred overnight at rt, then 50 ml water and 50 ml ethyl acetate were added. The organic layer was washed with brine and dried over sodium sulfate. A quick column chromatography was performed using 20% ethyl acetate in hexanes as eluent. 4 g, yellow solid, 90% yield. $^1$H NMR (500 MHz, CDCl$_3$) δ 7.74-7.68 (m, 2H), 7.32-7.22 (m, 7H), 7.17-7.10 (m, 2H), 4.23 (t, J=7.1 Hz, 2H), 2.98 (t, J=7.1 Hz, 2H), 2.46 (s, 3H). $^{13}$C NMR (126 MHz, CDCl$_3$) δ 144.65, 136.19, 132.93 (2), 129.78 (2), 128.91, 128.60 (2), 127.84, 126.88 (2), 70.61, 35.35, 21.65. HRMS (ESI) m/z [M+Na] for C$_{15}$H$_{16}$O$_3$SNa: 299.0718, found 299.0730.

Preparation of Intermediates 6a-r$^{40}$:

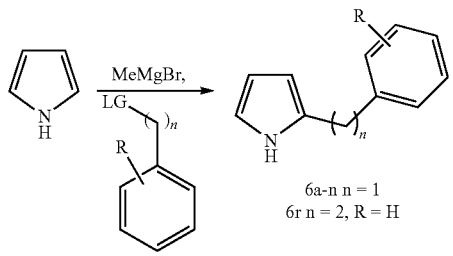

6a-n n = 1
6r n = 2, R = H

Methyl magnesium bromide (4.5 mmol, 3N solution in diethyl ether) was added dropwise to a round bottom flask containing pyrrole (4.47 mmol) in 5 mL solvent mixture of THF:dichloromethane (1:1) at 0° C. Followed quickly by the addition of the corresponding substituted benzyl bromide/tosylate 11a-c, 13 (4.4 mmol) as a solution in 2 ml THF. The reaction was stirred at rt overnight and quenched with 50 mL saturated solution of ammonium chloride before extracting with ethyl acetate. The combined organic extracts were dried over sodium sulfate and concentrated. Column chromatography (SiO$_2$) was performed using 15% ethyl acetate in hexanes as eluent to yield the product as amorphous solids.

2-benzyl-1H-pyrrole (6a)

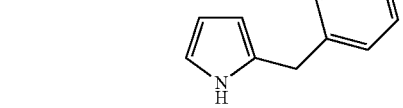

49% yield, white amorphous solid. $^1$H NMR (500 MHz, CDCl$_3$) δ 7.86-7.65 (s, 1H), 7.26-7.21 (m, 2H), 7.18-7.11 (m, 3H), 6.60 (m, 1H), 6.08 (q, J=2.9 Hz, 1H), 5.93 (m, 1H), 3.92 (s, 2H). $^{13}$C NMR (126 MHz, CDCl$_3$) δ 139.47, 128.69 (2), 128.62 (2), 128.53, 126.43, 116.96, 108.37, 106.46, 34.09. HRMS (ESI) m/z [M+H] for C$_{11}$H$_{12}$N: 158.0970, found 158.0965.

6b-d, h were used as crude for further reaction.

2-(2-fluorobenzyl)-1H-pyrrole (6e)

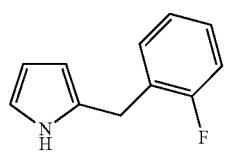

40% yield, white amorphous solid. $^1$H NMR (500 MHz, CDCl$_3$) δ 7.94 (s, 1H), 7.16-7.06 (m, 2H), 7.03-6.91 (m, 3H), 6.61 (td, J=2.7, 1.5 Hz, 1H), 6.06 (d, J=2.8 Hz, 1H), 5.97-5.90 (m, 1H), 3.96-3.90 (m, 2H). $^{13}$C NMR (126 MHz, CDCl$_3$) δ 159.86, 130.76, 128.23, 128.16, 124.34, 117.12, 115.42, 115.25, 108.39, 106.48, 27.31. HRMS (ESI) m/z [M+H] for C$_{11}$H$_{11}$N: 176.0876, found 176.0880.

2-(3-fluorobenzyl)-1H-pyrrole (6f)

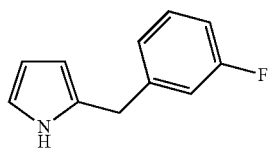

42% yield, white solid. $^1$H NMR (500 MHz, CDCl$_3$) δ 7.77 (s, 1H), 7.18-7.10 (m, 3H), 6.93-6.86 (m, 2H), 6.62 (m, 1H), 6.09 (q, J=2.9 Hz, 1H), 5.81 (d, J=2.7 Hz, 1H), 3.83 (s, 2H). $^{13}$C NMR (126 MHz, CDCl$_3$) δ 164.01, 163.98, 142.28, 129.97, 124.17, 124.14, 115.56, 113.38, 108.50, 107.05, 33.88. HRMS (ESI) m/z [M+H] for C$_{11}$H$_{11}$FN: 176.0876, found 176.0872.

2-(4-fluorobenzyl)-1H-pyrrole (6 g)

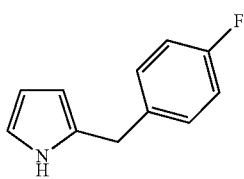

40% yield, white amorphous solid. $^1$H NMR (500 MHz, CDCl$_3$) δ 7.75 (s, 1H), 7.14-7.05 (m, 2H), 6.95-6.85 (m, 3H), 6.61 (d, J=2.4 Hz, 1H), 6.08 (q, J=2.7 Hz, 1H), 5.91 (d, J=3.1 Hz, 1H), 3.88 (s, 2H). $^{13}$C NMR (126 MHz, CDCl$_3$) δ 160.62, 135.14, 135.11, 118.13, 117.11, 115.02, 114.85, 108.86, 108.46, 106.58, 32.56. HRMS (ESI) m/z [M+H] for C$_{11}$H$_{11}$FN: 176.0876, found 176.0875.

2-(2-methylbenzyl)-1H-pyrrole (6i)

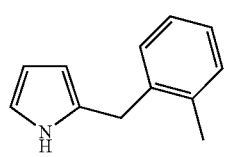

46% yield, white amorphous solid. $^1$H NMR (500 MHz, Chloroform-d) δ 7.35-7.31 (m, 1H), 7.08 (m, 3H), 6.98 (m, 1H), 6.78 (dd, J=2.9, 1.8 Hz, 1H), 6.46-6.40 (m, 2H), 6.19 (t, J=3.2 Hz, 1H), 5.87 (m, 1H), 3.80 (s, 2H), 2.12 (s, 3H). $^{13}$C NMR (126 MHz, CDCl$_3$) δ 136.00, 130.08, 129.49, 128.86, 126.45, 126.13, 121.44, 110.05, 108.71, 69.74, 30.69, 19.44. HRMS (ESI) m/z [M+Na] for C$_{12}$H$_{13}$NNa: 194.0946, found 194.091.

2-((1H-pyrrol-2-yl)methyl)phenyl 4-methylbenzenesulfonate (6j)

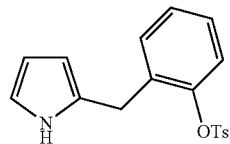

24% yield, white amorphous solid. $^1$H NMR (500 MHz, CDCl$_3$) δ 8.36 (s, 1H), 7.82-7.78 (m, 2H), 7.38-7.35 (m, 2H), 7.20-7.14 (m, 2H), 7.12-7.08 (m, 2H), 6.89 (dd, J=8.0, 1.3 Hz, 1H), 6.67 (m, 1H), 6.11 (q, J=2.9 Hz, 1H), 6.02 (m, 1H), 3.89 (s, 2H), 2.48 (s, 3H). $^{13}$C NMR (126 MHz, CDCl$_3$) δ 147.15, 145.72, 133.86, 132.78, 131.28, 129.98 (2), 128.50 (2), 127.89, 127.49, 127.48, 122.21, 117.49, 107.92, 106.92, 27.70, 21.79. HRMS (ESI) m/z [M+H] for C$_{18}$H$_{17}$NO$_3$S: 327.0929 found 327.0935.

3-((1H-pyrrol-2-yl)methyl)phenyl 4-methylbenzenesulfonate (6k)

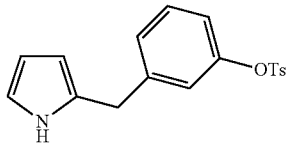

27% yield, white amorphous solid. $^1$H NMR (500 MHz, CDCl$_3$) δ 7.71-7.57 (m, 3H), 7.24-7.20 (m, 2H), 7.14 (t, J=7.9 Hz, 1H), 7.01 (m, 1H), 6.81-6.77 (m, 1H), 6.74 (dd, J=2.4, 1.4 Hz, 1H), 6.59 (m, 1H), 6.05 (q, J=2.9 Hz, 1H), 5.80 (m, 1H), 3.83 (s, 2H), 2.38 (s, 3H). $^{13}$C NMR (126 MHz, CDCl$_3$) δ 149.79, 145.31, 141.64, 132.39, 129.76, 129.74 (2), 129.69, 128.50 (2), 127.36, 122.55, 120.38, 117.24, 108.46, 106.80, 33.70, 21.76. HRMS (ESI) m/z [M+H] for C$_{18}$H$_{17}$NO$_3$S: 327.0929 found 327.0935.

4-((1H-pyrrol-2-yl)methyl)phenyl 4-methylbenzenesulfonate (6l)

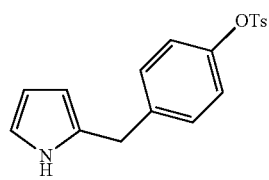

25% yield, white amorphous solid. $^1$H NMR (500 MHz, CDCl$_3$) δ 7.75 (s, 1H), 7.64 (m, 2H), 7.27-7.21 (m, 2H), 7.05-7.01 (m, 2H), 6.85-6.82 (m, 2H), 6.62 (m, 1H), 6.07 (q, J=2.9 Hz, 1H), 5.88 (m, 1H), 3.87 (s, 2H), 2.38 (s, 3H). $^{13}$C NMR (126 MHz, CDCl$_3$) δ 148.14, 145.32, 138.59, 132.47, 129.85, 129.76, 129.73, 128.80, 128.53, 128.50, 128.04, 122.49, 122.46, 117.26, 108.46, 106.83, 33.42, 21.75. HRMS (ESI) m/z [M+H] for C$_{18}$H$_{17}$NO$_3$S: 327.0929 found 327.0935.

2-(2-methoxybenzyl)-1H-pyrrole (6m)

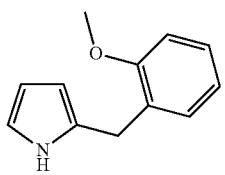

42% yield, white amorphous solid. $^1$H NMR (500 MHz, CDCl$_3$) δ 8.21 (s, 1H), 7.22-7.08 (m, 2H), 6.93-6.81 (m, 2H), 6.65 (m, 1H), 6.14-6.06 (m, 1H), 5.99 (t, J=3.0 Hz, 1H), 3.91 (s, 2H), 3.85 (s, 3H). $^{13}$C NMR (126 MHz, CDCl$_3$) δ 157.02, 130.27, 129.76, 128.89, 127.68, 120.99, 116.57, 110.61, 107.99, 105.60, 55.46, 28.83. HRMS (ESI) m/z [M+H] for C$_{12}$H$_{14}$NO: 188.1075, found 188.1074.

2-(2,6-difluorobenzyl)-1H-pyrrole (6n)

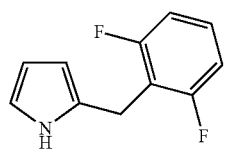

43% yield, white amorphous solid. $^1$H NMR (500 MHz, CDCl$_3$) δ 7.95 (s, 1H), 7.19-7.08 (m, 2H), 6.94-6.79 (m, 3H), 6.55 (t, J=2.8 Hz, 1H), 5.95 (t, J=3.0 Hz, 1H), 4.08 (d, J=1.5 Hz, 2H). $^{13}$C NMR (126 MHz, CDCl$_3$) δ 169.72 (2), 135.78, 132.40, 129.34, 121.32, 116.21, 111.30 (2), 110.99, 33.06. HRMS (ESI) m/z [M+H] for C$_{11}$H$_{11}$F$_2$N: 194.0781, found 194.0785.

2-((1H-pyrrol-2-yl)methyl)pyridine (6o)

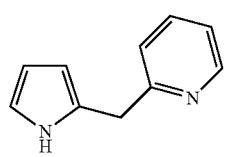

36% yield, white amorphous solid. $^1$H NMR (400 MHz, CDCl$_3$) δ 9.1-8.96 (s, 1H), 8.57 (d, J=4.9 Hz, 1H), 7.68 (t, J=7.7 Hz, 1H), 7.27-7.18 (m, 2H), 6.75 (m, 1H), 6.14 (d, J=2.9 Hz, 1H), 6.06 (s, 1H), 4.17 (s, 2H). $^{13}$C NMR (126 MHz, CDCl$_3$) δ 136.73, 133.11, 132.56, 125.40, 125.12, 121.81, 121.70, 119.91, 109.13, 35.14. HRMS (ESI) m/z [M+H] for C$_{10}$H$_{11}$N$_2$: 159.0947, found 159.0922.

3-((1H-pyrrol-2-yl)methyl)pyridine (6p)

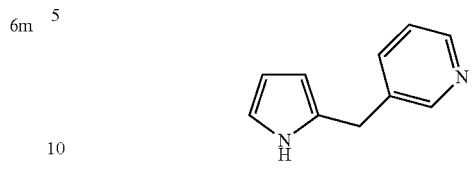

43% yield, white amorphous solid. $^1$H NMR (500 MHz, CDCl$_3$) δ 8.44-8.40 (m, 2H), 7.88 (s, 1H), 7.48-7.40 (m, 1H), 7.17 (m, 1H), 6.64 (m, 1H), 6.09 (q, J=2.9 Hz, 1H), 5.91 (m, 1H), 3.92 (s, 2H). $^{13}$C NMR (126 MHz, CDCl$_3$) δ 149.77, 147.90, 136.32, 135.09, 129.29, 123.58, 117.50, 108.60, 107.04, 31.33. HRMS (ESI) m/z [M+H] for C$_{10}$H$_{11}$N$_2$: 159.0947, found 159.0922.

4-((1H-pyrrol-2-yl)methyl)pyridine (6q)

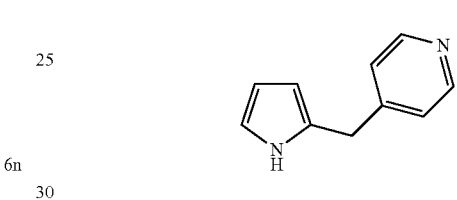

40% yield, white amorphous solid. $^1$H NMR (500 MHz, CDCl$_3$) δ 8.46-8.41 (m, 2H), 7.88 (s, 1H), 7.06 (m, 2H), 6.66 (m, 1H), 6.10 (q, J=2.9 Hz, 1H), 5.95 (m, 1H), 3.92 (s, 2H). $^{13}$C NMR (126 MHz, CDCl$_3$) δ 149.80 (2), 149.79, 148.91, 123.93 (2), 117.64, 108.68, 107.46, 33.49. HRMS (ESI) m/z [M+H] for C$_{10}$H$_{11}$N$_2$: 159.0947, found 159.0936.

2-phenethyl-1H-pyrrole (6r)

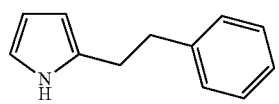

42% yield, colorless oil. $^1$H NMR (500 MHz, CDCl$_3$) δ 7.78 (s, 1H), 7.35-7.16 (m, 5H), 6.69-6.62 (m, 1H), 6.15 (p, J=3.1 Hz, 1H), 5.98 (m, 1H), 3.00-2.82 (m, 5H). $^{13}$C NMR (126 MHz, CDCl$_3$) δ 141.60, 128.51, 128.47, 128.44, 128.42, 128.28, 126.12, 116.26, 108.23, 105.26, 36.15, 29.62. HRMS (ESI) m/z [M+Na] for C$_{12}$H$_{13}$NNa: 194.0946, found 194.0941.

General Procedure for Preparation of 4a-j, 7a-r:

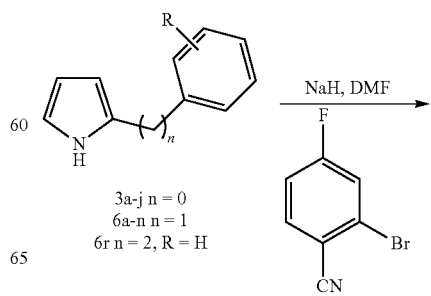

47

-continued

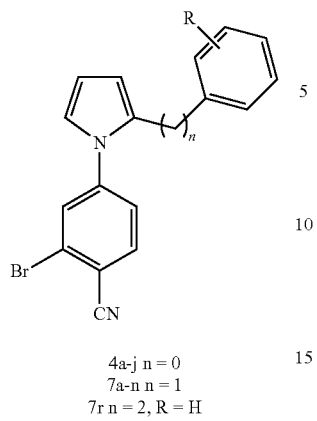

4a-j n = 0
7a-n n = 1
7r n = 2, R = H

Pyrrole intermediates 3a-j, or 7a-p or 7s (0.7 mmol) and 2-bromo-4-fluorobenzonitrile (0.7 mmol) were dissolved in 0.5 mL of dry dimethyl formamide (DMF) in a round bottom flask. Sodium hydride (60% dispersion in oil) (0.7 mmol) was then added into the stirring reaction mixture under argon. After 4 h 10 mL of water was added to the reaction mixture and extracted using ethyl acetate (2×15 mL). The organic layers was washed with brine and dried over sodium sulfate followed by concentration, column chromatography (SiO$_2$) was performed utilizing 20% ethyl acetate in hexanes to obtain products as amorphous solids.

2-bromo-4-(2-phenyl-1H-pyrrol-1-yl) benzonitrile (4a)

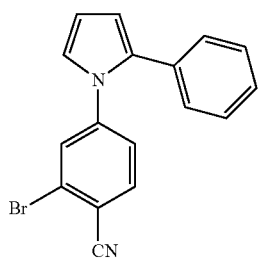

4a

84% yield, beige colored amorphous solid. $^1$H NMR (400 MHz, CDCl$_3$) δ 7.58-7.54 (m, 2H), 7.38-7.28 (m, 3H), 7.16-7.09 (m, 3H), 6.98 (dd, J=3.0, 1.7 Hz, 1H), 6.48 (dd, J=3.5, 1.7 Hz, 1H), 6.44 (dd, J=3.5, 2.9 Hz, 1H). $^{13}$C NMR (126 MHz, CDCl$_3$) δ 144.64, 134.51, 133.97, 131.93, 129.01 (2), 128.56, 128.50, 127.26 (2), 125.74, 124.31, 123.70, 116.83, 113.04, 112.82, 111.22. HRMS (ESI) m/z [M+H] for C$_{17}$H$_{12}$BrN$_2$: 323.0183, found 323.0174.

48

2-bromo-4-(2-(o-tolyl)-1H-pyrrol-1-yl)benzonitrile (4b)

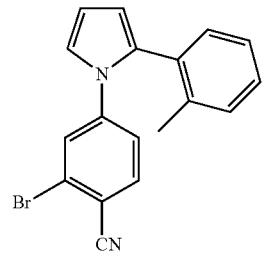

4b

85% yield, pale yellow amorphous solid. $^1$H NMR (500 MHz, CDCl$_3$) δ 7.45 (d, J=8.5 Hz, 1H), 7.42 (d, J=2.1 Hz, 1H), 7.27-7.23 (m, 1H), 7.20-7.15 (m, 3H), 7.01-6.95 (m, 2H), 6.44 (t, J=3.3 Hz, 1H), 6.33 (m, 1H), 1.99 (s, 3H). $^{13}$C NMR (126 MHz, CDCl$_3$) δ 144.61, 137.21, 134.46, 132.96, 132.05, 131.05, 130.48, 128.46, 127.79, 125.97, 125.60, 122.71, 121.67, 116.86, 113.21, 112.42, 110.98, 20.14. HRMS (ESI) m/z [M+Na] for C$_{18}$H$_{13}$BrN$_2$Na: 359.0160, found 359.0165.

2-bromo-4-(2-(m-tolyl)-1H-pyrrol-1-yl)benzonitrile (4c)

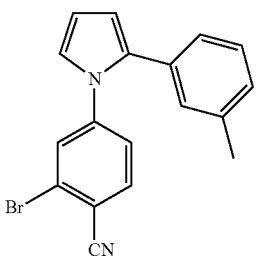

4c

82% yield, pale yellow amorphous solid. $^1$H NMR (500 MHz, CDCl$_3$) δ 7.55-7.52 (m, 2H), 7.15 (t, J=7.6 Hz, 1H), 7.09-7.06 (m, 2H), 7.02 (m, 1H), 6.94 (m, 1H), 6.85-6.82 (m, 1H), 6.44 (m, 1H), 6.41 (m, 1H), 2.31 (s, 3H). $^{13}$C NMR (126 MHz, CDCl$_3$) δ 144.71, 138.31, 134.45, 134.44, 131.85, 129.14, 129.14, 128.89, 128.35, 128.06, 125.70, 124.30, 123.54, 116.90, 112.90, 112.72, 111.18, 21.45. HRMS (ESI) m/z [M+Na] for C$_{18}$H$_{13}$BrN$_2$Na: 359.0160, found 359.0175.

2-bromo-4-(2-(p-tolyl)-1H-pyrroyl-1-yl)benzonitrile (4d)

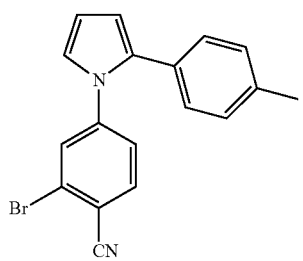

4d

86% yield, pale yellow amorphous solid. ¹H NMR (500 MHz, Chloroform-d) δ 7.75-7.64 (m, 1H), 7.60-7.37 (m, 2H), 7.24 (m, 1H), 7.15-7.06 (m, 2H), 7.05-6.87 (m, 2H), 6.43 (d, J=6.5 Hz, 2H), 2.37 (s, 3H). ¹³C NMR (126 MHz, CDCl₃) δ 144.82, 137.25, 136.10, 134.51, 129.28, 129.05 (2), 128.95, 128.42, 125.74 (2), 124.43, 123.42, 115.82, 112.93, 112.43, 111.15, 21.11. HRMS (ESI) m/z [M+H] for C₁₈H₁₄BrN₂: 337.0340, found 337.0334.

2-bromo-4-(2-(2-chlorophenyl)-1H-pyrrol-1-yl)benzonitrile (4e)

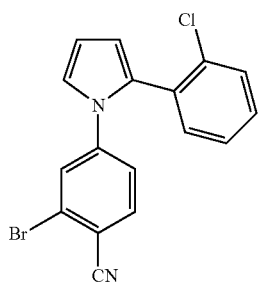

74% yield, light yellow amorphous solid. ¹H NMR (500 MHz, CDCl₃) δ 7.49 (d, J=8.4 Hz, 1H), 7.43 (d, J=2.1 Hz, 1H), 7.36-7.27 (m, 4H), 7.05-7.01 (m, 2H), 6.47-6.43 (m, 2H). ¹³C NMR (126 MHz, CDCl₃) δ 144.59, 134.53, 134.08, 132.42, 131.49, 130.55, 130.03, 129.68, 128.05, 126.98, 125.63, 122.85, 122.51, 116.84, 114.15, 112.79, 110.98. HRMS (ESI) m/z [M+H] for C₁₇H₁₁BrClN₂: 356.9794, found 356.9803.

2-bromo-4-(2-(3-chlorophenyl)-1H-pyrrol-1-yl)benzonitrile (4f)

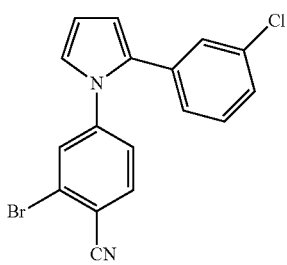

86% yield, pale yellow amorphous solid. ¹H NMR (500 MHz, CDCl₃) δ 7.59-7.52 (m, 2H), 7.25-7.15 (m, 3H), 7.09 (dd, J=8.4, 2.1 Hz, 1H), 6.96 (dd, J=3.0, 1.7 Hz, 1H), 6.89-6.86 (m, 1H), 6.48 (dd, J=3.6, 1.7 Hz, 1H), 6.42 (dd, J=3.6, 2.9 Hz, 1H). ¹³C NMR (126 MHz, CDCl₃) δ 144.27, 134.66, 134.50, 133.69, 132.38, 129.69, 129.01, 128.21, 127.26, 126.51, 125.94, 124.39, 124.33, 116.73, 113.58, 113.42, 111.39. HRMS (ESI) m/z [M+Na] for C₁₇H₁₁BrClN₂: 378.9614, found 378.9616.

2-bromo-4-(2-(4-chlorophenyl)-1H-pyrrol-1-yl)benzonitrile (4 g)

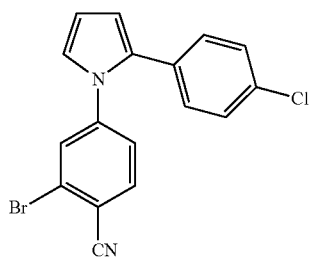

88% yield, pale yellow amorphous solid. ¹H NMR (500 MHz, CDCl₃) δ 7.50 (d, J=8.4 Hz, 1H), 7.48 (d, J=2.1 Hz, 1H), 7.34-7.24 (m, 1H), 7.20 (d, J=1.9 Hz, 1H), 7.19 (s, 1H), 7.02-6.96 (m, 3H), 6.88 (m, 1H), 6.38 (m, 1H), 6.35 (m, 1H). ¹³C NMR (126 MHz, CDCl₃) δ 144.37, 134.65, 130.39, 129.55 (2), 129.03, 128.82 (2), 125.95, 125.00, 124.38, 124.16, 116.69, 113.39, 113.18, 111.34, 110.34.
HRMS (ESI) m/z [M+H] for C₁₇H₁₁BrClN₂: 356.9794, found 356.9803.

2-bromo-4-(2-(2-chlorophenyl)-1H-pyrrol-1-yl)benzonitrile (4h)

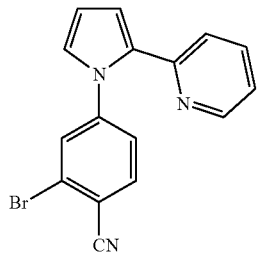

75% yield, amorphous white solid. ¹H NMR (500 MHz, CDCl₃) δ 8.36-8.27 (m, 1H), 7.60 (m, 1H), 7.55-7.44 (m, 2H), 7.32 (d, J=7.9 Hz, 1H), 7.12-7.02 (m, 2H), 6.90 (m, 1H), 6.70 (s, 1H), 6.36 (m, 1H). ¹³C NMR (126 MHz, CDCl₃) δ 150.55, 148.86, 145.31, 136.71, 134.29, 134.04, 129.39, 125.81, 125.48, 124.55, 122.18, 121.39, 116.95, 114.77, 113.18, 111.21. HRMS (ESI) m/z [M+H] for C₁₆H₁₁BrN₃: 324.0136, found 324.0133.

2-bromo-4-(2-(pyridin-3-yl)-1H-pyrrol-1-yl)benzonitrile (4i)

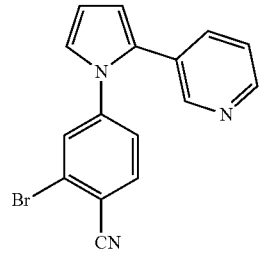

65% yield, amorphous white solid. $^1$H NMR (400 MHz, CDCl$_3$) δ 8.56-8.49 (m, 2H), 7.62 (m, 1H), 7.56 (d, J=2.1 Hz, 1H), 7.43-7.36 (m, 1H), 7.25 (m, 1H), 7.13 (m, 1H), 7.03 (m, 1H), 6.57 (m, 1H), 6.49 (m, 1H). $^{13}$C NMR (126 MHz, CDCl$_3$) δ 148.31, 147.47, 144.00, 135.77, 134.90, 129.90, 129.31, 128.31, 126.23, 125.10, 124.41, 123.43, 116.52, 114.09, 113.93, 111.66. HRMS (ESI) m/z [M+Na] for C$_{16}$H$_{10}$BrN$_3$Na: 345.9956, found 345.9948.

2-bromo-4-(2-(pyridin-4-yl)-1H-pyrrol-1-yl)benzonitrile (4j)

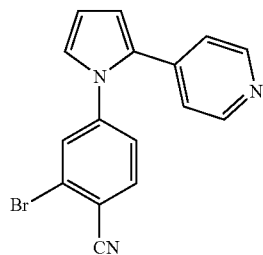

4j

66% yield, amorphous white solid. $^1$H NMR (500 MHz, CDCl$_3$) δ 8.48-8.39 (m, 2H), 7.59-7.48 (m, 2H), 7.07 (dd, J=8.4, 2.1 Hz, 1H), 6.96-6.89 (m, 3H), 6.60 (dd, J=3.7, 1.6 Hz, 1H), 6.39 (dd, J=3.7, 2.9 Hz, 1H). $^{13}$C NMR (126 MHz, CDCl$_3$) δ 149.78 (2), 144.03, 139.35, 134.90, 130.91, 129.25, 126.30, 126.23, 124.52, 122.01 (2), 116.52, 115.22, 114.15, 111.82. HRMS (ESI) m/z [M+H] for C$_{16}$H$_{11}$BrN$_3$: 324.0136, found 324.0133.

4-(2-benzyl-1H-pyrrol-1-yl)-2-bromobenzonitrile (7a)

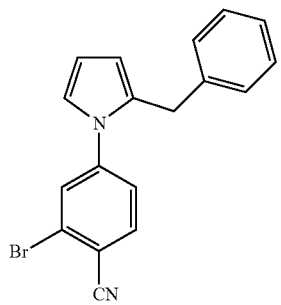

7a

81% yield, white amorphous solid. $^1$H NMR (400 MHz, CDCl$_3$) δ 7.65 (dd, J=8.3, 1.6 Hz, 1H), 7.52 (t, J=1.8 Hz, 1H), 7.34-7.15 (m, 4H), 7.12-6.99 (m, 2H), 6.80 (m, 1H), 6.32 (t, J=3.2 Hz, 1H), 6.16 (dd, J=3.5, 1.8 Hz, 1H), 3.96 (s, 2H). $^{13}$C NMR (126 MHz, CDCl$_3$) δ 149.06, 135.23, 128.86 (2), 126.67, 126.35 (2), 125.04, 122.75, 117.96, 112.33, 110.91, 109.13, 103.84, 102.96, 99.40, 98.31, 20.88. HRMS (ESI) m/z [M+H] for C$_{18}$H$_{13}$BrN$_2$: 337.0340, found 337.0336.

2-bromo-4-(2-(2-chlorobenzyl)-1H-pyrrol-1-yl)benzonitrile (7b)

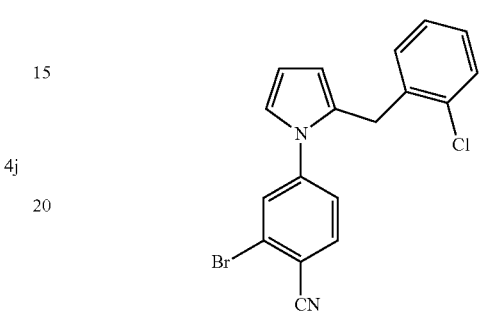

7b

71% yield, white amorphous solid. $^1$H NMR (500 MHz, Chloroform-d) δ 7.58 (d, J=8.3 Hz, 1H), 7.46 (d, J=2.0 Hz, 1H), 7.28-7.24 (m, 2H), 7.09 (dd, J=5.8, 3.5 Hz, 2H), 6.89 (s, 1H), 6.73 (dd, J=3.0, 1.8 Hz, 1H), 6.23 (t, J=3.2 Hz, 1H), 5.99 (m, 1H), 3.96 (s, 2H). $^{13}$C NMR (126 MHz, CDCl$_3$) δ 141.62, 138.52, 135.63, 134.79, 130.22, 129.72, 129.53, 128.04, 127.00, 126.27, 124.26, 115.03, 110.25, 103.91, 103.01, 98.95, 89.06, 29.71. HRMS (ESI) m/z [M+H] for C$_{18}$H$_{13}$BrClN$_2$: 370.9951, found 370.9966.

2-bromo-4-(2-(3-chlorobenzyl)-1H-pyrrol-1-yl)benzonitrile (7c)

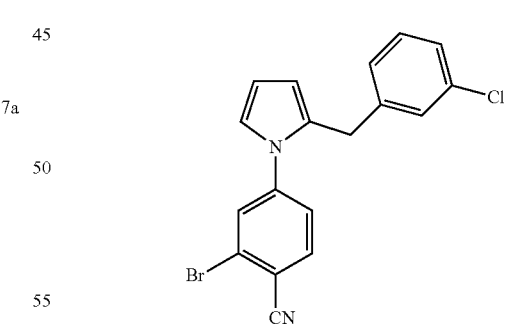

7c

76% yield, beige amorphous solid. $^1$H NMR (500 MHz, CDCl$_3$) δ 7.58 (d, J=8.3 Hz, 1H), 7.42 (d, J=2.1 Hz, 1H), 7.15 (dd, J=8.3, 2.1 Hz, 1H), 7.12-7.08 (m, 2H), 6.95 (m, 1H), 6.87-6.81 (m, 1H), 6.71 (dd, J=3.0, 1.7 Hz, 1H), 6.23 (t, J=3.2 Hz, 1H), 6.08 (m, 1H), 3.84 (s, 2H). $^{13}$C NMR (126 MHz, CDCl$_3$) δ 144.40, 140.97, 137.99, 134.73, 132.84, 130.04, 129.78, 128.61, 128.51, 126.76, 126.52, 124.55, 122.07, 116.65, 111.93, 110.19, 100.38, 32.81. HRMS (ESI) m/z [M+Na] for C$_{18}$H$_{12}$BrClN$_2$Na: 392.9770, found 392.9771.

2-bromo-4-(2-(4-chlorobenzyl)-1H-pyrrol-1-yl)benzonitrile (7d)

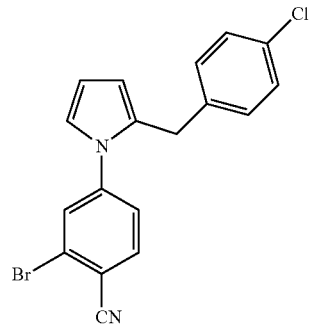

70% yield, beige amorphous solid. $^1$H NMR (500 MHz, CDCl$_3$) δ 7.58 (d, J=8.3 Hz, 1H), 7.43 (d, J=2.0 Hz, 1H), 7.18-7.12 (m, 3H), 6.92-6.89 (m, 2H), 6.71 (dd, J=3.0, 1.7 Hz, 1H), 6.22 (t, J=3.2 Hz, 1H), 6.04 (ddt, J=3.4, 1.6, 0.8 Hz, 1H), 3.83 (s, 2H). $^{13}$C NMR (126 MHz, CDCl$_3$) δ 144.43, 137.38, 134.75, 132.33, 131.33 (2), 129.95, 129.68, 128.68 (2), 125.84, 124.48, 122.02, 116.66, 113.89, 111.80, 110.16, 32.56. HRMS (ESI) m/z [M+H] for C$_{18}$H$_{13}$BrClN$_2$: 370.9951, found 370.9946.

2-bromo-4-(2-(2-fluorobenzyl)-1H-pyrrol-1-yl)benzonitrile (7e)

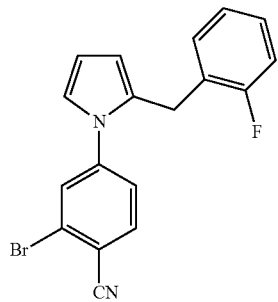

81% yield, beige amorphous solid. $^1$H NMR (500 MHz, CDCl$_3$) δ 7.59 (d, J=8.3 Hz, 1H), 7.47 (d, J=2.0 Hz, 1H), 7.21 (dd, J=8.3, 2.1 Hz, 1H), 7.15-7.07 (m, 1H), 6.97-6.86 (m, 3H), 6.71 (dd, J=3.0, 1.8 Hz, 1H), 6.21 (t, J=3.2 Hz, 1H), 6.03 (m, 1H), 3.88 (s, 2H). $^{13}$C NMR (126 MHz, CDCl$_3$) δ 161.37, 144.46, 134.76, 130.60, 130.43, 129.91, 128.41, 125.86, 124.46, 124.13, 121.92, 116.73, 115.39, 113.87, 111.68, 110.13, 25.87, 25.84. HRMS (ESI) m/z [M+H] for C$_{18}$H$_{13}$BrFN$_2$: 355.0246, found 355.0202.

2-bromo-4-(2-(3-fluorobenzyl)-1H-pyrrol-1-yl)benzonitrile (7f)

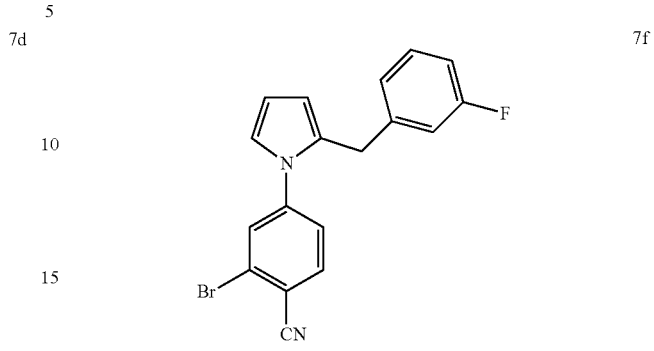

75% yield, beige amorphous solid. $^1$H NMR (500 MHz, CDCl$_3$) δ 7.57 (d, J=8.4 Hz, 1H), 7.42 (d, J=2.0 Hz, 1H), 7.18-7.10 (m, 2H), 6.82 (m, 3H), 6.74-6.69 (m, 1H), 6.24 (t, J=3.2 Hz, 1H), 6.08 (m, 1H), 3.87 (s, 2H). $^{13}$C NMR (126 MHz, CDCl$_3$) δ 163.97, 144.42, 134.73, 129.96, 125.82, 124.47, 123.95, 122.04, 116.66, 115.33, 115.16, 113.88, 113.58, 113.42, 111.96, 110.19, 109.02, 32.83. HRMS (ESI) m/z [M+Na] for C$_{18}$H$_{12}$BrFN$_2$Na: 377.0066, found 377.0114.

2-bromo-4-(2-(4-fluorobenzyl)-1H-pyrrol-1-yl)benzonitrile (7 g)

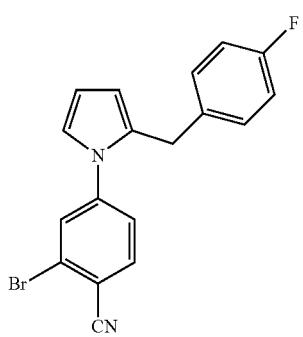

71% yield, white amorphous solid. $^1$H NMR (500 MHz, CDCl$_3$) δ 7.57 (d, J=8.3 Hz, 1H), 7.43 (d, J=2.0 Hz, 1H), 7.16 (dd, J=8.3, 2.0 Hz, 1H), 6.95-6.83 (m, 4H), 6.71 (dd, J=3.0, 1.8 Hz, 1H), 6.22 (t, J=3.2 Hz, 1H), 6.04 (m, 1H), 3.83 (s, 2H). $^{13}$C NMR (126 MHz, CDCl$_3$) δ 162.49, 144.50, 134.72, 134.52, 131.75 (2), 129.94, 129.81, 125.80, 124.47, 121.96, 116.68, 115.29 (2), 113.82, 111.70, 110.12, 32.41. HRMS (ESI) m/z [M+H] for C$_{18}$H$_{13}$BrFN$_2$: 355.0246, found 355.0202.

2-bromo-4-(2-(2-bromobenzyl)-1H-pyrrol-1-yl)benzonitrile (7h)

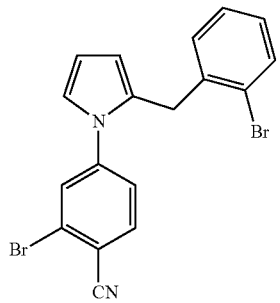

72% yield, white amorphous solid. ¹H NMR (500 MHz, CDCl₃) δ 7.58 (d, J=8.3 Hz, 1H), 7.48-7.45 (m, 1H), 7.40-7.37 (m, 1H), 7.16-7.07 (m, 2H), 7.03-6.96 (m, 2H), 6.74 (dd, J=3.0, 1.7 Hz, 1H), 6.23 (t, J=3.2 Hz, 1H), 5.98 (m, 1H), 3.96 (s, 2H). ¹³C NMR (126 MHz, CDCl₃) δ 144.43, 138.37, 135.97, 134.81, 132.86, 130.30, 129.70, 128.29, 127.56, 124.23, 121.86, 121.34, 121.13, 115.78, 115.60, 112.02, 110.28, 33.38. HRMS (ESI) m/z [M+Na] for $C_{18}H_{12}Br_2N_2Na$: 436.9228, found 436.9265.

2-bromo-4-(2-(2-methylbenzyl)-1H-pyrrol-1-yl)benzonitrile (7i)

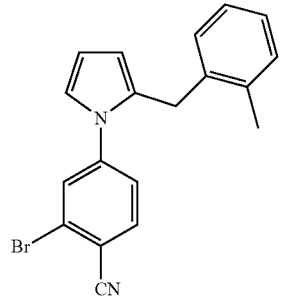

76% yield, beige amorphous solid. ¹H NMR (400 MHz, CDCl₃) δ 7.69-7.66 (m, 1H), 7.57 (q, J=4.4, 3.2 Hz, 1H), 7.17-7.11 (m, 4H), 6.99 (d, J=7.1 Hz, 1H), 6.85-6.77 (m, 1H), 6.31 (t, J=3.6 Hz, 1H), 5.99 (s, 1H), 3.89 (s, 2H), 2.19 (d, J=2.4 Hz, 3H). ¹³C NMR (126 MHz, CDCl₃) δ 144.63, 137.17, 135.87, 134.75, 131.48, 130.30, 129.57, 128.86, 126.72, 126.15, 124.15, 121.55, 116.75, 115.60, 113.61, 111.74, 110.26, 30.80, 19.43. HRMS (ESI) m/z [M+H] for $C_{19}H_{16}BrN_2$: 351.0483, found 351.0497.

2-((1-(3-bromo-4-cyanophenyl)-1H-pyrrol-2-yl)methyl)phenyl 4-methylbenzenesulfonate (7j)

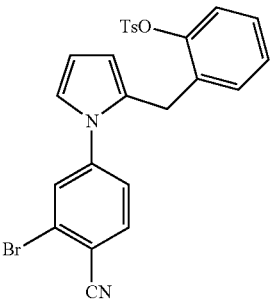

81% yield, white amorphous solid. ¹H NMR (500 MHz, CDCl₃) δ 7.64-7.58 (m, 2H), 7.54 (d, J=8.3 Hz, 1H), 7.36 (d, J=2.0 Hz, 1H), 7.28-7.21 (m, 2H), 7.13 (dd, J=8.3, 2.1 Hz, 1H), 7.09-7.02 (m, 2H), 6.96-6.90 (m, 1H), 6.82-6.78 (m, 1H), 6.69 (dd, J=3.0, 1.7 Hz, 1H), 6.20 (t, J=3.2 Hz, 1H), 5.95 (m, 1H), 3.78 (s, 2H), 2.40 (s, 3H). ¹³C NMR (126 MHz, CDCl₃) δ 147.41, 145.55, 144.30, 134.79, 132.90, 132.74, 130.49, 130.35, 129.88 (2), 129.73, 128.33 (2), 127.85, 127.19, 125.80, 124.37, 122.22, 121.89, 116.75, 113.75, 112.00, 110.16, 27.18, 21.79. HRMS (ESI) m/z [M+H] for $C_{25}H_{20}BrN_2O_3S$: 507.0372, found 507.0378.

3-((1-(3-bromo-4-cyanophenyl)-1H-pyrrol-2-yl)methyl)phenyl 4-methylbenzenesulfonate (7k)

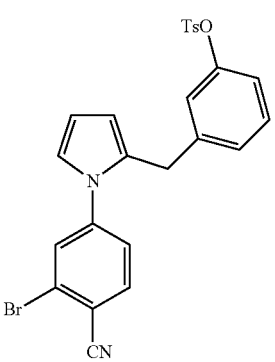

82% yield, white amorphous solid. ¹H NMR (500 MHz, CDCl₃) δ 7.68-7.62 (m, 4H), 7.43 (d, 7=2.1 Hz, 1H), 7.31-7.26 (m, 3H), 7.20 (dd, J=8.3, 2.0 Hz, 1H), 7.14 (t, J=7.9 Hz, 1H), 6.92 (m, 1H), 6.78-6.76 (m, 1H), 6.28 (t, J=3.2 Hz, 1H), 6.03 (m, 1H), 3.88 (d, J=1.0 Hz, 2H), 2.43 (s, 3H). ¹³C NMR (126 MHz, CDCl₃) δ 149.81, 145.30, 144.32, 141.14, 134.77, 129.88 (2), 129.75, 129.58, 128.55, 128.51, 128.47, 128.45 (2), 126.99, 124.52, 122.45, 122.06, 120.33, 116.66, 113.90, 111.98, 110.16, 32.73, 21.75. HRMS (ESI) m/z [M+H] for $C_{25}H_{20}BrN_2O_3S$: 507.0372, found 507.0362.

4-((1-(3-bromo-4-cyanophenyl)-1H-pyrrol-2-yl)methyl)phenyl 4-methylbenzenesulfonate (7l)

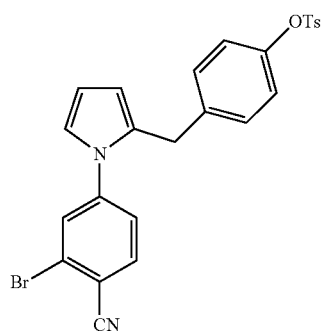

71% yield, white amorphous solid. $^1$H NMR (500 MHz, CDCl$_3$) δ 7.69-7.65 (m, 2H), 7.60 (d, J=8.3 Hz, 1H), 7.44 (d, J=2.1 Hz, 1H), 7.31-7.27 (m, 2H), 7.16 (dd, J=8.3, 2.1 Hz, 1H), 6.95-6.90 (m, 2H), 6.86-6.82 (m, 2H), 6.75 (dd, J=3.0, 1.7 Hz, 1H), 6.26 (t, J=3.2 Hz, 1H), 6.06 (m, 1H), 3.87 (s, 2H), 2.43 (s, 3H). $^{13}$C NMR (126 MHz, CDCl$_3$) δ 148.15, 145.39, 144.38, 137.94, 134.74, 132.43, 131.17 (2), 129.87 (2), 129.76, 129.45, 128.48 (2), 125.79, 124.46, 122.49, 122.04 (2), 116.63, 113.85, 111.88, 110.16, 32.55, 21.76. HRMS (ESI) m/z [M+Na] for C$_{25}$H$_{19}$BrN$_2$O$_3$SNa: 529.0197, found 529.0177.

2-bromo-4-(2-(2-methoxybenzyl)-1H-pyrrol-1-yl)benzonitrile (7m)

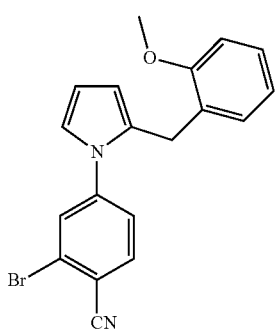

93% yield, white solid. $^1$H NMR (400 MHz, CDCl$_3$) δ 7.64 (dd, J=8.3, 1.0 Hz, 1H), 7.59 (d, J=2.1 Hz, 1H), 7.23-7.17 (m, 1H), 6.98 (dd, J=7.5, 1.8 Hz, 1H), 6.89-6.81 (m, 3H), 6.80 (dd, J=3.1, 1.8 Hz, 1H), 6.31 (t, J=3.2 Hz, 1H), 6.14-6.10 (m, 1H), 3.94 (s, 2H), 3.79 (s, 3H). $^{13}$C NMR (126 MHz, CDCl$_3$) δ 156.58, 144.74, 134.59, 131.89, 129.72, 129.59, 127.75, 127.41, 125.62, 124.28, 121.40, 120.50, 116.88, 113.34, 111.56, 110.15, 110.12, 55.31, 26.47. HRMS (ESI) m/z [M+H] for C$_{19}$H$_{16}$BrN$_2$O: 367.0446, found 367.0455.

2-bromo-4-(2-(2,6-difluorobenzyl)-1H-pyrrol-1-yl)benzonitrile (7n)

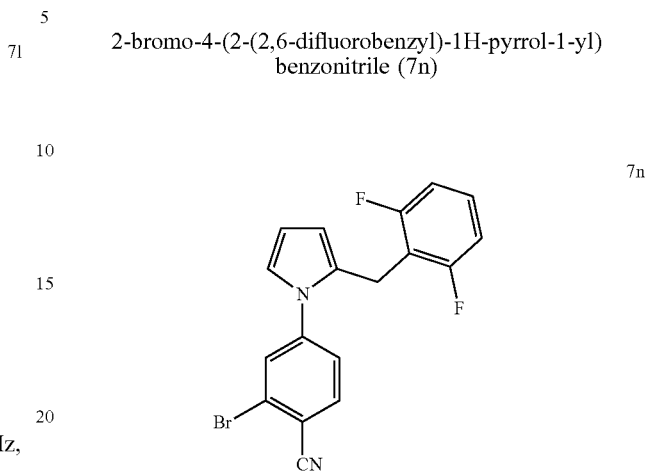

83% yield, white solid. $^1$H NMR (500 MHz, CDCl$_3$) δ 7.77 (dd, J=8.2, 2.1 Hz, 1H), 7.71 (d, J=2.0 Hz, 1H), 7.45 (dd, J=8.3, 2.0 Hz, 1H), 7.23-7.16 (m, 2H), 6.89-6.84 (m, 2H), 6.75 (dd, J=2.9, 1.8 Hz, 1H), 6.24 (t, J=3.2 Hz, 1H), 5.96 (m, 1H), 3.99-3.92 (m, 2H). $^{13}$C NMR (126 MHz, CDCl$_3$) δ 162.25 (2), 144.50, 134.87, 130.30, 128.46, 125.97, 124.95, 121.86, 116.77, 114.13, 111.36, 111.16, 110.52 (2), 110.06, 77.28, 20.19. HRMS (ESI) m/z [M+Na] for C$_{18}$H$_n$BrF$_2$N$_2$Na: 394.9976, found 394.9971.

2-bromo-4-(2-(pyridin-2-ylmethyl)-1H-pyrrol-1-yl)benzonitrile (7o)

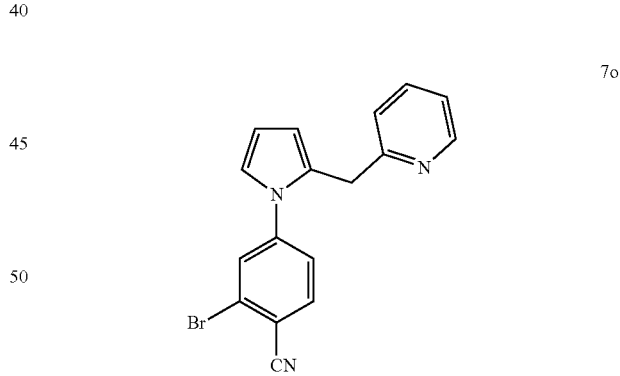

72% yield, white amorphous solid. $^1$H NMR (500 MHz, CDCl$_3$) δ 8.41 (m, 1H), 7.57 (d, J=8.3 Hz, 1H), 7.27 (dd, J=8.3, 2.1 Hz, 2H), 7.06 (m, 1H), 7.01-6.96 (m, 1H), 6.72 (dd, J=3.0, 1.7 Hz, 1H), 6.24 (t, J=3.2 Hz, 1H), 6.08 (m, 1H), 4.08 (d, J=1.0 Hz, 2H). $^{13}$C NMR (126 MHz, CDCl$_3$) δ 158.92, 149.27, 144.43, 136.79, 134.74, 130.46, 130.02, 125.79, 124.56, 122.88, 121.95, 121.69, 116.73, 113.77, 111.79, 110.37, 35.77. HRMS (ESI) m/z [M+H] for C$_{17}$H$_{13}$BrN$_3$: 338.0293, found 338.0300.

2-bromo-4-(2-(pyridin-3-ylmethyl)-1H-pyrrol-1-yl)benzonitrile (7p)

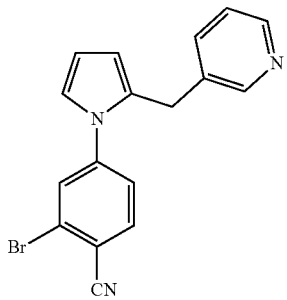

74% yield, white amorphous solid. $^1$H NMR (500 MHz, CDCl$_3$) δ 8.30 (d, J=55.8 Hz, 2H), 7.92 (d, J=7.5 Hz, 1H), 7.39-7.27 (m, 2H), 6.74 (dd, J=2.9, 1.8 Hz, 1H), 6.37 (d, J=2.0 Hz, 1H), 6.28 (dd, J=8.3, 2.0 Hz, 1H), 6.19 (dd, J=3.5, 2.9 Hz, 1H), 5.99 (m, 1H), 3.88 (s, 2H). $^{13}$C NMR (126 MHz, CDCl$_3$) δ 150.16, 149.80, 147.54, 144.36, 136.11, 135.33, 130.44, 129.50, 126.01, 123.35, 122.20, 111.70, 111.54, 109.89, 109.12, 108.54, 30.41. HRMS (ESI) m/z [M+H] for C$_{17}$H$_{13}$BrN$_3$: 338.0293, found 338.0319.

2-bromo-4-(2-(pyridin-4-ylmethyl)-1H-pyrrol-yl)benzonitrile (7q)

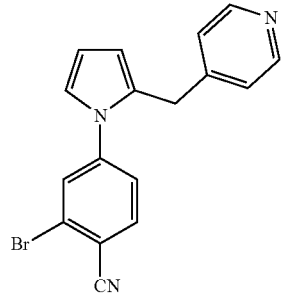

70% yield, white amorphous solid. $^1$H NMR (500 MHz, CDCl$_3$) δ 8.43-8.39 (m, 2H), 7.58 (d, J=8.3 Hz, 1H), 7.43 (d, J=2.0 Hz, 1H), 7.14 (dd, J=8.3, 2.1 Hz, 1H), 6.93 (m, 2H), 6.74 (dd, J=3.0, 1.7 Hz, 1H), 6.25 (t, J=3.3 Hz, 1H), 6.10 (m, 1H), 3.88 (s, 2H). $^{13}$C NMR (126 MHz, CDCl$_3$) δ 149.77 (2), 148.35, 144.19, 134.88, 129.92, 129.48, 126.00, 124.46, 123.66 (2), 122.39, 116.54, 114.15, 112.29, 110.34, 32.55. HRMS (ESI) m/z [M+H] for C17H13BrN3: 338.0293, found 338.0319.

2-bromo-4-(2-phenethyl-1H-pyrrol-1-yl)benzonitrile (7r)

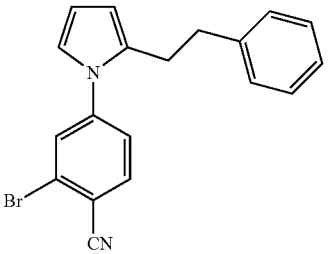

80% yield, white amorphous solid. $^1$H NMR (500 MHz, CDCl$_3$) δ 7.69 (d, J=8.3 Hz, 1H), 7.50 (d, J=2.0 Hz, 1H), 7.28-7.21 (m, 4H), 7.09-7.03 (m, 2H), 6.72 (dd, J=3.0, 1.7 Hz, 1H), 6.31 (t, J=3.2 Hz, 1H), 6.22 (m, 1H), 2.94-2.82 (m, 4H). $^{13}$C NMR (126 MHz, CDCl$_3$) δ 144.63, 140.85, 134.72, 133.04, 129.83, 128.44 (2), 128.33, 126.27 (2), 125.92, 124.52, 121.33, 116.78, 113.64, 110.08, 109.48, 36.00, 28.88. HRMS (ESI) m/z [M+H] for C$_{19}$H$_{16}$BrN$_2$: 351.0496, found 351.0436.

General Procedure for Synthesis of 5a-j, 8a-q, and 9

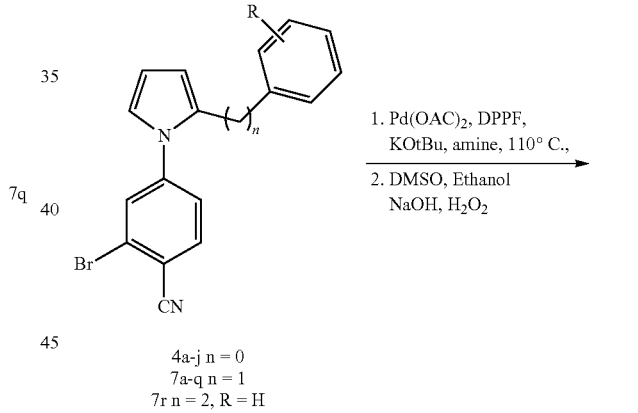

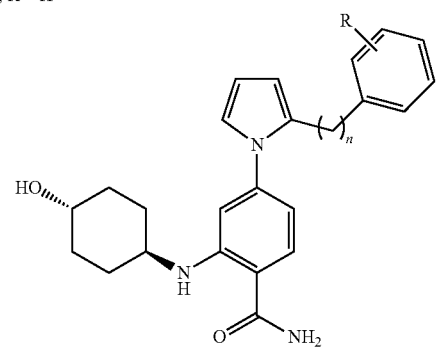

2-Bromobenzonitrile intermediate (4a-j or 7a-q or 7r) (0.07 mmol), trans-4-aminocyclohexanol (0.2 mmol), Pd(OAc)$_2$ (5 mol %), DPPF (10 mol %) and KO/Bu (0.14 mmol) were suspended in toluene (0.4 mL) in a 5 mL microwave reaction vessel. Argon was purged through the reaction mixture for 15 min and the reaction vessel was sealed before subjecting it to microwave irradiation at 120° C. for 20 min. The reaction vessel was cooled and reaction mixture was concentrated in vacuo. The residue was diluted with 5 mL water and extracted thrice with ethyl acetate (3×5 mL). The combined organic fractions were dried over sodium sulfate and concentrated. To this residue was added 5 mL of ethanol and DMSO mixture (4:1), 0.5 mL 1N NaOH solution, and 0.5 mL 30% H$_2$O$_2$ solution. The reaction was stirred at rt or at increased temperature (65° C. for compounds 8j-l) until the benzonitrile intermediate disappeared, as observed using TLC. Subsequently, solvent was evaporated and saturated NH$_4$Cl solution ~20 mL was added followed by extraction with ethyl acetate (3×25 mL). Combined organic layers were washed with brine (2×10 mL), dried over sodium sulfate and adsorbed onto silica gel for column chromatography using 50-80% ethyl acetate in hexanes to obtain the corresponding benzamide product amorphous solids.

2-(((1r,4r)-4-hydroxycyclohexyl)amino)-4-(2-phenyl-1H-pyrrol-1-yl)benzamide (5a)

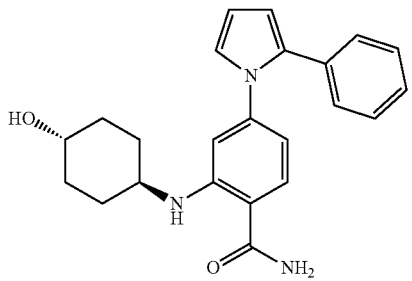

5a

51% yield, white amorphous solid. $^1$H NMR (400 MHz, CDCl$_3$) δ 7.53 (d, J=8.9 Hz, 1H), 7.32-7.21 (m, 1H), 7.19 (m, 2H), 7.01 (m, 1H), 6.68 (d, J=8.2 Hz, 1H), 6.44 (dd, J=4.4, 2.6 Hz, 2H), 6.39 (t, J=3.2 Hz, 1H), 6.12-5.4 (s, 2H) 3.60 (s, 1H), 2.81 (s, 1H), 1.89 (s, 2H), 1.71 (s, 2H), 1.18 (q, J=9.4 Hz, 4H). $^{13}$C NMR (126 MHz, CDCl$_3$) δ 169.24, 155.66, 145.77, 144.74, 134.20, 133.75, 130.22, 128.84 (2), 128.45 (2), 126.99, 123.67, 112.79, 111.11, 99.83, 85.76, 68.99, 60.30, 33.09 (2), 30.97 (2) HRMS (ESI) m/z [M+Na] for C$_{23}$H$_{25}$N$_3$O$_2$Na: 398.1844, found 398.1834.

2-(((1i %4r)-4-hydroxycyclohexyl)amino)-4-(2-(o-tolyl)-1H-pyrrol-1-yl)benzamide (5b)

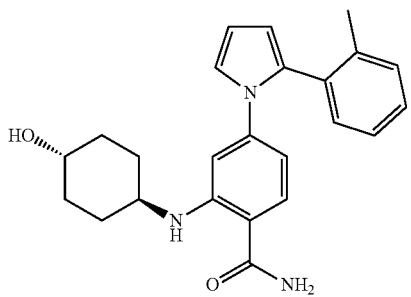

5b

45% yield, white amorphous solid. $^1$H NMR (400 MHz, CDCl$_3$) δ 7.35 (d, J=8.5 Hz, 1H), 7.23-7.20 (m, 2H), 7.18-7.15 (m, 1H), 7.06 (dd, J=2.9, 1.8 Hz, 1H), 6.50 (dd, J=8.5, 2.1 Hz, 1H), 6.40 (m, 1H), 6.31 (dd, J=3.5, 1.8 Hz, 1H), 6.14 (d, J=2.0 Hz, 1H), 5.55 (s, 2H), 3.63 (m, 1H), 2.64 (s, 1H), 2.03 (s, 3H), 1.91 (d, J=12.3 Hz, 2H), 1.66 (d, J=12.8 Hz, 2H), 1.37-1.18 (m, 4H). $^{13}$C NMR (126 MHz, CDCl$_3$) δ 171.52, 149.66, 144.66, 137.45, 133.49, 132.76, 130.88, 130.21, 129.54, 127.66, 125.78, 121.83, 112.10, 109.84, 109.37, 109.01, 107.82, 69.96, 50.09, 33.96 (2), 30.12 (2), 20.22. HRMS (ESI) m/z [M−H] for C$_{24}$H$_{26}$N$_3$O$_2$: 388.2025, found 388.2028.

2-(((1r,4r)-4-hydroxycyclohexyl)amino)-4-(2-(m-tolyl)-1H-pyrroyl-1-yl)benzamide (5c)

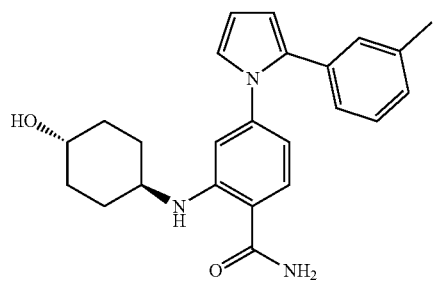

5c

50% yield, white amorphous solid. $^1$H NMR (400 MHz, CDCl$_3$) δ 7.39 (d, J=8.5 Hz, 1H), 7.14 (m, 2H), 7.05-6.98 (m, 2H), 6.95 (d, J=7.6 Hz, 1H), 6.52 (d, J=8.3 Hz, 1H), 6.43 (m, 1H), 6.39 (t, J=3.2 Hz, 1H), 6.29 (s, 1H), 5.59 (s, 2H), 3.62 (s, 1H), 2.87 (s, 1H), 2.31 (s, 3H), 1.88 (d, J=10.4 Hz, 2H), 1.71 (d, J=10.4 Hz, 2H), 1.18 (q, J=9.9 Hz, 4H). $^{13}$C NMR (126 MHz, CDCl$_3$) δ 171.59, 149.83, 144.57, 137.85, 133.88, 133.06, 129.51, 129.10, 128.10, 127.27, 125.76, 123.62, 111.38, 110.27, 110.05, 109.59, 109.43, 69.92, 50.10, 33.84 (2), 30.09 (2), 21.51. HRMS (ESI) m/z [M+H] for C$_{24}$H$_{28}$N$_3$O$_2$: 390.2182, found 390.2184.

2-(((1r,4r)-4-hydroxycyclohexyl)amino)-4-(2-(p-tolyl)-1H-pyrrol-1-yl)benzamide (5d)

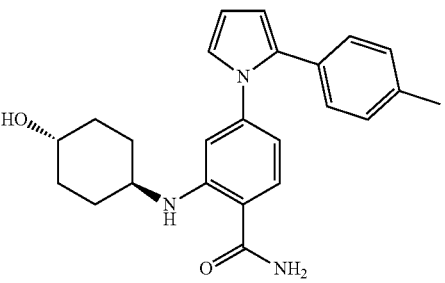

5d

50% yield, white amorphous solid. $^1$H NMR (400 MHz, CDCl$_3$) δ 7.92 (s, 1H), 7.38 (d, J=8.3 Hz, 1H), 7.11 (s, 4H), 7.00 (m, 1H), 6.51 (m, 1H), 6.43-6.37 (m, 2H), 6.27 (s, 1H), 5.73-5.41 (s, 2H), 3.63 (s, 1H), 2.88 (s, 1H), 2.33 (s, 3H), 1.89 (d, J=10.3 Hz, 2H), 1.70 (d, J=11.0 Hz, 2H), 1.18 (q, J=12.3 Hz, 4H). $^{13}$C NMR (126 MHz, CDCl$_3$) δ 13C NMR (126 MHz, CDCl$_3$) δ 171.52, 149.80, 144.61, 136.22, 133.81, 130.28, 129.51, 128.93 (2), 128.45 (2), 123.42, 111.03, 110.28, 110.12, 109.53, 109.43, 69.92, 50.09, 33.87 (2), 30.12 (2), 21.18. HRMS (ESI) m/z [M−H] for C$_{24}$H$_{26}$N$_3$O$_2$: 388.2025, found 388.2028.

4-(2-(2-chlorophenyl)-1H-pyrrol-1-yl)-2-(((1r,4r)-4-hydroxycyclohexyl)amino)benzamide (5e)

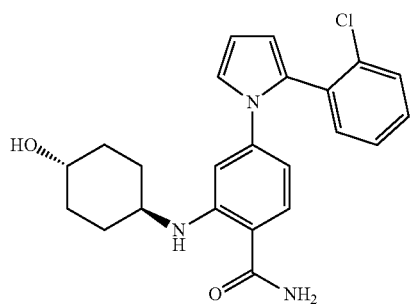

55% yield, white amorphous solid. $^1$H NMR (500 MHz, CDCl$_3$) δ 8.07-8.11 (m, 1H), 7.50-7.60 (m, 2H), 7.46-7.49 (m, 1H), 7.40-7.43 (m, 2H), 7.24 (dd, J=2.9, 1.8 Hz, 1H), 6.67 (dd, J=8.4, 2.1 Hz, 1H), 6.57-6.64 (m, 2H), 6.35 (d, J=2.1 Hz, 1H), 5.78 (s, 2H), 3.81 (m, 1H), 2.95 (d, J=6.6 Hz, 1H), 2.05-2.13 (m, 2H), 1.81-1.91 (m, 2H), 1.32 (m, 4H). $^{13}$C NMR (126 MHz, CDCl$_3$) δ 171.47, 149.73, 144.55, 134.32, 132.78, 132.39, 130.05, 129.76, 129.57, 128.72, 126.64, 122.68, 113.14, 110.17, 109.47, 109.42, 108.02, 69.92, 50.15, 33.94 (2), 30.12 (2). HRMS (ESI) m/z [M−H] for C$_{23}$H$_{23}$ClN$_3$O$_2$: 408.1479, found 408.1461.

4-(2-(3-chlorophenyl)-1H-pyrrol-yl)-2-(((1r,4r)-4-hydroxycyclohexyl)amino)benzamide (5f)

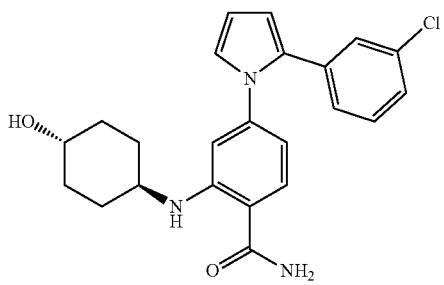

59% yield, white amorphous solid. $^1$H NMR (500 MHz, CDCl$_3$) δ 7.88 (s, 1H), 7.31 (d, J=8.4 Hz, 1H), 7.12-7.08 (m, 2H), 6.95-6.91 (m, 2H), 6.42-6.36 (m, 2H), 6.30 (dd, J=3.6, 2.8 Hz, 1H), 6.19 (d, J=2.0 Hz, 1H), 5.54 (s, 2H), 3.54 (m, 1H), 2.83 (d, J=11.0 Hz, 1H), 1.84 (m, 2H), 1.66 (m, 2H), 1.17-1.06 (m, 4H). $^{13}$C NMR (126 MHz, CDCl$_3$) δ 171.34, 149.77, 144.17, 134.94, 134.10, 132.16, 129.69, 129.42, 128.16, 126.62, 126.42, 124.41, 112.17, 110.83, 110.27, 109.83, 109.52, 69.84, 50.30, 33.78 (2), 30.01 (2). HRMS (ESI) m/z [M−H] for C$_{23}$H$_{23}$ClN$_3$O$_2$: 408.1479, found 408.1483.

4-(2-(4-chlorophenyl)-1H-pyrrol-1-yl)-2-(((1r,4r)-4-hydroxycyclohexyl)amino)benzamide (5g)

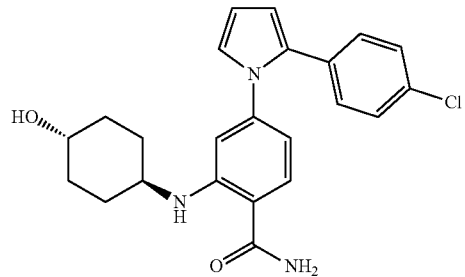

55% yield, white amorphous solid. $^1$H NMR (500 MHz, CDCl$_3$) δ 7.90 (d, J=7.2 Hz, 1H), 7.37 (d, J=8.4 Hz, 1H), 7.25-7.22 (m, 2H), 7.15-7.09 (m, 2H), 6.99 (m, 1H), 6.47-6.40 (m, 2H), 6.37 (m, 1H), 6.21 (d, J=2.0 Hz, 1H), 3.63 (m, 1H), 2.89 (m, 1H), 1.95-1.88 (m, 2H), 1.69 (m, 2H), 1.23-1.12 (m, 4H). $^{13}$C NMR (126 MHz, CDCl$_3$) δ 171.35, 149.87, 144.25, 132.44, 132.42, 131.62, 129.67, 129.64 (2), 128.43 (2), 124.15, 111.69, 110.64, 110.09, 109.76, 109.33, 69.83, 50.15, 33.79, 30.09. HRMS (ESI) m/z [M+H] for C$_{23}$H$_{25}$ClN$_3$O$_2$: 410.1635, found 410.1633.

2-(((1r,4r)-4-hydroxycyclohexyl)amino)-4-(2-(pyridin-2-yl)-1H-pyrrol-1-yl)benzamide (5h)

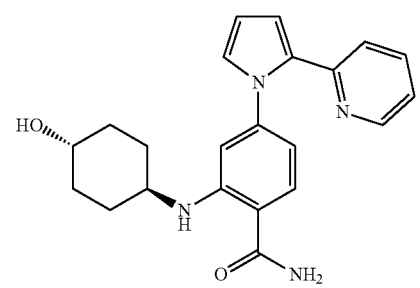

55% yield, white amorphous solid. $^1$H NMR (500 MHz, CDCl$_3$) δ 8.55 (d, J=4.9 Hz, 1H), 7.93 (d, J=7.3 Hz, 1H), 7.59 (s, 1H), 7.38 (d, J=8.4 Hz, 1H), 7.12 (m, 2H), 7.06-7.01 (m, 1H), 6.49-6.39 (m, 2H), 6.33 (d, J=1.7 Hz, 1H), 5.54 (d, J=64.2 Hz, 2H), 3.62 (m, 1H), 3.05-2.91 (m, 1H), 1.95-1.73 (m, 4H), 1.25-1.15 (m, 4H). $^{13}$C NMR (126 MHz, CDCl$_3$) δ 171.48, 149.96, 149.41, 144.90, 135.85, 131.33, 129.62, 128.32, 125.41, 122.76, 120.79, 113.70, 110.71, 110.29, 109.94, 109.17, 69.83, 50.03, 33.72 (2), 30.09 (2). HRMS (ESI) m/z [M+H] for C$_{22}$H$_{25}$N$_4$O$_2$: 377.1978, found 377.1979.

2-(((1r,4r)-4-hydroxycyclohexyl)amino)-4-(2-(pyridin-3-yl)-1H-pyrrol-1-yl)benzamide (5i)

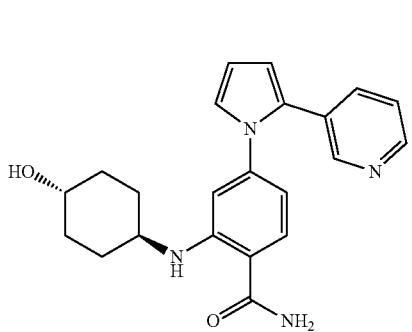

59% yield, white amorphous solid. $^1$H NMR (500 MHz, CDCl$_3$) δ 8.52-8.40 (m, 2H), 7.95 (d, J=7.3 Hz, 1H), 7.53 (m, 1H), 7.38 (d, J=8.4 Hz, 1H), 7.24 (dd, J=8.0, 4.9 Hz, 1H), 7.06 (dd, J=2.9, 1.7 Hz, 1H), 6.55 (dd, J=3.6, 1.7 Hz, 1H), 6.45-6.38 (m, 2H), 6.32 (d, J=2.0 Hz, 1H), 5.62 (s, 2H), 3.65 (dd, J=9.8, 5.6 Hz, 1H), 2.99 (m, 1H), 1.94 (m, 2H), 1.84-1.72 (m, 2H), 1.27-1.18 (m, 4H). $^{13}$C NMR (126 MHz, CDCl$_3$) δ 171.26, 150.08, 148.50, 146.78, 144.03, 135.48, 129.81, 129.28, 125.07, 123.17, 112.44, 111.20, 110.56, 110.06, 109.11, 99.99, 69.75, 50.11, 33.69 (2), 29.98 (2). HRMS (ESI) m/z [M−H] for $C_{22}H_{23}N_4O_2$: 375.1821, found 375.1834.

2-(((1r,4r)-4-hydroxycyclohexyl)amino)-4-(2-(pyridin-4-yl)-1H-pyrrol-1-yl)benzamide (5j)

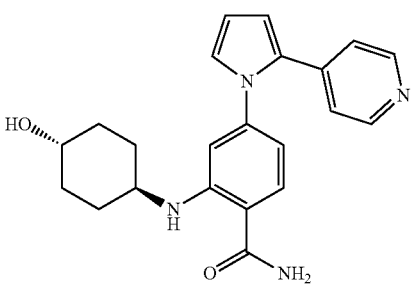

48% yield, white amorphous solid. $^1$H NMR (500 MHz, CDCl$_3$) δ 8.45 (s, 2H), 7.98 (d, J=12 Hz, 1H), 7.38 (d, J=8.4 Hz, 1H), 7.13-7.00 (m, 3H), 6.64 (dd, J=3.7, 1.7 Hz, 1H), 6.44-6.36 (m, 2H), 6.32 (d, J=2.0 Hz, 1H), 5.63 (s, 2H), 3.63 (td, J=9.6, 4.5 Hz, 1H), 3.06-2.94 (m, 1H), 1.92 (dt, J=7.0, 4.3 Hz, 2H), 1.77 (dt, J=10.9, 2.6 Hz, 2H), 1.27-1.17 (m, 4H). $^{13}$C NMR (126 MHz, CDCl$_3$) δ 171.24, 150.11, 149.16, 144.05, 140.58, 130.62, 129.83, 126.39, 122.10, 113.74, 111.27, 110.47, 110.32, 109.14, 69.70, 50.18, 33.66 (2), 30.02 (2). HRMS (ESI) m/z [M−H] for $C_{22}H_{23}N_4O_2$: 375.1821, found 375.1823.

4-(2-benzyl-1H-pyrrol-1-yl)-2-(((1r,4r)-4-hydroxycyclohexyl)amino)benzamide (8a)

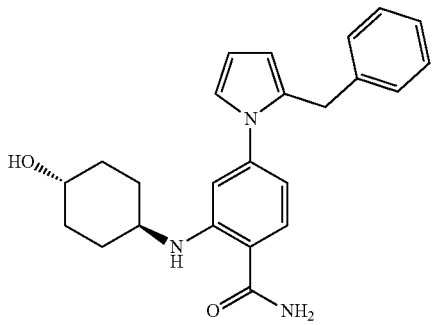

44% yield, white amorphous solid. $^1$H NMR (500 MHz, CDCl$_3$) δ 7.87 (d, J=7.6 Hz, 1H), 7.32-7.26 (m, 1H), 7.21 (q, J=1.3 Hz, 0H), 7.18 (q, J=1.2, 0.8 Hz, 1H), 7.15-7.10 (m, 1H), 7.08-7.01 (m, 2H), 6.75 (dd, J=2.9, 1.8 Hz, 1H), 6.34 (d, J=7.0 Hz, 2H), 6.20 (t, J=3.2 Hz, 1H), 6.00 (m, 1H), 5.58 (s, 2H), 3.88 (s, 2H), 3.63-3.54 (m, 1H), 2.90-2.80 (m, 1H), 1.93-1.81 (m, 4H), 1.28-1.12 (m, 4H). $^{13}$C NMR (126 MHz, CDCl$_3$) 13C NMR (126 MHz, CDCl$_3$) δ 171.48, 150.08, 144.64, 140.10, 131.54, 129.37, 128.43 (2), 128.40 (2), 126.19, 121.64, 111.69, 111.10, 109.88, 109.20, 108.49, 69.80, 49.71, 33.48, 32.90 (2), 30.15 (2). HRMS (ESI) m/z [M−H] for $C_{24}H_{26}N_3O_2$: 388.2025, found 388.22036.

4-(2-(2-chlorobenzyl)-1H-pyrrol-1-yl)-2-(((1r,4r)-4-hydroxycyclohexyl)amino)benzamide (8b)

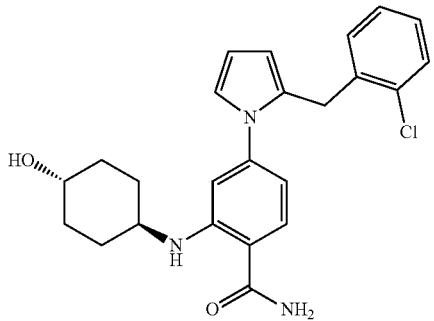

51% yield, white amorphous solid. $^1$H NMR (500 MHz, CDCl$_3$) δ 7.91 (d, J=7.6 Hz, 1H), 7.33-7.25 (m, 2H), 7.13-7.01 (m, 3H), 6.78 (dd, J=2.9, 1.8 Hz, 1H), 6.43-6.35 (m, 2H), 6.21 (t, J=3.2 Hz, 1H), 5.94 (m, 1H), 5.46 (d, J=55.2 Hz, 2H), 3.97 (s, 2H), 3.60 (s, 1H), 2.94 (s, 1H), 1.90 (m, 4H), 1.27-1.13 (m, 4H). $^{13}$C NMR (126 MHz, CDCl$_3$) δ 171.41, 150.18, 144.51, 137.78, 133.76, 130.31, 129.98, 129.54, 129.37, 127.73, 126.83, 121.77, 111.34, 111.09, 110.20, 108.67, 108.65, 69.76, 49.85, 33.52 (2), 30.68 (2), 30.17. HRMS (ESI) m/z [M−H] for $C_{24}H_{25}ClN_3O_2$: 422.1635, found 422.1642.

4-(2-(3-chlorobenzyl)-1H-pyrrol-1-yl)-2-(((1r,4r)-4-hydroxycyclohexyl)amino)benzamide (8c)

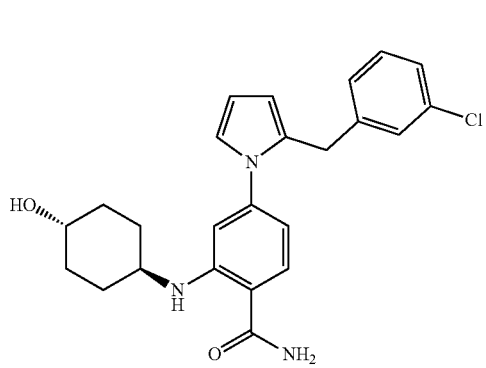

53% yield, white amorphous solid. $^1$H NMR (500 MHz, CDCl$_3$) δ 7.97 (d, J=7.6 Hz, 1H), 7.38 (d, J=8.8 Hz, 1H), 7.20-7.16 (m, 2H), 7.07 (td, J=1.8, 0.9 Hz, 1H), 7.01-6.97 (m, 1H), 6.83 (dd, J=2.9, 1.8 Hz, 1H), 6.41-6.36 (m, 2H), 6.32-6.25 (m, 1H), 6.14-6.07 (m, 1H), 5.63 (s, 2H), 3.93 (s, 2H), 3.68 (m, 1H), 3.02-2.91 (m, 1H), 2.04-1.90 (m, 4H), 1.35-1.20 (m, 4H). $^{13}$C NMR (126 MHz, CDCl$_3$) δ 171.40, 150.10, 144.46, 142.18, 134.20, 130.60, 129.60, 129.39, 128.49, 126.58, 126.37, 121.95, 111.72, 111.32, 110.03, 109.22, 108.53, 69.75, 49.83, 33.50, 32.60 (2), 30.14 (2). HRMS (ESI) m/z [M−H] for C$_{24}$H$_{25}$ClN$_3$O$_2$: 422.1635, found 422.1645.

4-(2-(4-chlorobenzyl)-1H-pyrrol-1-yl)-2-(((1r,4r)-4-hydroxycyclohexyl)amino)benzamide (8d)

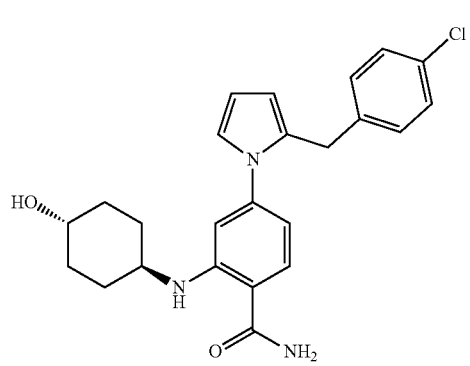

44% yield, white amorphous solid. $^1$H NMR (500 MHz, CDCl$_3$) δ 7.95 (d, J=7.6 Hz, 1H), 7.36 (d, J=8.3 Hz, 1H), 7.24-7.18 (m, 2H), 7.06-6.98 (m, 2H), 6.81 (dd, J=2.9, 1.8 Hz, 1H), 6.38 (dd, J=8.3, 2.0 Hz, 1H), 6.34 (d, J=2.0 Hz, 1H), 6.27 (dd, J=3.5, 2.9 Hz, 1H), 6.08 (m, 1H), 5.61 (s, 2H), 3.91 (s, 2H), 3.64 (m, 1H), 2.89 (m, 1H), 2.01-1.89 (m, 4H), 1.27-1.22 (m, 4H). $^{13}$C NMR (126 MHz, CDCl$_3$) δ 13C NMR (126 MHz, CDCl$_3$) δ 171.37, 150.07, 144.48, 138.68, 131.79, 130.83, 129.72 (2), 129.41, 128.52 (2), 121.89, 111.62, 111.21, 109.99, 109.07, 108.52, 69.76, 49.84, 33.62 (2), 32.28, 30.21 (2). HRMS (ESI) m/z [M−H] for C$_{24}$H$_{25}$ClN$_3$O$_2$: 422.1635, found 422.1642.

4-(2-(2-fluorobenzyl)-1H-pyrrol-1-yl)-2-(((1r,4r)-4-hydroxycyclohexyl)amino)benzamide (8e)

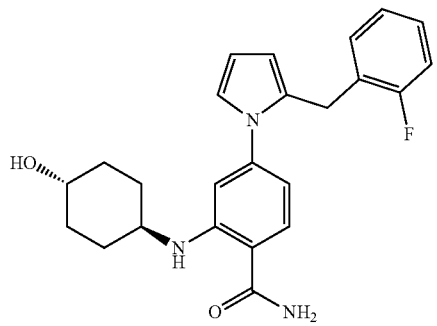

48% yield, white amorphous solid. $^1$H NMR (500 MHz, CDCl$_3$) δ 8.08 (s, 1H), 7.40 (d, J=8.3 Hz, 1H), 7.21-7.15 (m, 1H), 7.08-6.95 (m, 3H), 6.82 (dd, J=2.9, 1.8 Hz, 1H), 6.52 (d, J=2.0 Hz, 1H), 6.46 (dd, J=8.3, 2.0 Hz, 1H), 6.26 (t, J=3.2 Hz, 1H), 6.04 (dd, J=3.6, 1.7 Hz, 1H), 5.69 (s, 2H), 3.97 (s, 2H), 3.67 (m, 1H), 3.04 (m, 1H), 2.10-1.90 (m, 4H), 1.37-1.23 (m, 4H). $^{13}$C NMR (126 MHz, CDCl$_3$) δ 171.38, 161.61, 159.65, 144.53, 130.50, 130.11, 129.48, 127.95, 126.89, 124.03, 121.84, 115.19, 115.02, 112.01, 109.98, 109.42, 108.61, 69.73, 50.24, 33.51 (2), 30.08 (2), 25.89. HRMS (ESI) m/z [M+H] for C$_{24}$H$_{27}$FN$_3$O$_2$: 408.2087, found 408.2086.

4-(2-(3-fluorobenzyl)-1H-pyrrol-1-yl)-2-(((1r,4r)-4-hydroxycyclohexyl)amino)benzamide (8f)

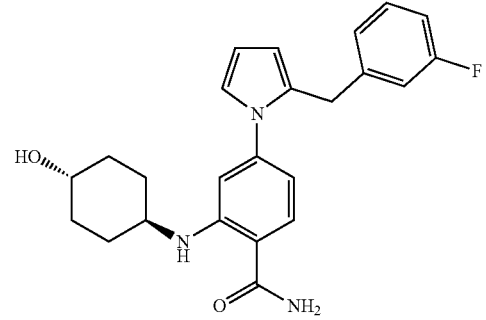

42% yield, white amorphous solid. $^1$H NMR (500 MHz, CDCl$_3$) δ 8.08 (s, 1H), 7.38 (d, J=8.3 Hz, 1H), 7.20 (m, 1H), 6.90-6.87 (m, 2H), 6.81 (m, 2H), 6.47-6.39 (m, 2H), 6.29-6.24 (m, 1H), 6.10 (dd, J=3.5, 1.7 Hz, 1H), 5.68 (s, 2H), 3.95 (s, 2H), 3.65 (m, 1H), 2.99 (m, 1H), 2.03-1.93 (m, 4H), 1.36-1.21 (m, 4H). $^{13}$C NMR (126 MHz, CDCl$_3$) δ 171.31, 163.91, 161.95, 144.50, 142.70, 130.69, 129.80, 129.73, 129.41, 123.99, 121.92, 115.36, 115.19, 113.17, 113.01, 110.13, 108.63, 69.70, 50.23, 33.47, 32.62 (2), 30.03 (2). HRMS (ESI) m/z [M+H] for C$_{24}$H$_{27}$FN$_3$O$_2$: 408.2087, found 408.2101.

4-(2-(4-fluorobenzyl)-1H-pyrrol-1-yl)-2-(((1r,4r)-4-hydroxycyclohexyl)amino)benzamide (8 g)

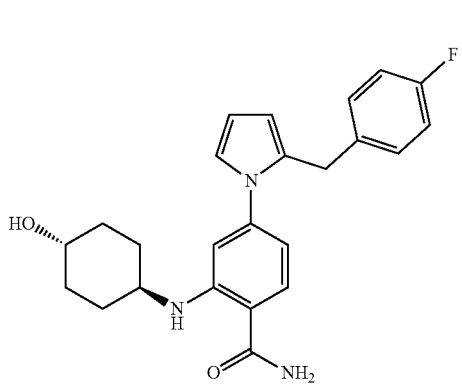

42% yield, white amorphous solid. $^1$H NMR (500 MHz, CDCl$_3$) δ 8.00 (s, 1H), 7.37 (d, J=8.1 Hz, 1H), 7.04 (dd, J=8.4, 5.4 Hz, 2H), 6.97-6.88 (m, 2H), 6.80 (t, J=2.4 Hz, 1H), 6.44-6.36 (m, 2H), 6.26 (t, J=3.2 Hz, 1H), 6.06 (dd, J=3.3, 1.8 Hz, 1H), 5.84-5.44 (m, 2H), 3.91 (s, 2H), 3.67 (m, 1H), 2.97 (t, J=8.0 Hz, 1H), 1.97 (t, J=5.5 Hz, 4H), 1.37-1.18 (m, 4H). $^{13}$C NMR (126 MHz, CDCl$_3$) δ 171.38, 162.31, 160.37, 149.91, 144.57, 135.64, 131.47, 129.77 (2), 129.37, 121.87, 115.23 (2), 111.89, 109.82, 109.37, 108.48, 69.71, 50.01, 33.55, 32.21 (2), 30.13 (2). HRMS (ESI) m/z [M−H] for C$_{24}$H$_{25}$FN$_3$O$_2$: 406.1931, found 406.1923.

4-(2-(2-bromobenzyl)-1H-pyrrol-1-yl)-2-(((1r,4r)-4-hydroxycyclohexyl)amino)benzamide (8h)

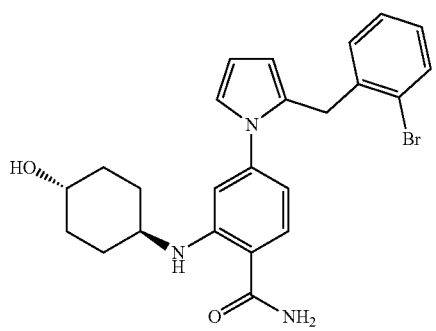

41% yield, white amorphous solid. $^1$H NMR (500 MHz, CDCl$_3$) δ 7.62-7.54 (m, 1H), 7.52 (dd, 7.9, 1.3 Hz, 1H), 7.25-7.18 (m, 2H), 7.12-7.02 (m, 2H), 6.92-6.81 (m, 2H), 6.75 (d, J=8.4 Hz, 1H), 6.30 (t, J=3.2 Hz, 1H), 6.04 (dd, J=3.5, 1.7 Hz, 1H), 4.05 (s, 2H), 3.71-3.63 (m, 1H), 3.09-3.03 (m, 1H), 1.99 (t, J=14.8 Hz, 4H), 1.46-1.31 (m, 2H). $^{13}$C NMR (126 MHz, CDCl$_3$) δ 170.55, 144.60, 139.18, 133.52, 132.66, 130.36, 130.01, 129.67, 128.09, 127.59, 127.20, 124.25, 121.92, 111.11, 109.40, 69.41, 53.45, 33.31 (2), 31.60, 29.72 (2). HRMS (ESI) m/z [M−H] for C$_{24}$H$_{25}$BrN$_3$O$_2$: 466.1130, found 466.1123.

2-(((1r,4r)-4-hydroxycyclohexyl)amino)-4-(2-(2-methylbenzyl)-1H-pyrrol-1-yl)benzamide (8i)

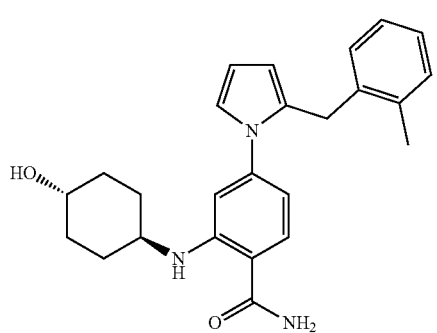

45% yield, white solid. $^1$H NMR (500 MHz, CDCl$_3$) δ 8.20-7.76 (m, 1H), 7.35-7.31 (m, 1H), 7.08 (m, 3H), 6.98 (m, 1H), 6.78 (dd, J=2.9, 1.8 Hz, 1H), 6.46-6.40 (m, 2H), 6.19 (t, J=3.2 Hz, 1H), 5.87 (m, 1H), 5.68 (d, J=57.1 Hz, 2H), 3.80 (s, 2H), 3.68-3.52 (m, 1H), 2.87 (s, 1H), 2.12 (s, 3H), 1.941-1.81 (m, 4H), 1.26-1.15 (m, 4H). $^{13}$C NMR (126 MHz, CDCl$_3$) $^{13}$C NMR (126 MHz, CDCl$_3$) δ 171.37, 144.69, 138.29, 136.00, 131.09, 130.08, 130.00, 129.49, 129.21, 128.86, 126.48, 126.45, 126.13, 121.44, 111.90, 110.05, 108.71, 69.74, 50.20, 33.44 (2), 30.69, 30.06 (2), 19.44. HRMS (ESI) m/z [M+H] for C$_{25}$H$_{30}$N$_3$O$_2$: 404.2338, found 404.2350.

4-(2-(2-hydroxybenzyl)-1H-pyrrol-1-yl)-2-(((1r,4r)-4-hydroxycyclohexyl)amino)benzamide (8j)

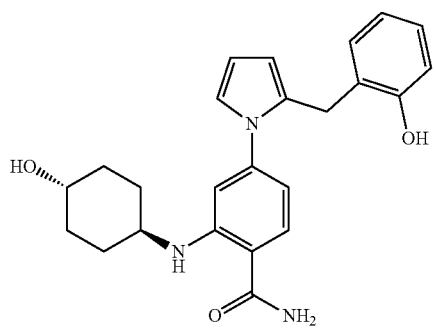

46% yield, white amorphous solid. $^1$H NMR (400 MHz, Methanol-d4) δ 7.52-7.46 (m, 1H), 6.96 (m, 1H), 6.80-6.71 (m, 2H), 6.66 (m, 2H), 6.38 (d, J=7.5 Hz, 2H), 6.12 (t, J=3.2 Hz, 1H), 5.92 (m, 1H), 3.79 (s, 2H), 3.46 (m, 1H), 2.77 (m, 1H), 1.88-1.68 (m, 4H), 1.29-0.96 (m, 4H). $^{13}$C NMR (126 MHz, CDCl$_3$) δ 13C NMR (126 MHz, MeOD) δ 172.99, 154.50, 149.70, 144.42, 130.56, 129.97, 128.96, 126.99, 126.87, 120.81, 119.04, 114.28, 111.76, 110.95, 109.66, 108.10, 108.07, 69.12, 49.34, 32.68 (2), 30.08 (2), 26.27. HRMS (ESI) m/z [M+Na] for C$_{24}$H$_{27}$N$_3$O$_3$Na: 428.1950, found 428.1949.

4-(2-(3-hydroxybenzyl)-1H-pyrrol-1-yl)-2-(((1r,4r)-4-hydroxycyclohexyl)amino)benzamide (8k)

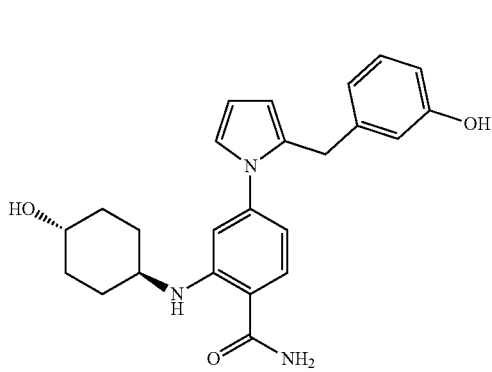

42% yield, white amorphous solid. $^1$H NMR (400 MHz, CDCl$_3$) δ 7.80 (d, J=IP Hz, 1H), 7.38 (d, J=8.3 Hz, 1H), 7.12 (t, J=7.8 Hz, 1H), 6.83 (dd, J=2.9, 1.8 Hz, 1H), 6.74-6.63 (m, 3H), 6.44 (dd, J=8.4, 2.0 Hz, 1H), 6.35-6.28 (m, 2H), 6.19 (dd, J=3.4, 1.8 Hz, 1H), 3.91 (s, 2H), 5.61-5.90 (s, 2H) 3.64 (q, J=10.8 Hz, 1H), 2.65 (s, 1H), 1.89 (d, J=11.3 Hz, 4H), 1.24-1.10 (m, 4H). $^{13}$C NMR (126 MHz, CDCl$_3$) δ 168.64, 166.43, 162.90, 157.79, 152.71, 148.84, 141.58, 119.49, 117.65, 115.39, 113.27, 109.31, 106.40, 99.52, 94.41, 90.08, 86.38, 68.98, 61.90, 46.01, 31.76 (2), 28.83 (2). HRMS (ESI) m/z [M+Na] for C$_{24}$H$_{27}$N$_3$O$_3$Na: 428.1950, found 428.1974.

4-(2-(4-hydroxy benzyl)-1H-pyrrol-1-yl)-2-(((1r,4r)-4-hydroxycylohexyl)amino)benzamide (8l)

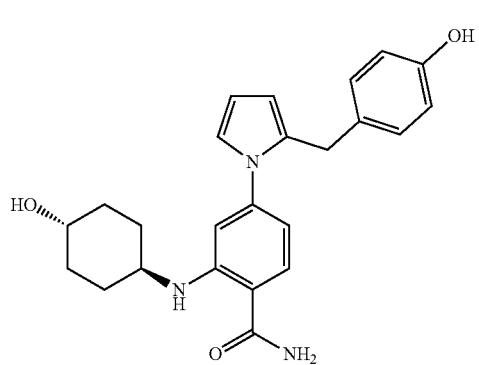

42% yield, white amorphous solid. $^1$H NMR (400 MHz, CDCl$_3$) δ 7.82 (d, J=8.5 Hz, 1H), 7.38 (d, 8.4 Hz, 1H), 7.01 (d, J=8.2 Hz, 2H), 6.89 (d, J=8.5 Hz, 1H), 6.82 (dd, J=2.9, 1.8 Hz, 1H), 6.81-6.74 (m, 2H), 6.68 (d, J=8.2 Hz, 1H), 6.44 (dd, J=8.4, 2.0 Hz, 1H), 6.32-6.29 (m, 2H), 6.16 (d, J=3.6 Hz, 1H), 5.45-5.80 (s, 2H), 3.89 (s, 2H), 3.61 (s, 1H), 2.62 (s, 1H), 1.88 (m, 4H), 1.19 (m, 4H). $^{13}$C NMR (126 MHz, CDCl$_3$) δ 171.93, 154.50, 144.57, 132.16, 131.00, 129.49 (2), 129.34, 128.94, 121.36, 115.87 (2), 111.30, 110.41, 108.72, 108.61, 108.42, 70.03, 55.99, 33.12 (2), 31.52, 30.28 (2). HRMS (ESI) m/z [M+H] for C24H28N3O3: 406.2131, found 406.2135.

2-(((1r,4r)-4-hydroxycyclohexyl)amino)-4-(2-(2-methoxybenzyl)-1H-pyrrol-1-yl)benzamide (8m)

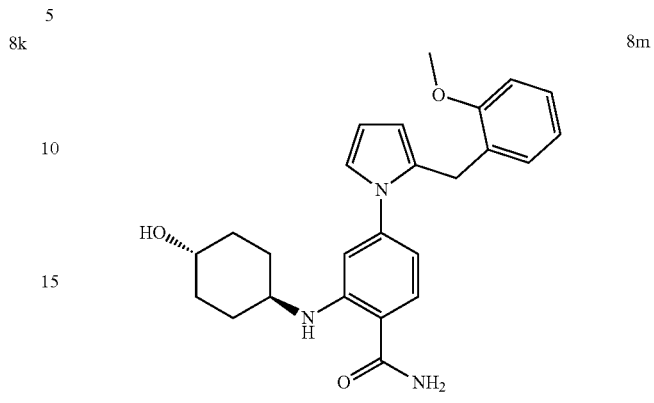

51% yield, white amorphous solid. $^1$H NMR (500 MHz, CDCl$_3$) δ 7.93 (d, J=7.4 Hz, 1H), 7.35 (d, J=8.3 Hz, 1H), 7.19 (m, 1H), 6.99 (m, 1H), 6.89-6.80 (m, 3H), 6.51-6.41 (m, 2H), 6.26 (dd, J=3.4, 2.9 Hz, 1H), 6.03 (m, 1H), 5.53 (s, 2H), 3.91 (s, 2H), 3.75 (s, 3H), 3.71-3.58 (m, 1H), 2.95 (d, J=30.9 Hz, 1H), 1.99-1.88 (m, 4H), 1.30-1.16 (m, 4H). $^{13}$C NMR (126 MHz, CDCl$_3$) δ 171.51, 156.91, 150.08, 144.75, 131.25, 129.55, 129.36, 128.73, 127.42, 121.32, 120.48, 111.52, 110.85, 110.01, 109.86, 108.83, 108.55, 69.79, 55.30, 49.72, 33.47 (2), 30.16 (2), 26.77. HRMS (ESI) m/z [M+H] for C$_{25}$H$_{30}$N$_3$O$_3$: 420.2287, found 420.2292.

4-(2-(2,6-difluorobenzyl)-1H-pyrrol-1-yl)-2-(((1r,4r)-4hydroxycyclohexyl)amino)benzamide (8n)

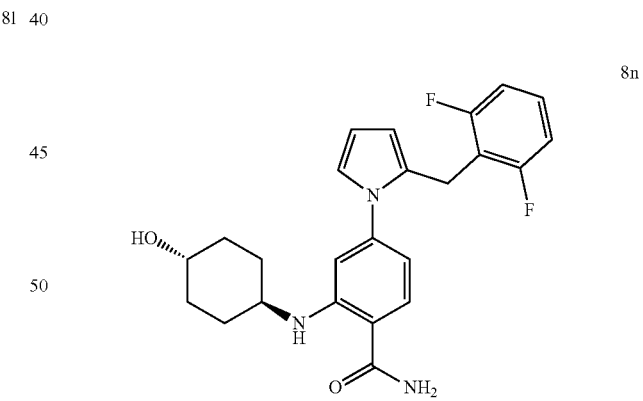

55% yield, white amorphous solid. $^1$H NMR (500 MHz, CDCl$_3$) δ 8.01 (s, 1H), 7.38 (d, J=8.3 Hz, 1H), 7.16-7.06 (m, 1H), 6.82-6.77 (m, 2H), 6.70 (dd, J=2.9, 1.8 Hz, 1H), 6.61 (d, J=2.0 Hz, 1H), 6.49 (dd, J=8.3, 2.0 Hz, 1H), 6.11 (t, J=3.2 Hz, 1H), 5.85-5.38 (m, 3H), 3.88 (d, J=1.4 Hz, 2H), 3.64 (m, 1H),3.24 (s, 1H), 2.10-1.90 (m, 4H), 1.39-1.26 (m, 4H). $^{13}$C NMR (126 MHz, CDCl$_3$) δ 171.47, 162.48, 160.51, 150.17, 144.59, 130.97, 129.95, 129.51, 128.11, 121.80, 112.00, 111.44, 111.28, 111.07, 109.56, 108.50, 108.40, 69.84, 50.22, 33.65 (2), 30.24 (2), 20.18. HRMS (ESI) m/z [M−H] for C$_{24}$H$_{24}$F$_2$N$_3$O: 424.1837, found 424.1838.

2-(((1r,4r)-4-hydroxycyclohexyl)amino)-4-(2-(pyridin-2-ylmethyl)-1H-pyrrol-1-yl)benzamide (8o)

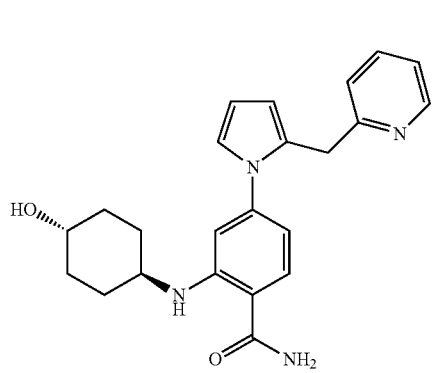

48% yield, white amorphous solid. $^1$H NMR (400 MHz, CDCl$_3$) δ 8.52 (d, J=5.0 Hz, 1H), 7.95 (s, 1H), 7.69 (s, 1H), 7.43 (d, J=8.4 Hz, 1H), 7.24-7.10 (m, 2H), 6.87 (s, 1H), 6.47 (d, J=7.3 Hz, 2H), 6.31 (t, J=3.2 Hz, 1H), 6.17 (s, 1H), 5.32 (s, 2H), 4.27 (s, 2H), 3.70 (s, 1H), 3.08 (s, 1H), 1.99 (s, 4H), 1.37-1.26 (m, 4H). $^{13}$C NMR (126 MHz, CDCl$_3$) δ 171.47, 159.98, 150.15, 149.08, 144.48, 136.73, 129.53, 128.34, 122.82, 121.87, 121.39, 111.66, 111.23, 110.07, 109.07, 108.77, 69.74, 49.81, 35.60, 33.52 (2), 30.11 (2). HRMS (ESI) m/z [M+H] for C$_{23}$H$_{27}$N$_4$O$_2$: 391.2134, found 391.2122.

2-(((1r,4r)-4-hydroxycyclohexyl)amino)-4-(2-(pyridin-3-ylmethyl)-1H-pyrrol-1-yl) benzamide (8p)

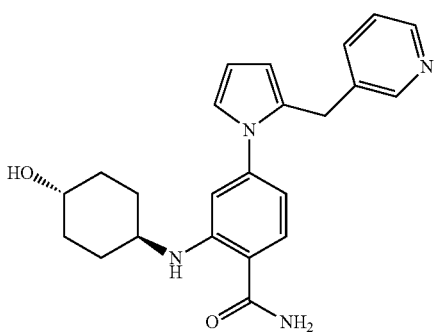

44% yield, white amorphous solid. $^1$H NMR (500 MHz, CDCl$_3$) δ 8.38 (d, J=55.8 Hz, 2H), 8.00 (d, J=7.5 Hz, 1H), 7.43 (m, 1H), 7.38 (d, J=8.3 Hz, 1H), 7.19 (dd, J=7.8, 4.8 Hz, 1H), 6.82 (dd, J=2.9, 1.8 Hz, 1H), 6.44 (d, J=2.0 Hz, 1H), 6.36 (dd, J=8.3, 2.0 Hz, 1H), 6.26 (dd, 7=3.5, 2.9 Hz, 1H), 6.07 (m, 1H), 5.78 (d, J=111.9 Hz, 2H), 3.96 (s, 2H), 3.69 (m, 1H), 3.09 (m, 1H), 2.05-1.96 (m, 4H), 1.37-1.29 (m, 4H). $^{13}$C NMR (126 MHz, CDCl$_3$) δ 171.36, 150.16, 149.80, 147.54, 144.36, 136.11, 135.33, 130.44, 129.50, 123.35, 122.20, 111.70, 111.54, 109.89, 109.12, 108.54, 69.70, 49.97, 33.55 (2), 30.41 (2), 30.15 (2). HRMS (ESI) m/z [M+H] for C$_{23}$H$_{27}$N$_4$O$_2$: 391.2134, found 391.2122.

2-(((1r,4r)-4-hydroxycyclohexyl)amino)-4-(2-(pyridin-4-ylmethyl)-1H-pyrrol-1-yl)benzamide (8q)

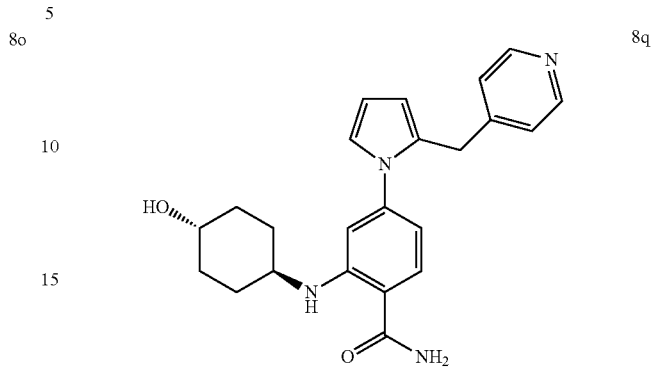

48% yield, white amorphous solid. $^1$H NMR (500 MHz, CDCl$_3$) δ 8.52-8.44 (m, 2H), 8.01 (s, 1H), 7.34 (d, J=8.3 Hz, 1H), 7.14 (d, J=5.4 Hz, 2H), 6.84 (dd, J=2.9, 1.8 Hz, 1H), 6.36 (d, J=2.0 Hz, 1H), 6.31-6.25 (m, 2H), 6.16 (dd, J=3.4, 1.8 Hz, 1H), 5.54 (d, J=99.5 Hz, 2H), 4.02 (s, 2H), 3.66 (dd, J=10.4, 4.8 Hz, 1H), 2.98 (d, J=10.2 Hz, 1H), 2.02-1.94 (m, 4H), 1.34-1.27 (m, 4H). $^{13}$C NMR (126 MHz, CDCl$_3$) δ 171.20, 171.20, 150.14 (2), 147.37, 144.12, 129.58, 128.50, 124.40 (2), 122.58, 111.54, 110.60, 109.24, 109.00, 108.78, 69.63, 50.00, 33.56 (2), 32.68, 30.15 (2). HRMS (ESI) m/z [M–H] for C$_{23}$H$_{27}$N$_4$O$_2$: 391.2134, found 391.2122.

2-(((1r,4r)-4-hydroxycyclohexyl)amino)-4-(2-phenethyl-1H-pyrrol-1-yl)benzamide (9)

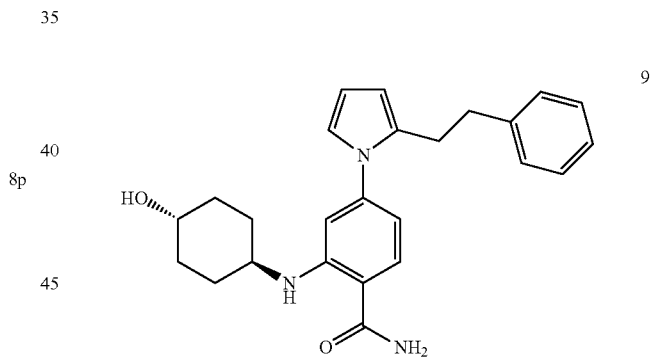

45% yield, white amorphous solid. $^1$H NMR (500 MHz, CDCl$_3$) δ 8.10 (s, 1H), 7.41 (d, J=8.2 Hz, 1H), 7.24 (d, J=7.5 Hz, 2H), 7.20-7.14 (m, 1H), 7.13-7.07 (m, 2H), 6.79 (t, J=2.3 Hz, 1H), 6.62 (s, 1H), 6.47 (dd, J=8.4, 2.1 Hz, 1H), 6.25 (t, J=3.1 Hz, 1H), 6.15 (dd, J=3.4, 1.7 Hz, 1H), 5.67 (s, 2H), 3.70 (m, 1H), 3.26 (m, 1H), 2.97-2.81 (m, 4H), 2.14-1.95 (m, 4H), 1.42-1.29 (m, 4H). $^{13}$C NMR (126 MHz, CDCl$_3$) δ 171.39, 149.99, 144.79, 141.55, 133.06, 129.48 (2), 128.36, 128.27 (2), 126.02, 121.43, 111.81, 111.33, 109.20, 108.37, 107.69, 69.75, 50.39, 35.47, 33.62 (2), 30.17 (2), 29.26. HRMS (ESI) m/z [M–H] for C$_{25}$H$_{28}$N$_3$O$_2$: 402.2181, found 402.2176.

Fluorescence Polarization. Assay buffer (25 μL, 20 mM HEPES pH 7.3, 50 mM KCl, 5 mM MgCl$_2$, 1 mM DTT, 20 mM Na$_2$MoO$_4$, 0.01% NP-40, and 0.5 mg/mL BGG) was added to 96-well plate (black well, black bottom) followed by the desired compound at the indicated final concentrations in DMSO (1% DMSO final concentration). Recombinant cGrp94 (10 nM for compounds 2-27, 30 nM for compounds 28-48) and FITC-GDA were then added (6 nM). Plates were incubated with rocking for 5 h at 4° C. Fluorescence was determined using excitation and emission filters of 485 and 528 nm, respectively. Percent FITC-GDA bound was determined by using the DMSO millipolarization unit (mP) as the 100% bound value and the 0% for FITC-GDA. $K_d$ values were calculated from separate experiments performed in triplicate using GraphPad Prism.

Molecular Modeling. Surflex-Docking module in Sybyl v8.0 was used for molecular modeling and docking studies. The co-crystal structures of RDA bound to Grp94 (PDB code: 2GFD), SNX 2112 bound to Hsp90 (PDB code: 4NH7) and PU-H54 bound to GRp94 (PDB code: 3O2F) were utilized for modeling experiments. Pymol was used for further visualization and figure preparation.

Protein Trafficking and Anti-Migratory Effects of Grp94 Inhibitors

Chemicals and Cell culture. Compounds were dissolved in DMSO and stored at −20° C. until use. The PC3-MM2 and MDA-MB-231 cells were maintained in DMEM (Cellgro) media supplemented with streptomycin (500 µg/mL), penicillin (100 units/mL) and 10% FBS at 37° C. and 5% $CO_2$.

Antibodies. The following antibodies were used for western blotting and/or immunofluorescence: goat anti-integrin α L #sc6609, rabbit anti-SYNE2 #sc99066, and rabbit anti-actin #sc1616-R (Santa Cruz Biotech-nology, Santa Cruz, CA); rabbit anti-integrin a 2 #ab181548, rabbit anti-VAMP2 #ab3347 (Abeam, Cambridge, MA); Phalloidin 647 #A22287 (Invitrogen, Carlsbad CA); rabbit anti-Rab10 #4262S (Cell Signaling Technology, Danvers, Mass.).

Cell fractionation and Western Blot Analysis. The PC3-MM2 cells treated with DMSO, or compounds dissolved in DMSO at specified concentrations for 24 h, were trypsinized, washed twice with ice-cold phosphate-buffered saline (PBS), and resuspended in 10 mL of isolation buffer containing 10 mM Tris-HCl, pH 7.4, 1 mM EDTA, 0.2 M D-mannitol, 0.05 M sucrose, 0.5 mM sodium orthovanadate, 1 mM sodium fluoride, and protease inhibitor cocktail.[42] The cells were homogenized with the aid of a Teflon pestle and lysis was confirmed microscopically. After sedimenting the cell debris, the protein concentration of each lysate was measured in quadruplicate using the BCA protein assay and bovine serum albumin as the standard. The coefficient of variation was determined for each set of quadruplicate measures and if the variability exceeded 5%, the protein assay was repeated for that set of samples. The cell lysates containing equal amount of protein were centrifuged at 8000 g for 10 min and the crude mitochondrial pellet (Mito) was washed 2× in isolation buffer and frozen. The reserved supernatant was centrifued at 14000 g to isolate a microsomal fraction (MIC) and the remaining supernatant (Cyto) was concentrated overnight by TCA precipitation and dissolved in a minimum amount of isolation buffer and subjected to SDS-PAGE. Equal volume of sample were electrophoresed under reducing conditions (8% polyacrylamide gel), transferred to a polyvinylidene fluoride membrane (PVDF), and immunoblotted with the corresponding specific antibodies. Membranes were incubated with an appropriate horseradish peroxidase-labeled secondary antibody, developed with a chemiluminescent substrate and visualized.

Immunofluorescence Analysis. For cell imaging, 1 µm-Slide 8 well ibidiTreat IBIDI glass slides were used. PC3-MM2 cells were fixed with freshly made 4% (w/w) paraformaldehyde in PBS for 15 min, permeabilized with 0.1% (w/w) Tween 20 in PBS for 5 min and quenched with 0.1% (w/w) sodium borohydride for 5 min. The sections were blocked with 3% (w/w) BSA in PBS for 1 h and incubated with the primary antibody at a 1:100 concentration in 1% BSA in PBS overnight, prior to incubation with secondary antibody conjugated with Alexa Fluor 568 for 3 h. The sections were counterstained with DAPI and/or with Phalloidin to visualize DNA and filamentous actin (F-actin), respectively. The wells were washed three times with PBS after each step.

Confocal images were acquired using a custom epifluorescent/confocal microscope composed of the following components: an Olympus IX81 inverted spinning disc confocal microscope base (Olympus America, Center Valley, PA.), a Prior microscope stage for automated image acquisition (Prior Scientific, Rockland, MA), an Olympus 60× oil Immersion objective for confocal images (Olympus) and a Hamamatsu Electron Multiplying Charge-Coupled Device (EMCCD) camera (Hamamatsu, Hamamatsu, Shizuoka Prefecture, Japan). Images were captured using the SlideBook acquisition and analysis software, (Intelligent Imaging Innovations (3i), Denver, CO).

Images were collected with 8-10 image stacks with a 0.3 micron step size through the cells. Images were processed using Image J software (NIH).

Wound Healing Scratch Assay. The cells were seeded in a 24-well plate in complete media and allowed to form a monolayer. After monolayer formation, a scratch was introduced with a sterile 0.1-10 µl pipet tip. The media was replaced with fresh media in the absence or presence of the indicated drug concentrations. Photomicrographs were taken at different time points with an Olympus IX71 microscope using a 10× air lens and CellSans Dimensions software. The images were processed with Image J software.

Anti-proliferation Assays. Cells were seeded (2000/well, 100 µL) in 96-well plates and incubated overnight. Following incubation, compounds with varying concentrations in DMSO (1% DMSO final concentration) were added and cells were returned to the incubator for 72 h. After 72 h, the cell viability was determined using an MTS/PMS cell proliferation kit (Promega) per the manufacturer's instructions. Absorption value from 1% DMSO wells were used as 100% proliferation, and values were adjusted accordingly.

Effect of Grp94-Selective Inhibitors on Myocilin Levels

Cell Culture. Cell culture was performed as described in the art.[25] Tetracycline-inducible Hek cells stably overexpressing I477N mutant myocilin were grown and maintained in Dulbecco's Modified Eagle's Medium supplemented with 10% fetal bovine serum (Invitrogen, penicillin (100 units/mL), streptomycin (100 mg/mL) and 1% GlutaMAX (Invitrogen) at 37 C and 5% CO2. Stably overexpressing cells were selected for using hygromycin B (200 mg/mL) (InvivoGen) and G418 (100 mg/mL) (Gibco). I477N myocilin expression was induced with tetracycline (5 mg/mL) for 48H prior to drug treatment.

Inhibitor Treatment. Inhibitors were solubilized in DMSO (Sigma Aldrich), and diluted to documented concentrations. Cells were treated drop wise with inhibitors 24H prior to cell harvest. DMSO concentration was diluted to 1% total cell medium volume.

Cell Harvest. Cell harvest was performed as previously described.[21] 24H after inhibitor treatment, culture medium was removed and cells were washed 2× with ice cold PBS. Mammalian Protein Extraction Reagent (M-PER) buffer (Pierce) containing protease inhibitor cocktail III (Calbiochem), 100 mM phenylmethylsulfonyl fluoride (PMSF) and phosphatase inhibitor II and III mixtures (Sigma) were added to washed cells at a 1:100 dilution and scraped. Scraped cells in lysis buffer was incubated for 10 minutes on ice to allow for lysis to occur. Cell lysates were then centrifuged at 16000×g for 10 min to separate cell lysates from nuclear debris. Bicinchoninic acid assay (BCA) was performed to determine protein concentration in cell lysates, and samples were prepared for western blot analysis.

Western Blotting. Western blot analysis was performed as previously described.[41] Cell lysates were prepared at identical protein concentrations, as determined by BCA analysis, in 2× Laemmli sample buffer (Bio-Rad) and denatured by boiling for 5 min at 100 C. Denatured samples were then loaded onto a 10-well 10% gel (Bio-Rad). Gels were run at 125 volts until dye front reached the bottom of the gel cassette. Gels were then transferred onto PVDF membrane (Millipore) at 100 volts for 1 hour. After transfer, blots were blocked in 7% milk in TBS fir 1 hour at room temperature prior to primary antibody incubation. Statistical analysis of imaged blots was performed with ImageJ analysis software (NIH).

Antibodies. Myocilin anti-rabbit primary antibody was provided by Dan Stamer at Duke University. Actin anti-mouse was purchased from Sigma Aldrich (St. Louis, MO). Secondary antibodies were purchased from Southern Biotech (Birmingham, AL). All antibodies were diluted at 1:1000 in 7% milk in TBS. Primary antibodies were incubated shaking overnight at 4 C. Secondary antibodies were incubated shaking at RT for 1 hour.

Results

Compound 5a, which contains an unsubstituted phenyl ring, was evaluated for binding affinity towards Grp94 and Hsp90a. As illustrated in Table 1, compound 5a bound Grp94 (Kd~9 μM) with greater affinity than Hsp90a (Kd>100 μM), supporting that these compounds represent a new class of Grp94-selective inhibitors. Following these encouraging results, structure-activity relationship (SAR) studies were explored for substituents on the phenyl ring to investigate both spatial and electronic requirements of the Grp94 binding pocket. FIG. 1 illustrates the binding model for the Grp94 binding pocket with compound 5a. The incorporation of methyl substituents onto the phenyl ring was pursued to explore steric demands at the 2-, 3-, and 4-positions (5b, 5c, and 5d). These compounds exhibited comparable affinity to 5a, suggesting that additional space was available in this hydrophobic cleft.

TABLE 1

| Compound | R = | $K_d$ Grp94 (μM)[a] | $K_d$ Hsp90α (μM) |
|---|---|---|---|
| 5a | H | 9.05 ± 0.31 | >100 |
| 5b | 2-Me | 9.9 ± 0.54 | >100 |

TABLE 1-continued

| | | | |
|---|---|---|---|
| 5c | 3-Me | 9.43 ± 0.26 | >100 |
| 5d | 4-Me | 8.35 ± 0.14 | >100 |
| 5e | 2-Cl | 2.94 ± 0.27 | >100 |
| 5f | 3-Cl | 15.8 ± 0.31 | >100 |
| 5g | 4-Cl | 10.62 ± 0.54 | >100 |

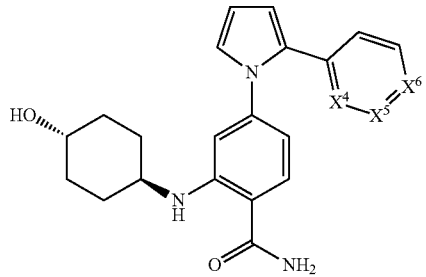

| Compound | N Scan | $K_d$ Grp94 (μM) | $K_d$ Hsp90α (μM) |
|---|---|---|---|
| 5h | $X^4$ = N | 13.98 ± 0.27 | >100 |
| 5i | $X^5$ = N | 5.5 ± 0.15 | >100 |
| 5j | $X^6$ = N | 13.2 ± 0.12 | >100 |

[a]Apparent $K_d$ values determined using fluorescence polarization (FP) assay. Compounds were incubated with cGrp94 and FITC-GDA in triplicates and ± SEM were measured.

Subsequently, chlorine containing compounds (5e-g) were synthesized to investigate the electronic effects within Site 2. The 2-chloro derivative, 5e, exhibited a $K_d$ of ~3 μM (See Table 1, above). Without being bound by theory, the enhanced binding affinity exhibited by 5e is not likely to result from steric effects, since the analog containing a methyl group (5b) at this location was less active. In addition, the phenyl ring in 5a was replaced with a pyridine nitrogen at the 2-,3- and 4-positions (5h-j) to explore the potential for hydrogen bonds with Asn-107 (ASN107) (FIG. 1), whereupon 5i (containing a 3-pyridine ring) exhibited higher affinity than 5a.

In an effort to further improve binding within Site 2, we added a linker between the pyrrole and phenyl ring to project the phenyl ring deeper into the hydrophobic pocket (Site 2). Binding data confirmed that the benzyl substituted compound, 8a, manifested greater affinity than the phenethyl derivative, 9, (Table 2). In fact, 8a produced a $K_d$ of ~1.3 μM, an improvement over 5a.

TABLE 2

8a

TABLE 2-continued

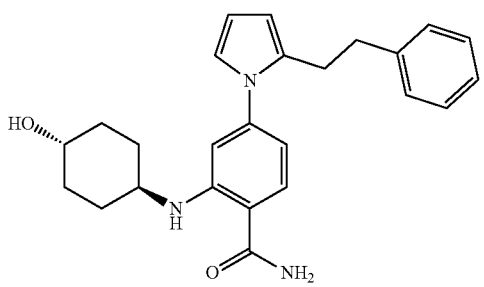 [SMILES: NC(=O)c1ccc(-n2cccc2CCc2ccccc2)cc1N[C@H]1CC[C@H](O)CC1]

| Compound | $K_d$ Grp94 (μM)[b] | $K_d$ Hsp90α (μM) |
|---|---|---|
| 8a | 1.13 ± 0.1 | >100 |
| 9 | >25 | >100 |

[b]Apparent $K_d$ values determined using fluorescence polarization (FP) assay. Compounds were incubated with cGrp94 and FITC-GDA in triplicates and ± SEM were measured.

Encouraged by the increased affinity and selectivity manifested by 8a, SAR studies were initiated about the benzyl side chain via the incorporation of chlorine at all 3 locations on the phenyl ring, 8b-d. The 2-chloro derivative, 8b, produced increased affinity towards Grp94, while lacking affinity for Hsp90 (Table 3).

TABLE 3

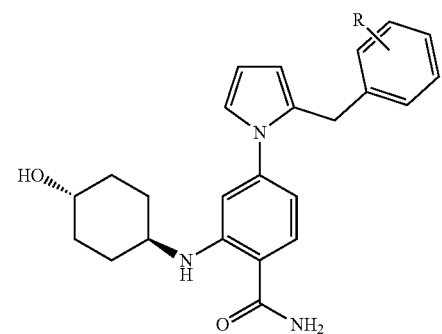

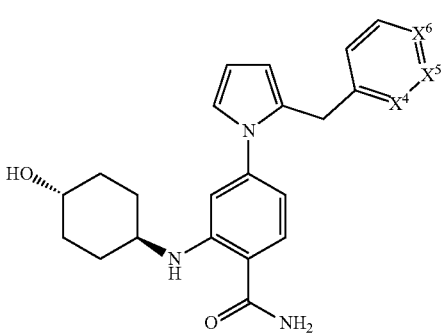

| Compound | R = | $K_d$ Grp94 (μM)[c] | $K_d$ Hsp90α (μM) |
|---|---|---|---|
| 8b | 2-Cl | 0.83 ± 0.12 | >100 |
| 8c | 3-Cl | 2.45 ± 0.45 | >100 |
| 8d | 4-Cl | >25 | >100 |
| 8e | 2-F | 0.72 ± 0.14 | >100 |
| 8f | 3-F | 4.53 ± 0.12 | >100 |
| 8g | 4-F | 8.35 ± 0.14 | >100 |
| 8h | 2-Br | 12.9 ± 0.11 | >100 |
| 8i | 2-Me | 4.2 ± 0.23 | >100 |
| 8j | 2-OH | 0.44 ± 0.09 | >100 |

TABLE 3-continued

| 8k | 3-OH | >25 | >100 |
| 8l | 4-OH | 20.55 ± 0.74 | >100 |
| 8m | 2-OMe | 1.15 ± 0.02 | >100 |
| 8n | 2,6-di-F | >25 | >100 |

| Compound | N Scan | $K_d$ Grp94 (μM) | $K_d$ Hsp90α (μM) |
|---|---|---|---|
| 8o | $X^4$ = N | 13.98 ± 0.27 | >100 |
| 8p | $X^5$ = N | 5.5 ± 0.15 | >100 |
| 8q | $X^6$ = N | 13.2 ± 0.12 | >100 |

[c]Apparent $K_d$ values determined using fluorescence polarization (FP) assay. Compounds were incubated with cGrp94 and FITC-GDA in triplicates and ± SEM were measured.

Additional investigations at the 2-position were also pursued. For example, the 2-flouro analog, 8e, resulted in improved affinity (~724 nM). Without being bound by theory, based on the data observed it is proposed that fluorine interacts with Asn-107 (ASN107), which is also supported by prior studies that have demonstrated that the fluorine atom can interact with asparagine as a hydrogen bond acceptor.[36] Building on the knowledge that the 2-position of the benzyl ring is important for affinity and that ASN107 in Grp94 may produce hydrogen bonding interactions, phenol containing compounds, 8j-l, were synthesized. Upon their preparation, 8j-l were evaluated for binding affinity. Interestingly, the 2-phenol containing derivative 8j exhibited an apparent $K_d$ of ~446 nM towards Grp94 while maintaining >100 μM $K_d$ for binding Hsp90 (>200 fold selectivity). Because a hydroxyl group could serve as a hydrogen bond donor or an acceptor; therefore, the 2-methoxy containing compound, 8m, was synthesized to differentiate the role of the 2-phenol with regards to ASN107. Compound 8m bound Grp94 with $K_d$ of 1.15 μM which was comparable with 8a, despite the hydrophobic constraints at the 2-position, which suggests that the hydrogen bond acceptor role of the phenol is beneficial.

Figure 2A:
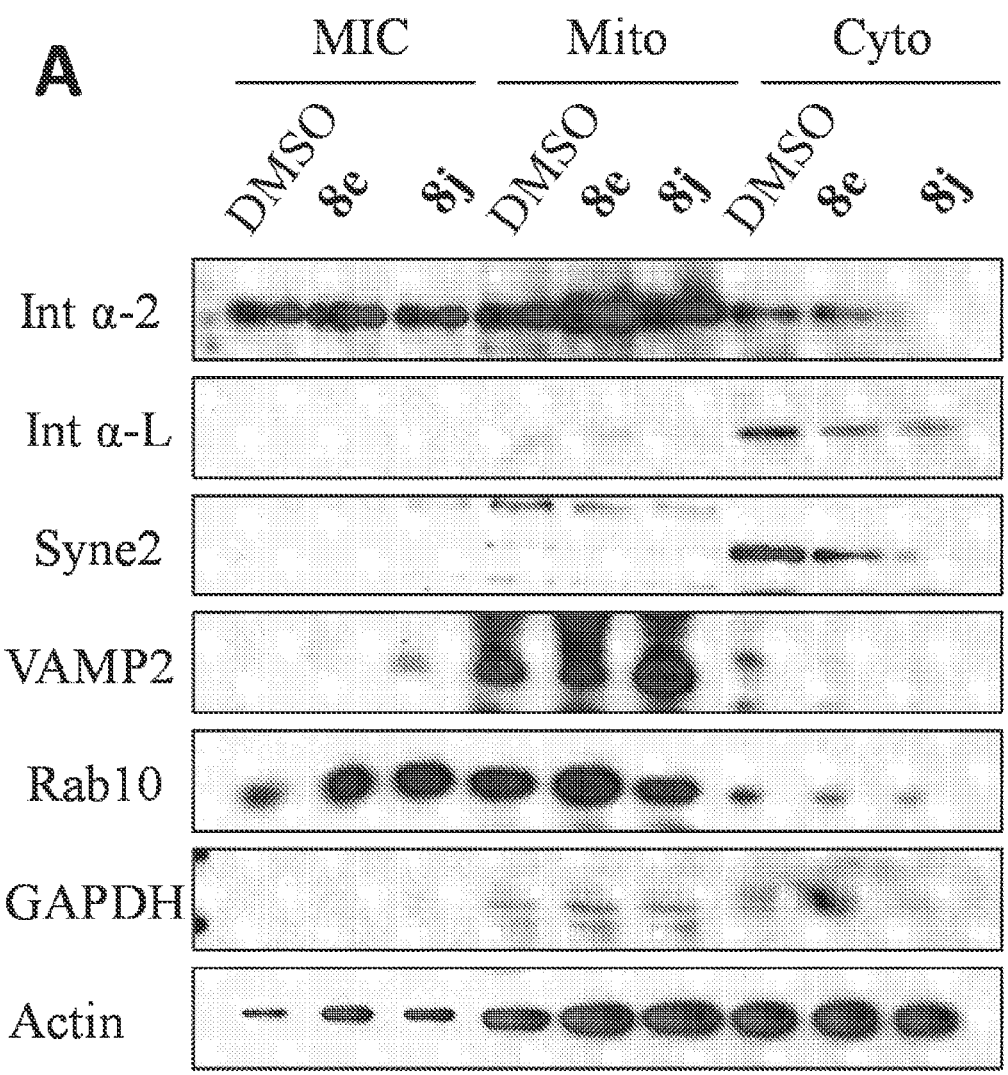
FIGS. 2A-B provide a biological evaluation of certain Grp94 inhibitors, according to the working examples.

Grp94 inhibitors exhibit anti-migratory activity: Grp94 is a pro-oncogenic chaperone that is over-expressed in tumors to modulate cancer cell migration and metastases.[37, 38] Using Grp94 knockdown cells, it has been reported that Grp94 affects intracellular transport pathways during the metastatic process. Although the total levels of proteins did not alter, levels in the microsomal fraction (MIC) were significantly lower in Grp94 knockdown cells compared to control cells, suggesting that Grp94 affects protein localization/trafficking. Specifically, Grp94 knockdown cells downregulated VAMP2 and Rab10, which are critical for intracellular transport; Syne2, which is necessary for filamentous actin (F-actin) attachment to the nucleus; and integrin α2 and αL, which are critical for cell-cell and cell-matrix adhesion.[37] As shown in FIG. 2A, the cytoplasmic (Cyto) fraction of cells treated with 8j and 8e at 30 μM resulted in reduced levels of integrin α2, integrin αL, Syne2, VAMP2, and Rab10 compared to DMSO.

Figure 2B:
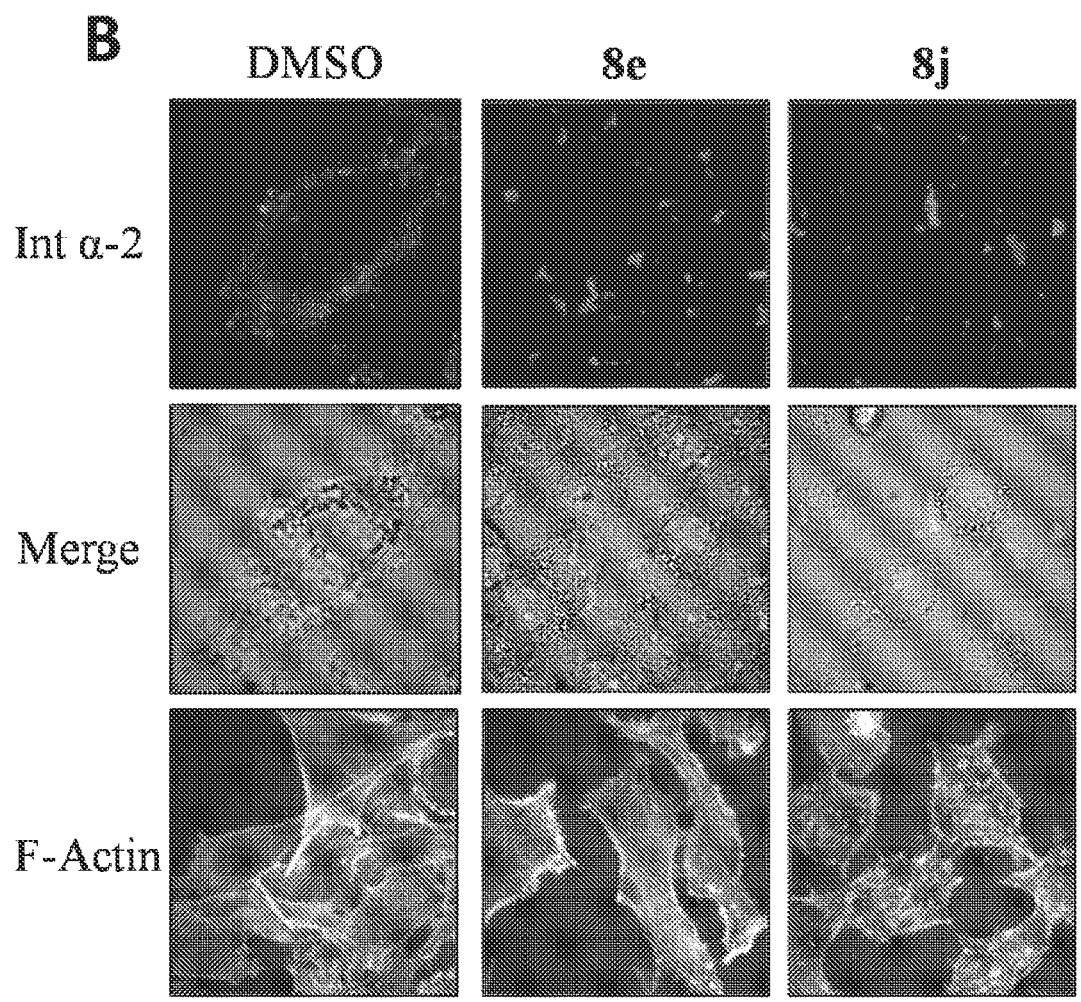

The cell migration process requires cell polarization, protrusion (filopodia, lamellipodia formation), adhesion, and retraction of the rear. Cell protrusion is produced by local actin polymerization causing F-actin formation at the filopodia and lamellipodia.[39] Adhesion is facilitated by formation of the focal adhesion complex at the filopodia tip. Focal adhesion occurs via integrin receptors that bind the extracellular matrix.[37] Different aspects of cell migration processes, such as F-actin localization and integrin trafficking were therefore investigated by confocal microscopy using Grp94 inhibitors 8e and 8j. The microscopy data revealed that F-actin was enriched at the cellular cortex region in DMSO treated cells, which correlates with normal F-actin distribution. In the presence of 8j and 8e, F-actin formed sporadic patches in the cytoplasm, which further supported the role of Grp94 inhibitors to modulate cell protrusion via F-actin reorganization (FIG. 2B).[40] Immunofluorescence analysis showed that integrin α2 is localized to the cell surface in untreated cells, however, in the presence of Grp94 inhibitors (8e and 8j), integrin α2 was localized as patches in the cytoplasm, supporting the role of Grp94 to traffic integrins to the cell membrane (FIG. 2B).

Figure 3B:
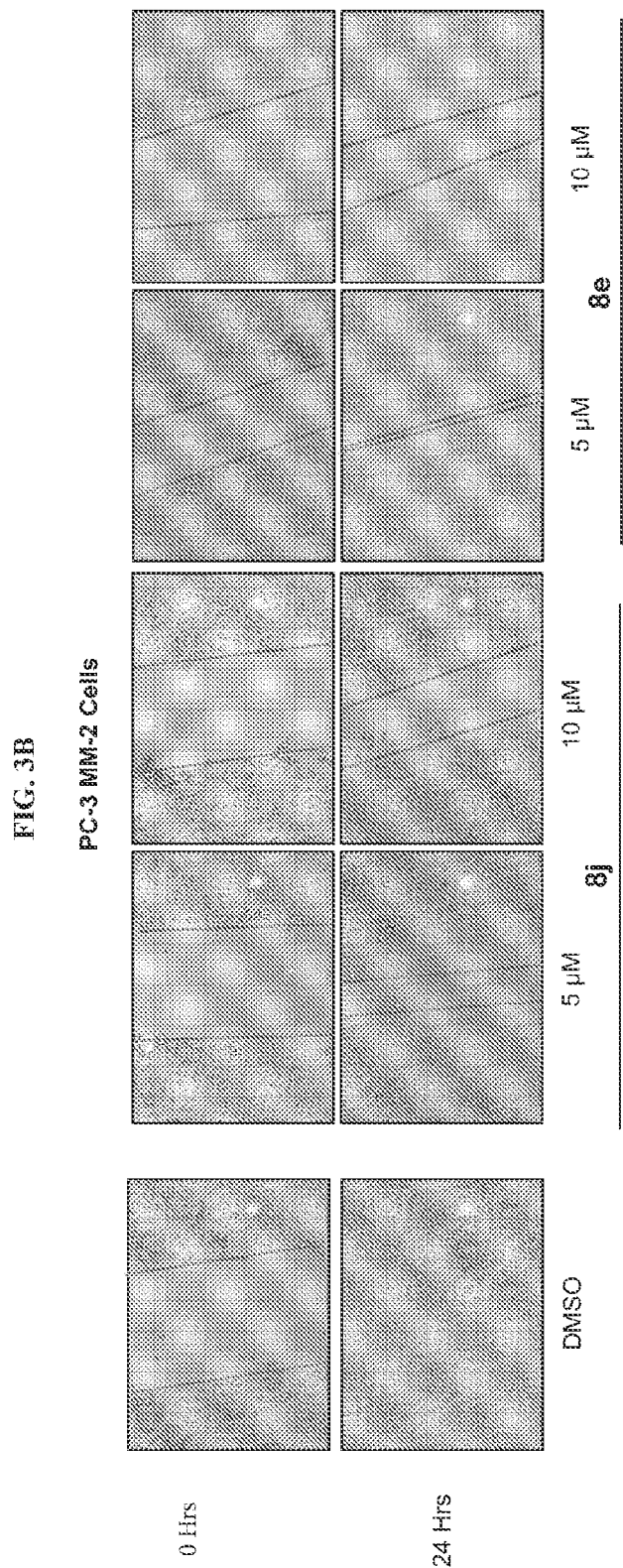
Figure 4:
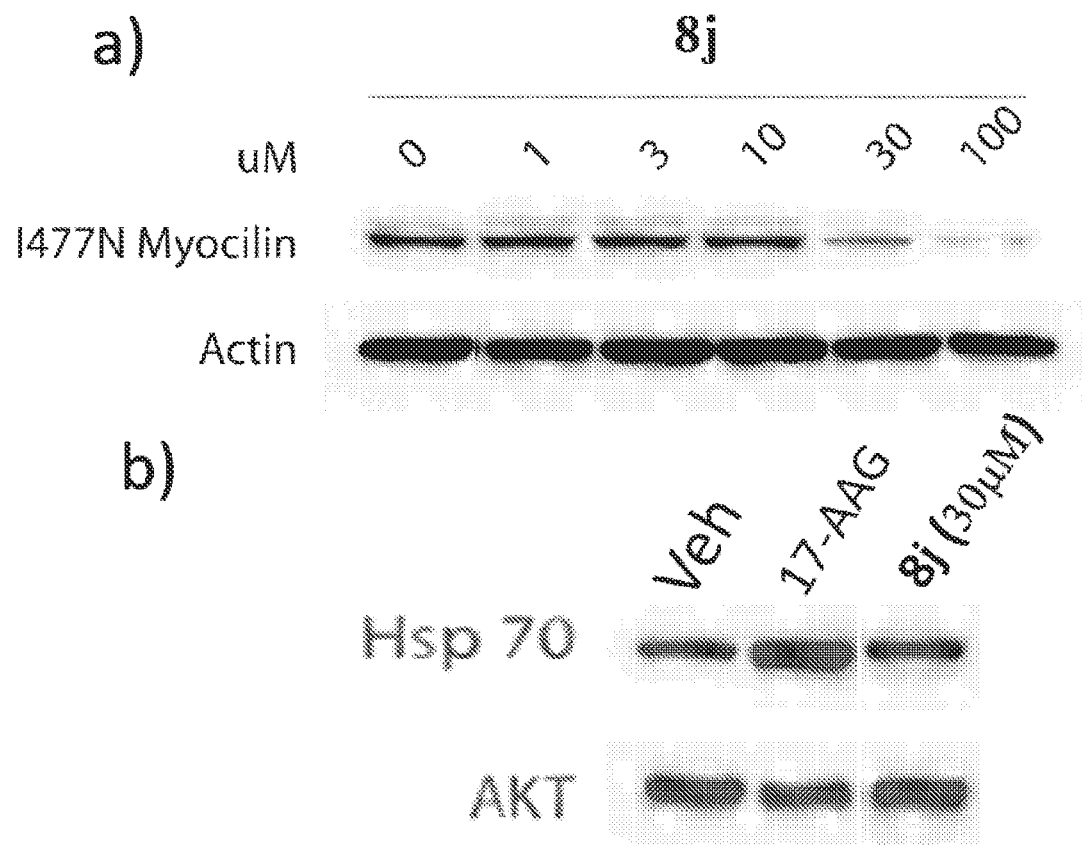
FIGS. 4A-B provide the Western blot analysis of a compound of the present technology (8j) on the levels of mutant myocilin (FIG. 4A) and Hsp70 and Akt with 5 μM of 17-AAG as reference (FIG. 4B).

As shown in FIG. 3, Grp94 inhibitors 8e and 8j each inhibited cell motility and prevent cancer cell migration. Without being bound by theory, these results indicate that compounds of the present technology prevent cancer cell migration by affecting F-actin polymerization and integrin trafficking, providing a clear mechanism by which Grp94 inhibitors inhibit the metastatic process. Recently, Grp94 inhibition was shown to diminish cell migration and metastasis in the highly metastatic breast cancer cell lines, MDA-MB-231 and ROS-resistant, MCF-7.[20] The migratory activity of these cells were therefore determined by employing a wound healing scratch assay. It was observed that compounds 8j and 8e inhibited migration of the highly metastatic breast cancer cell line MDA-MB-231 (FIG. 3A) as well as the highly metastatic prostate cancer cell line PC-3 MM-2 (FIG. 3B), at 10 µM and 5 µM respectively. The anti-proliferative activity manifested by these compounds did not affect the proliferation of MDA-MB-231 or PC-3 MM-2 cells (>95% viability at 25 µM 8j and 8e), suggesting that the anti-migratory activity manifested by these compounds does not result from anti-proliferative activity. Taken together, the results show that these Grp94 inhibitors inhibit cell migration by disrupting integrin trafficking and filamentous actin rearrangement.

Disaggregation of mutant myocilin with Grp94 inhibitors: Myocilin is a secreted protein found in trabecular meshwork (TM) tissue in the anterior anatomical segment of the eye. Gain of toxic function mutations in the MYOC gene lead to abnormal myocilin that readily accumulates and aggregates, leading to reduced aqueous humor outflow facility through the TM in the anterior chamber of the eye. As a result, intraocular pressure (IOP) is increased and contributes to primary open angle glaucoma (POAG), a degenerative eye disease.[41] Previous studies have found a link between the accumulation of aggregated mutant myocilin and the ER-associated chaperone, Grp94 and that the inhibition of Grp94 with small molecules is a viable therapeutic approach that can potentially lead to the alleviation of known POAG pathologies via increased clearance of myocilin aggregates from the ER.[21] Therefore, varying doses of inhibitors of the present technology were evaluated in an assay that measured the levels of I477N mutant myocilin levels expressed in tetracycline inducible HEK cells that conditionally over-express the I477N mutant form of myocilin. In the western blot analysis shown in FIG. 3A, compound 8j exhibited a significant decrease in mutant myocilin levels at 30 µM. Effect of drug on cytosolic Hsp90 client protein maturation was also determined. As can be seen in FIG. 3B, compound 8j did not affect Akt maturation at the same concentration, Akt is a well-established Hsp90-dependent client. Furthermore, Hsp70 levels remained unaffected with 8j when compared to 17-AAG, which is a pan-inhibitor of all four Hsp90 isoforms.

In-Vivo Model for Glaucoma

Inhibitor application and study duration: A compound of the present technology will be solubilized in DMSO and diluted with dilute saline to give 1% DMSO concentration (containing ~10× concentration of the compound $IC_{50}$ required for myocilin reduction). Once a day, restrained C57BL/6 mice will be administered with 1 drop (~10 µL) of compound-containing solution topically via eye drop. After allowing the drop to sit on the eye for 1 minute the mouse will return to its cage. This dosing regimen will continue for 14 weeks. Control mice will be subject to the same dosing regimen except using dilue saline with 1% DMSO (i.e., with no compound of the present technology).

Intraocular Pressure (IOP) Measurements: Intraocular pressure (IOP) levels in the mouse eye will be obtained using a rebound tonometer bi-weekly [is the IOP measured once every two weeks (bi-weekly), or will IOP be measured twice a week (semi-weekly)?] using mice anesthetized with isoflourane at a 3-4% flow rate and restrained. 6 IOP measurements per eye will be determined. After determining the standard deviation of the measurements, mice will be returned to their cages. Animals will not be anesthetized more than 2 minutes during the IOP measurement process.

Results: It is expected that mice receiving administration of compounds of the present technology will exhibit a reduction in IOP as compared to control mice In-vivo model for Cancer: A standard xenograft mouse model will be used for studying the in-vivo effects of compounds of the present technology on metastasis and proliferation of a tumor. It is expected that mice receiving administration of compounds of the present technology will exhibit a reduction in metastasis and/or proliferation of the turner as compared to control mice receiving vehicle.

REFERENCES

1. Taipale, M.; Jarosz, D. F.; Lindquist, S., HSP90 at the hub of protein homeostasis: emerging mechanistic insights. *Nat. Rev. Mol. Cell Biol.* 2010, 11, 515-528.
2. Trepel, J.; Mollapour, M.; Giaccone, G.; Neckers, L., Targeting the dynamic HSP90 complex in cancer. *Nat. Rev. Cancer* 2010, 10, 537-549.
3. Donnelly, A.; Blagg, B. S. J., Novobiocin and Additional Inhibitors of the Hsp90 C-Terminal Nucleotide-binding Pocket. *Curr. Med. Chem.* 2008, 15, 2702-2717.
4. Powers M V, Workman P. Inhibitors of the heat shock response: biology and pharmacology. *FEBS Lett.* 2007, 581, 3758-69.
5. Whitesell, L.; Bagatell, R.; Falsey, R. The stress response: implications for the clinical development of Hsp90 inhibitors. *Curr. Cancer Drug Targets* 2003, 3, 349-358.
6. Whitesell, L.; Lindquist, S. L. Hsp90 and the chaperoning of cancer. *Nat. Rev. Cancer* 2005, 5, 761-772.
7. Zhang, H.; Burrows, F. Targeting multiple signal transduction pathways through inhibition of Hsp90. *J. Mol. Med.* 2004, 82, 488-499.
8. Pearl, L. H.; Prodromou, C. Structure and in vivo function of Hsp90. *Curr. Opin. Struct. Biol.* 2000,10, 46-51.
9. Prodromou, C., Pearl, L. H. Structure and functional relationships of Hsp90. *Curr. Cancer Drug Targets* 2003, 3, 301-323.
10. DeBoer C, Meulman P A, Wnuk R J, Peterson D H., Geldanamycin, a new antibiotic. *J Antibiot* 1970, 23, 442-7.
11. Whitesell, L.; Mimnaugh, E. G.; De Costa, B.; Myers, C. E.; Neckers, L. M., Inhibition of heat shock protein HSP90-pp60v-src heteroprotein complex formation by benzoquinone ansamycins: essential role for stress proteins in oncogenic transformation. *Proc. Natl. Acad. Set. USA* 1994, 91, 8324-8.

12. Messaoudi, S.; Peyrat, J. F.; Brion, J. D.; Alami, M., Recent advances in Hsp90 inhibitors as antitumor agents. *Anti-cancer agents med chem.* 2008, 8, 761-82.

13. Kim, Y. S.; Alarcon, S. V.; Lee, S.; Lee, M. J.; Giaccone, G.; Neckers, L.; Trepel, J. B. Update on Hsp90 inhibitors in clinical trial. *Curr. Top. Med. Chem.* 2009, 9, 1479-1492.

14. Biamonte, M. A.; Van de Water, R.; Arndt, J. W.; Scannevin, R. H.; Perret, D.; Lee, W. Heat shock protein 90: inhibitors in clinical trials. *J. Med. Chem.* 2010, 53, 3-17.

15. Peterson, L. B.; Esker, J. D.; Vielhauer, G. A.; Blagg, B. S. The hERG channel is dependent upon the Hsp90a isoform for maturation and trafficking. *Mol. Pharm.* 2012, 9, 1841-1846.

16. Sreedhar, A S.; Kalmar, E.; Csermely, P.; Shen, Y. F. Hsp90 isoforms: functions, expression and clinical importance. *FEBS Lett.* 2004, 562, 11-15.

17. Kozutsumi, Y.; Segal, M.; Normington, K.; Gething, M.; Sambrook, J. The presence of malfolded proteins in the endoplasmic reticulum signals the induction of glucose-regulated proteins. *Nature* 1988, 332, 462-464.

18. Li, Z.; Srivastava, P. K., Tumor rejection antigen gp96/grp94 is an ATPase: implications for protein folding and antigen presentation. *EMBO J.* 1993, 12, 3143-51.

19. Goodman, S. L.; Picard, M. Integrins as therapeutic targets. *Trends Pharmacol. Sci.* 2012, 33, 405-412.

20. Dejeans, N.; Glorieux, C.; Guenin, S.; Beck, R.; Sid, B.; Rousseau, R.; Bisig, B.; Delvenne, P.; Buc Calderon, P.; Verrax, J. Overexpression of Grp94 in breast cancer cells resistant to oxidative stress promotes high levels of cancer cell proliferation and migration: implications for tumor recurrence. *Free Radic. Biol. Med.* 2012, 52, 993-1002.

21. Suntharalingam, A.; Abisambra, J. F.; O'Leary, J. C. III; Koren, J. Ill; Zhang, B.; Joe, M. K.; Blair, L. J.; Hill, S. E.; Jinwal, U. K.; Cockman, M.; Duerfeldt, A. S.; Tomarev, S.; Blagg, B. S.; Lieberman, R. L.; Dickey, C. A. Glucose-regulated protein 94 triage of mutant myocilin through endoplasmic reticulum-associated degradation subverts a more efficient autophagic clearance mechanism. *J. Biol. Chem.* 2012, 287, 40661-40669.

22. Gullo, C. A.; Teoh, G. Heat shock protein: to present or not, that is the question. *Immunol. Lett.* 2004, 94, 1-10.

23. Obeng, E. A.; Carlson, L. M.; Gutman, D. M.; Harrington, W. J.; Lee, K. P.; Boise, L. H. Proteasome inhibitors induce a terminal unfolded protein response in multiple myeloma cells. *Blood,* 2006, 107, 4907-4916.

24. Hua, Y.; White-Gilbertson, S.; Kellner, I; Rachidi, S.; Usmani, S. Z.; Chiosis, G.; DePinho, R.; Li, Z.; Liu, B. Molecular chaperone gp96 is a novel therapeutic target for multiple myeloma. *Clin. Cancer Res.* 2013, 19, 6242-6251.

25. Chen, B.; Piel, W. H.; Gui, L.; Bruford, E.; Monteiro, A. The HSP90 family of genes in the human genome: insights into their divergence and evolution. *Genomics* 2005, 86, 627-637.

26. Soldano, K. L.; Jivan, A.; Nicchitta, C. V.; Gewirth, D. T. Structure of the N-terminal domain of Grp94. Basis for ligand specificity and regulation. J. Biol. Chem. 2003, 278, 48330-48338.

27. Cristalli, G.; Lambertucci, C.; Taffi, S.; Vittori, S.; Volpini, R. Medicinal chemistry of adenosine A2A receptor agonists. *Curr. Top. Med. Chem.* 2003, 3, 387-401.

28. Immormino, R. M.; Metzger, L. E.; Reardon, P. N.; Dollins, D. E.; Blagg, B. S.; Gewirth, D. T. Different poses for ligand and chaperone in inhibitor-bound Hsp90 and Grp94: implications for paralog-specific drug design. *J. Mol. Biol.* 2009, 388, 1033-1042.

29. Patel, P. D.; Yan, P.; Seidler, P. M.; Patel, H. J.; Sun, W.; Yang, C.; Que, N. S.; Taldone, T.; Finotti, P.; Stephani, R. A.; Gewirth, D. T.; Chiosis, G. Paralog-selective Hsp90 inhibitors define tumor-specific regulation of HER2. *Nat. Chem. Biol.* 2013, 9, 677-684.

30. Duerfeldt, A. S.; Peterson, L. B.; Maynard, J. C.; Ng, C. L.; Eletto, D.; Ostrovsky, O.; Shinogle, H. E.; Moore, D. S.; Argon, Y.; Nicchitta, C. V.; Blagg, B. S. J., Development of a Grp94 inhibitor. *J. Am. Chem. Soc.* 2012, 134, 9796-9804.

31. Crowley, V. M.; Khandelwal, A.; Mishra, S.; Stothert, A. R.; Huard, D. J. E.; Zhao, J.; Muth, A.; Duerfeldt, A. S.; Kizziah, J. L.; Lieberman, R. L.; Dickey, C. A.; Blagg, B. S. I, Development of Glucose Regulated Protein 94-Selective Inhibitors Based on the BnIm and Radamide Scaffold. *J. Med Chem.* 2016,59, 3471-3488.

32. Ernst, J. T.; Liu, M.; Zuccola, H.; Neubert, T.; Beaumont, K.; Turnbull, A.; Kallel, A.; Vought, B.; Stamos, D., Correlation between chemotype-dependent binding conformations of HSP90α/β and isoform selectivity— Implications for the structure-based design of HSP90α/β selective inhibitors for treating neurodegenerative diseases. *Bioorg. Med Chem. Lett.* 2014, 24, 204-208.

33. Gilow, H.; Burton, D. Bromination and chlorination of pyrrole and some reactive 1-substituted pyrroles. *J. Org. Chem.* 1981, 46, 2221-2225.

34. Chen, W.; Stephenson, E. K.; Cava, M. P.; Jackson, Y. A., 2-Substituted Pyrroles from N-tert-Butoxycarbonyl-2-Bromopyrrole: N-tert-Butoxycarbonyl-2-Trimethylsilylpyrrole. In Organic Syntheses, John Wiley & Sons, Inc.: 2003.

35. Chakrabarty, M.; Kundu, T.; Harigaya, Y. Mild Deprotection Of Tert-Butyl Carbamates Of NH-Heteroarenes Under Basic Conditions. *Syn. Comm.* 2006, 36, 2069-2077.

36. Bohm, H. J.; Banner, D.; Bendels, S.; Kansy, M.; Kuhn, B.; Muller, K.; Obst-Sander, U.; Stahl, M., Fluorine in medicinal chemistry. *Chembiochem.* 2004, 5, 637-43.

37. Ghosh, S.; Shinogle, H. E.; Galeva, N. A.; Dobrowsky, R. T.; Blagg, B. S. J., Endoplasmic Reticulum Resident Heat Shock Protein 90 (Hsp90) Isoform Glucose-Regulated Protein 94 (Grp94) Regulates Cell Polarity and Cancer Cell Migration by Affecting Intracellular *Transport. J. Biol. Chem.* 2016,291, 8309-8323.

38. Rachidi, S.; Sun, S.; Li, Z., Endoplasmic reticulum heat shock protein gp96/grp94 is a pro-oncogenic chaperone, not a tumor suppressor. *Hepatology* 2015, 61, 1766-1767.

39. Mattila, P. K.; Lappalainen, P., Filopodia: molecular architecture and cellular functions. *Nat Rev Mol Cell Biol.* 2008, 9, 446-454.

40. Wang, N.; Feng, Y.; Lau, E. P.; Tsang, C.; Ching, Y.; Man, K.; Tong, Y.; Nagamatsu, T.; Su, W.; Tsao, S., F-actin reorganization and inactivation of rho signaling pathway involved in the inhibitory effect of Coptidis Rhizoma on hepatoma cell migration. *Integrative cancer therapies.* 2010, 9, 354-64.

41. Stothert, A.; Suntharalingam, A.; Huard, D.; Fontaine, S.; Crowley, V.; Mishra, S.; Blagg, B.; Lieberman, R.; Dickey, C. Exploiting the interaction between Grp94 and aggregated myocilin to treat glaucoma. *Hum. Mol Gen.* 2014, 23, 6470-80.

42. Okado-Matsumoto, A.; Fridovich, I., Subcellular distribution of superoxide dismutases (SOD) in rat liver: Cu,Zn-SOD in mitochondria. *J. Biol. Chem.* 2001,276, 38388-93.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula I

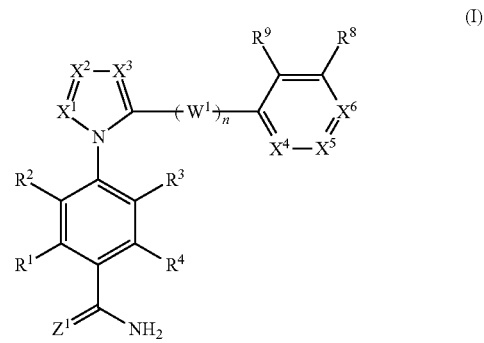

or a pharmaceutically acceptable salt and/or solvate thereof, wherein $X^1$, $X^2$, and $X^3$ are each independently CH or N;

$X^4$ is N or C—$R^5$;

$X^5$ is N or C—$R^6$;

$X^6$ is N or C—$R^7$;

$W^1$ is C($R^{10}$)($R^U$), O, or S;

$R^1$ is alkyl, cycloalkyl, aryl, heterocyclyl, or $X^7$—$R^{12}$;

$R^2$, $R^3$, $R^4$, $R^5$, $R^6$, $R^7$, $R^8$, $R^9$, $R^{10}$, and $R^{11}$ are each independently H, OH, alkyl, alkoxy, aryloxy, heteroaryloxy, amino, halo, trifluoromethyl, or cyano;

$X^7$ is O, S, or NH;

$R^{12}$ is alkyl, cycloalkyl, aryl, or heterocyclyl;

$Z^1$ is O, S, or NH; and n is 0 or 1.

B. The compound of Paragraph A, wherein the compound is of Formula Ia

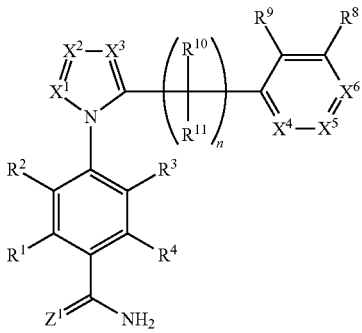

(Ia)

or a pharmaceutically acceptable salt and/or solvate thereof.

C. The compound of Paragraph A or Paragraph B, wherein
$X^4$ is C—$R^5$;
$X^5$ is N; and
$X^6$ is C—$R^7$.

D. The compound of any one of Paragraphs A-C, wherein $R^1$ is $C_1$-$C_6$ alkyl, $C_3$-$C_6$ cycloalkyl, a substituted or unsubstituted phenyl, $C_2$-$C_5$ heterocyclyl, or $X^7$—$R^{12}$.

E. The compound of any one of Paragraphs A-D, wherein $R^{12}$ is $C_1$-$C_6$ alkyl, $C_3$-$C_6$ cycloalkyl, a substituted or unsubstiued phenyl, or $C_2$-$C_5$ heterocyclyl.

F. The compound of any one of Paragraphs A-E, wherein $R^{12}$ is $C_1$-$C_6$ alkyl, $C_3$-$C_6$ cycloalkyl, substituted or unsubstituted phenyl, or non-aromatic $C_2$-$C_5$ heterocyclyl.

G. The compound of any one of Paragraphs A-F, wherein $R^1$ is isopropyl, tert-butyl, cyclopropyl, cyclobutyl, cyclopentyl, cyclohexyl,

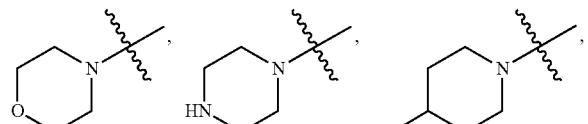

or

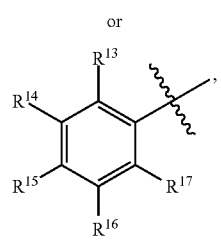

where $R^{13}$, $R^{14}$, $R^{15}$, $R^{16}$ and $R^{17}$ are each independently H, alkyl, alkoxy, amino, halo, trifluoromethyl, or cyano.

H. The compound of any one of Paragraphs A-G, wherein $R^{12}$ is isopropyl, tert-butyl, cyclopropyl, cyclobutyl, cyclopentyl, cyclohexyl,

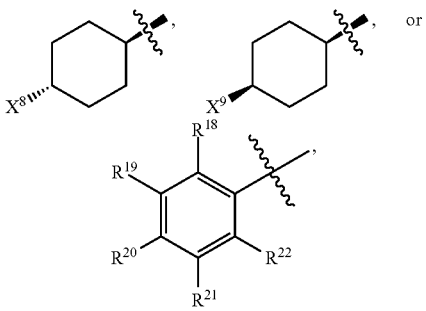

where
$X^8$ and $X^9$ are each independently OH, amino, SH, sulfide, sulfoxide, or sulfone; and
$R^{18}$, $R^{19}$, $R^{20}$, $R^{21}$ and $R^{22}$ are each independently H, alkyl, alkoxy, amino, halo, trifluoromethyl, or cyano.

I. The compound of any one of Paragraphs A-H, wherein $R^5$, $R^6$, and $R^7$ are each independently H, OH, alkyl, alkoxy, aryloxy, heteroaryloxy, amino, halo, trifluoromethyl, or cyano; and
$R^8$ and $R^9$ are each H.

J. The compound of any one of Paragraphs A-I, wherein one of $R^5$, $R^6$, and $R^7$ is OH, alkyl, alkoxy, aryloxy, heteroaryloxy, amino, halo, trifluoromethyl, or cyano, and the remaining $R^5$, $R^6$, and $R^7$ are each H;
$R^8$ and $R^9$ are each H.

K. The compound of any one of Paragraphs A-J, wherein one of $R^5$, $R^6$, and $R^7$ is OH, $C_1$-$C_6$ alkyl, $C_1$-$C_6$ alkoxy, amino, halo, trifluoromethyl, or cyano, and the remaining $R^5$, $R^6$, and $R^7$ are each H;
$R^8$ and $R^9$ are each H.

L. The compound of any one of Paragraphs A-K, wherein one of $R^5$, $R^6$, and $R^7$ is OH, methyl, ethyl, n-propyl, isopropyl, methoxy, ethoxy, w-propyloxy, isopropyloxy, $NH_2$, NH—$CH_3$, N($CH_3$)$_2$, halo, trifluoromethyl, or cyano, and the remaining $R^5$, $R^6$, and $R^7$ are each H;
$R^8$ and $R^9$ are each H.

M. The compound of any one of Paragraphs A-L, wherein $R^{10}$ and $R^{11}$ are each H.

N. The compound of any one of Paragraphs A, B, and D-M, wherein the compound Formula I is of Formula II

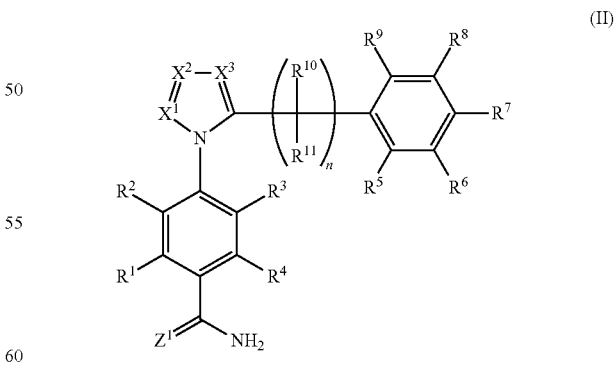

(II)

or a pharmaceutically acceptable salt and/or solvate thereof.

O. The compound of any one of Paragraphs A-N, wherein $X^1$, $X^2$, and $X^3$ are each CH.

P. A composition comprising a compound of any one of Paragraphs A-O and a pharmaceutically acceptable carrier.

Q. A pharmaceutical composition for treating cancer or glaucoma, the composition comprising an effective amount of the compound of any one of Paragraphs A-O and a pharmaceutically acceptable excipient.

R. The pharmaceutical composition of Paragraph Q, wherein the cancer is multiple myeloma, breast cancer, or prostate cancer.

S. The pharmaceutical composition of Paragraph Q, wherein the pharmaceutical composition is for treating glaucoma.

T. The pharmaceutical composition of Paragraph S, wherein the glaucoma is myocilin glaucoma.

U. The pharmaceutical composition of any one of Paragraphs Q-T, wherein the pharmaceutical composition is packaged in unit dosage form.

V. A method for inhibiting cell motility of a cancer cell, the method comprising contacting the cancer cell with a compound of any one of Paragraphs A-O.

W. The method of Paragraph V, wherein the cancer cell is a multiple myeloma cancer cell, a breast cancer cell, or prostate cancer cell.

X. The method of Paragraph V or Paragraph W, wherein the method comprises contacting the cell with an effective amount of the compound.

Y. The method of any one of Paragraphs V-X, wherein the cancer cell is not within a patient.

Z. A method of inhibiting death of a cell exhibiting mutant myocilin, the method comprising contacting the cell with a compound of any one of Paragraphs A-O.

AA. The method of Paragraph Z, wherein the method comprises contacting the cell with an effective amount of the compound.

AB. The method of Paragraph Z or Paragraph AA, wherein the contacting inhibits the death of the cell in comparison to a cell exhibiting mutant myocilin that is not contacted with the compound.

AC. A method of treating a patient or animal suffering from cancer or glaucoma, the method comprising administration of an effective amount of a compound of any one of Paragraphs A-O to the patient or animal suffering from the cancer or the glaucoma.

AD. The method of Paragraph AC, wherein administration of the effective amount of the compound to the patient or animal treats the patient or animal suffering from the cancer or the glaucoma.

AE. The method of Paragraph AC or Paragraph AD, wherein the cancer is multiple myeloma, breast cancer, or prostate cancer.

AF. The method of any one of Paragraphs AC-AE, wherein the glaucoma is myocilin glaucoma.

AG. The method of any one of Paragraphs AC-AF, wherein the administration comprises oral administration, parenteral administration, or nasal administration.

AH. A compound according to Formula III

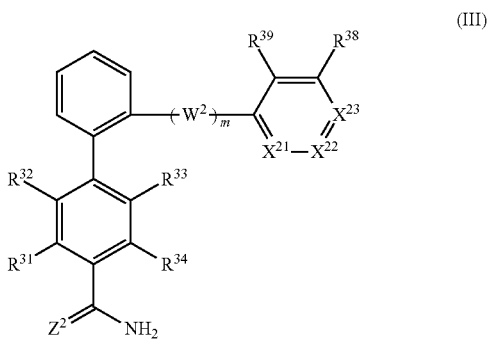

(III)

or a pharmaceutically acceptable salt and/or solvate thereof, wherein $X^{21}$ is N or C—$R^{35}$;

$X^{22}$ is N or C—$R^{36}$;

$X^{23}$ is N or C—$R^{37}$;

$W^2$ is $C(R^{40})(R^{41})$, O, or S;

$R^{31}$ is alkyl, cycloalkyl, aryl, heterocyclyl, or $X^{24}$—$R^{42}$;

$R^{32}$, $R^{33}$, $R^{34}$, $R^{35}$, $R^{36}$, $R^{37}$, $R^{38}$, $R^{39}$, $R^{40}$, and $R^{41}$ are each independently H, OH, alkyl, alkoxy, aryloxy, heteroaryloxy, amino, halo, trifluoromethyl, or cyano;

$X^{24}$ is O, S, or NH;

$R^{42}$ is alkyl, cycloalkyl, aryl, or heterocyclyl;

$Z^2$ is O, S, or NH; and m is 0 or 1.

AI. The compound of Paragraph AH, wherein $R^{31}$ is Q-Ce alkyl, $C_3$-$C_6$ cycloalkyl, a substituted or unsubstituted phenyl, $C_2$-$C_5$ heterocyclyl, or $X^{24}$—$R^{42}$.

AJ. The compound of Paragraph AH or Paragraph AI, wherein $R^{42}$ is $C_1$-$C_6$ alkyl, $C_3$-$C_6$ cycloalkyl, a substituted or unsubstitued phenyl, or $C_2$-$C_5$ heterocyclyl.

AK. The compound of any one of Paragraphs AH-AJ, wherein $R^{42}$ is $C_1$-$C_6$ alkyl, $C_3$-$C_6$ cycloalkyl, substituted or unsubstituted phenyl, or non-aromatic $C_2$-$C_5$ heterocyclyl.

AL. The compound of any one of Paragraphs AH-AK, wherein $R^{31}$ is isopropyl, tert-butyl, cyclopropyl, cyclobutyl, cyclopentyl, cyclohexyl,

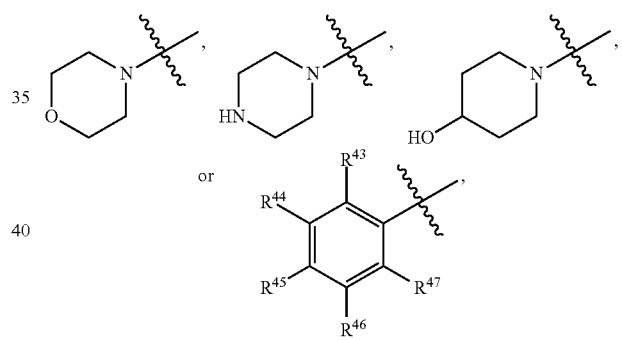

where $R^{43}$, $R^{44}$, $R^{45}$, $R^{46}$ and $R^{47}$ are each independently H, alkyl, alkoxy, amino, halo, trifluoromethyl, or cyano.

AM. The compound of any one of Paragraphs AH-AL, wherein $R^{42}$ is isopropyl, tert-butyl, cyclopropyl, cyclobutyl, cyclopentyl, cyclohexyl,

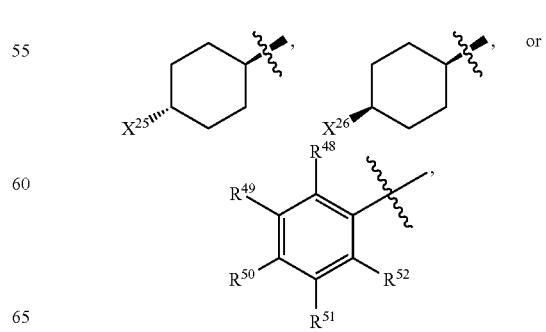

where
X²⁵ and X²⁶ are each independently OH, amino, SH, sulfide, sulfoxide, or sulfone; and
R⁴⁸, R⁴⁹, R⁵⁰, R⁵¹ and R⁵² are each independently H, alkyl, alkoxy, amino, halo, trifluoromethyl, or cyano.

AN. A composition comprising a compound of any one of Paragraphs AH-AM and a pharmaceutically acceptable carrier.

AO. A pharmaceutical composition for treating cancer or glaucoma, the composition comprising an effective amount of the compound of any one of Paragraphs AH-AM and a pharmaceutically acceptable excipient.

AP. The pharmaceutical composition of Paragraph AO, wherein the cancer is multiple myeloma, breast cancer, or prostate cancer.

AQ. The pharmaceutical composition of Paragraph AO, wherein the pharmaceutical composition is for treating glaucoma.

AR. The pharmaceutical composition of Paragraph AQ, wherein the glaucoma is myocilin glaucoma.

AS. The pharmaceutical composition of any one of Paragraphs AO-AR, wherein the pharmaceutical composition is packaged in unit dosage form.

AT. A method for inhibiting cell motility of a cancer cell, the method comprising contacting the cancer cell with a compound of any one of Paragraphs AH-AM.

AU. The method of Paragraph AT, wherein the cancer cell is a multiple myeloma cancer cell, a breast cancer cell, or prostate cancer cell.

AV. The method of Paragraph AT or Paragraph AU, wherein the method comprises contacting the cell with an effective amount of the compound.

AW. The method of any one of Paragraphs AT-AV, wherein the cancer cell is not within a patient.

AX. A method of inhibiting death of a cell exhibiting mutant myocilin, the method comprising contacting the cell with a compound of any one of Paragraphs AH-AM.

AY. The method of Paragraph AX, wherein the method comprises contacting the cell with an effective amount of the compound.

AZ. The method of Paragraph AX or Paragraph AY, wherein the contacting inhibits the death of the cell in comparison to a cell exhibiting mutant myocilin that is not contacted with the compound.

BA. A method of treating a patient or animal suffering from cancer or glaucoma, the method comprising administration of an effective amount of a compound of any one of Paragraphs AH-AM to the patient or animal suffering from the cancer or the glaucoma.

BB. The method of Paragraph BA, wherein administration of the effective amount of the compound to the patient or animal treats the patient or animal suffering from the cancer or the glaucoma.

BC. The method of Paragraph BA or Paragraph BB, wherein the cancer is multiple myeloma, breast cancer, or prostate cancer.

BD. The method of any one of Paragraphs BA-BC, wherein the glaucoma is myocilin glaucoma.

BE. The method of any one of Paragraphs BA-BD, wherein the administration comprises oral administration, parenteral administration, or nasal administration.

Other embodiments are set forth in the following claims, along with the full scope of equivalents to which such claims are entitled.

What is claimed is:

1. A compound according to Formula III

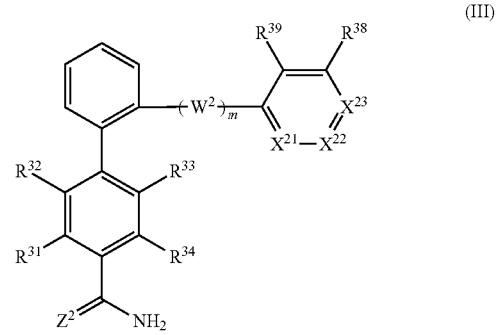

(III)

or a pharmaceutically acceptable salt and/or solvate thereof, wherein
X²¹ is N or C—R³⁵;
X²² is N or C—R³⁶;
X²³ is N or C—R³⁷;
W² is C(R⁴⁰)(R⁴¹), O, or S;
R³¹ is alkyl, cycloalkyl, aryl, heterocyclyl, or X²⁴—R⁴²;
R³², R³³, R³⁴, R³⁵, R³⁶, R³⁷, R³⁸, R³⁹, R⁴⁰, and R⁴¹ are each independently H, OH, alkyl, alkoxy, aryloxy, heteroaryloxy, amino, halo, trifluoromethyl, or cyano;
X²⁴ is O, S, or NH;
R⁴² is alkyl, cycloalkyl, aryl, or heterocyclyl;
Z² is O, S, or NH; and
m is 0 or 1.

2. The compound of claim 1, wherein R⁴² is C₁-C₆ alkyl, C₃-C₆ cycloalkyl, a substituted or unsubstituted phenyl, or C₂-C₅ heterocyclyl.

3. The compound of claim 1, wherein R⁴² is C₁-C₆ alkyl, C₃-C₆ cycloalkyl, substituted or unsubstituted phenyl, or non-aromatic C₂-C₅ heterocyclyl.

4. The compound of claim 1, wherein R³¹ is isopropyl, tert-butyl, cyclopropyl, cyclobutyl, cyclopentyl, cyclohexyl,

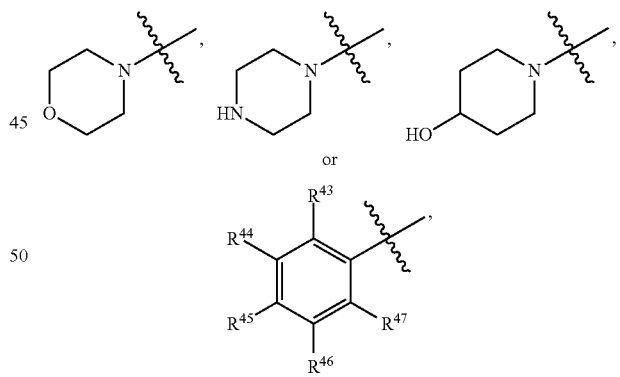

where R⁴³, R⁴⁴, R⁴⁵, R⁴⁶ and R⁴⁷ are each independently H, alkyl, alkoxy, amino, halo, trifluoromethyl, or cyano.

5. The compound of claim 1, wherein R⁴² is isopropyl, tert-butyl, cyclopropyl, cyclobutyl, cyclopentyl, cyclohexyl,

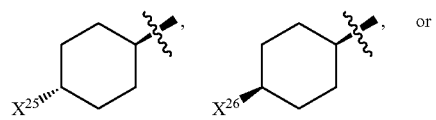

-continued

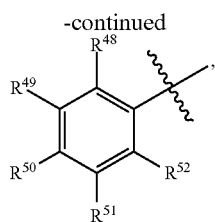

where
X$^{25}$ and X$^{26}$ are each independently OH, amino, SH, sulfide, sulfoxide, or sulfone; and
R$^{48}$, R$^{49}$, R$^{50}$, R$^{51}$ and R$^{52}$ are each independently H, alkyl, alkoxy, amino, halo, trifluoromethyl, or cyano.

6. A composition comprising a compound of claim 1 and a pharmaceutically acceptable carrier.

7. A pharmaceutical composition for treating cancer or glaucoma, the composition comprising an effective amount of the compound of claim 1 and a pharmaceutically acceptable excipient.

8. The pharmaceutical composition of claim 7, wherein the cancer is multiple myeloma, breast cancer, or prostate cancer.

9. The pharmaceutical composition of claim 7, wherein the pharmaceutical composition is for treating glaucoma.

10. The pharmaceutical composition of claim 9, wherein the glaucoma is myocilin glaucoma.

11. A method for inhibiting cell motility of a cancer cell, the method comprising contacting the cancer cell with a compound of claim 1.

12. The method of claim 11, wherein the cancer cell is a multiple myeloma cancer cell, a breast cancer cell, or prostate cancer cell.

13. A method of inhibiting death of a cell exhibiting mutant myocilin, the method comprising contacting the cell with a compound of claim 1.

14. The method of claim 13, wherein the method comprises contacting the cell with an effective amount of the compound.

15. The method of claim 13, wherein the contacting inhibits the death of the cell in comparison to a cell exhibiting mutant myocilin that is not contacted with the compound.

16. A method of treating a patient or animal suffering from cancer or glaucoma, the method comprising administration of an effective amount of a compound of claim 1 to the patient or animal suffering from the cancer or the glaucoma.

17. The method of claim 16, wherein administration of the effective amount of the compound to the patient or animal treats the patient or animal suffering from the cancer or the glaucoma.

18. The method of claim 16, wherein the cancer is multiple myeloma, breast cancer, or prostate cancer.

19. The method of claim 16, wherein the glaucoma is myocilin glaucoma.

20. The method of claim 16, wherein the administration comprises oral administration, parenteral administration, or nasal administration.

* * * * *